United States Patent
Maecker et al.

(10) Patent No.: US 9,724,413 B2
(45) Date of Patent: Aug. 8, 2017

(54) METHODS OF TREATING CANCER USING PD-1 AXIS BINDING ANTAGONISTS AND MEK INHIBITORS

(75) Inventors: Heather Maecker, Palo Alto, CA (US); Bryan Irving, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 301 days.

(21) Appl. No.: 14/236,064

(22) PCT Filed: Aug. 1, 2012

(86) PCT No.: PCT/US2012/049233
§ 371 (c)(1),
(2), (4) Date: Jul. 30, 2014

(87) PCT Pub. No.: WO2013/019906
PCT Pub. Date: Feb. 7, 2013

(65) Prior Publication Data
US 2014/0341902 A1 Nov. 20, 2014

Related U.S. Application Data

(60) Provisional application No. 61/574,406, filed on Aug. 1, 2011.

(51) Int. Cl.
| | |
|---|---|
| A61K 39/395 | (2006.01) |
| C07K 16/28 | (2006.01) |
| C07K 16/30 | (2006.01) |
| A61K 31/4184 | (2006.01) |
| A61K 31/4355 | (2006.01) |
| A61K 31/44 | (2006.01) |
| A61K 31/4523 | (2006.01) |
| A61K 31/519 | (2006.01) |
| A61K 47/48 | (2006.01) |
| A61K 39/00 | (2006.01) |

(52) U.S. Cl.
CPC .... *A61K 39/39558* (2013.01); *A61K 31/4184* (2013.01); *A61K 31/4355* (2013.01); *A61K 31/44* (2013.01); *A61K 31/4523* (2013.01); *A61K 31/519* (2013.01); *A61K 47/48238* (2013.01); *C07K 16/2827* (2013.01); *C07K 16/3046* (2013.01); *C07K 16/3053* (2013.01); *A61K 2039/505* (2013.01)

(58) Field of Classification Search
CPC .................................................. A61K 39/395
USPC ........................................... 424/139.1, 133.1
See application file for complete search history.

(56) References Cited

U.S. PATENT DOCUMENTS

| | | |
|---|---|---|
| 4,708,871 A | 11/1987 | Geysen |
| 4,816,567 A | 3/1989 | Cabilly et al. |
| 4,833,092 A | 5/1989 | Geysen |
| 5,223,409 A | 6/1993 | Ladner et al. |
| 5,403,484 A | 4/1995 | Ladner et al. |
| 5,428,130 A | 6/1995 | Capon et al. |
| 5,545,806 A | 8/1996 | Lonberg et al. |
| 5,545,807 A | 8/1996 | Surani et al. |
| 5,556,762 A | 9/1996 | Pinilla et al. |
| 5,569,825 A | 10/1996 | Lonberg et al. |
| 5,571,689 A | 11/1996 | Heuckeroth et al. |
| 5,591,828 A | 1/1997 | Bosslet et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,663,143 A | 9/1997 | Ley et al. |
| 5,750,373 A | 5/1998 | Garrard et al. |
| 6,075,181 A | 6/2000 | Kucherlapati et al. |
| 6,150,584 A | 11/2000 | Kucherlapati et al. |
| 6,982,321 B2 | 1/2006 | Winter |
| 7,087,409 B2 | 8/2006 | Barbas, III et al. |
| 8,217,149 B2 | 7/2012 | Irving et al. |
| 2010/0203056 A1* | 8/2010 | Irving ................ A61K 31/7068 424/139.1 |
| 2011/0086837 A1* | 4/2011 | Belvin ................ A61K 31/4523 514/210.18 |
| 2016/0222117 A1 | 8/2016 | Irving et al. |

FOREIGN PATENT DOCUMENTS

| | | |
|---|---|---|
| CA | 2385412 A1 | 11/2002 |
| EP | 0 404 097 B1 | 12/1990 |
| JP | 2005-530709 A | 10/2005 |
| JP | 2006-340714 A | 12/2006 |
| JP | 2008-501631 A | 1/2008 |
| JP | 2008-544755 A | 12/2008 |
| JP | 2009-511490 A | 3/2009 |
| JP | 2009-527521 A | 7/2009 |
| JP | 2010-501585 A | 1/2010 |
| JP | 2010-536723 A | 12/2010 |

(Continued)

OTHER PUBLICATIONS

Wiesenthal, (Human Tumor Assay Journal, on-line at http://weisenthal.org/synergy1.htm, Mar. 14, 2012).*
Berenbaum (Clin exp Immunol, 1997, 28:1-18).*
Ahmadzadeh, M. et al. "Tumor Antigen-Specific CD8 T Cells Infiltrating the Tumor Express High Levels of PD-1 and are Functionally Impaired," *Blood* 114(8):1537-1544 (Aug. 20, 2009, e-pub. May 7, 2009).
Barbas et al. "In Vitro Evolution of a Neutralizing Human Antibody to Human Immunodeficiency Virus Type 1 to Enhance Affinity and Broaden Strain Cross-Reactivity," *Proc. Nat. Acad. Sci. USA* 91:3809-3813 (Apr. 1994).

(Continued)

*Primary Examiner* — Yan Xiao
(74) *Attorney, Agent, or Firm* — Morrison & Foerster LLP

(57) ABSTRACT

The present invention describes combination treatment comprising a PD-1 axis binding antagonist and a MEK inhibitor and methods for use thereof, including methods of treating conditions where enhanced immunogenicity is desired such as increasing tumor immunogenicity for the treatment of cancer.

33 Claims, 15 Drawing Sheets

(56) References Cited

FOREIGN PATENT DOCUMENTS

| | | |
|---|---|---|
| JP | 2011-507889 A | 3/2011 |
| JP | 2011-512332 A | 4/2011 |
| TW | 201032822 A1 | 9/2010 |
| WO | WO-84/03506 A1 | 9/1984 |
| WO | WO-84/03564 A1 | 9/1984 |
| WO | WO-91/10741 A1 | 7/1991 |
| WO | WO-93/11161 A1 | 6/1993 |
| WO | WO-96/33735 A1 | 10/1996 |
| WO | WO-96/34096 A1 | 10/1996 |
| WO | WO-98/24893 A2 | 6/1998 |
| WO | WO-98/24893 A3 | 6/1998 |
| WO | WO-02/17952 A2 | 3/2002 |
| WO | WO-02/17952 A3 | 3/2002 |
| WO | WO 03/077914 A1 | 9/2003 |
| WO | WO-2004/042072 A2 | 5/2004 |
| WO | WO-2004/042072 A3 | 5/2004 |
| WO | WO-2004/042072 C1 | 5/2004 |
| WO | WO-2004/045617 A1 | 6/2004 |
| WO | WO-2004/092219 A2 | 10/2004 |
| WO | WO-2004/092219 A3 | 10/2004 |
| WO | WO-2005/094376 A2 | 10/2005 |
| WO | WO-2005/094376 A3 | 10/2005 |
| WO | WO-2005/121142 A1 | 12/2005 |
| WO | WO-2006/121168 A1 | 11/2006 |
| WO | WO-2007/005874 A2 | 1/2007 |
| WO | WO-2007/005874 A3 | 1/2007 |
| WO | WO-2007/044515 A1 | 4/2007 |
| WO | WO-2007/096259 A1 | 8/2007 |
| WO | WO-2008/024725 A1 | 2/2008 |
| WO | WO-2008/101840 A1 | 8/2008 |
| WO | WO-2009/021887 A1 | 2/2009 |
| WO | WO-2009/064675 A1 | 5/2009 |
| WO | WO-2009/073533 A2 | 6/2009 |
| WO | WO-2009/073533 A3 | 6/2009 |
| WO | WO-2009/085983 A1 | 7/2009 |
| WO | WO-2009/101611 A1 | 8/2009 |
| WO | WO-2009/114335 A2 | 9/2009 |
| WO | WO-2009/114335 A3 | 9/2009 |
| WO | WO-2010/027423 A2 | 3/2010 |
| WO | WO-2010/027423 A3 | 3/2010 |
| WO | WO-2010/027827 A2 | 3/2010 |
| WO | WO-2010/027827 A3 | 3/2010 |
| WO | WO-2010/056735 A1 | 5/2010 |
| WO | WO-2010/077634 A1 | 7/2010 |
| WO | WO-2011/057222 A1 | 5/2011 |
| WO | WO-2011/060328 A1 | 5/2011 |
| WO | WO-2011/066342 A2 | 6/2011 |
| WO | WO-2011/066342 A3 | 6/2011 |
| WO | WO-2011/109400 A2 | 9/2011 |
| WO | WO-2011/109400 A3 | 9/2011 |
| WO | WO-2013/063001 A1 | 5/2013 |
| WO | WO-2014/151634 A1 | 9/2014 |
| WO | WO-2014/159835 A1 | 10/2014 |

OTHER PUBLICATIONS

Benson et al. "The PD-1/PD-L1 Axis Modulates the Natural Killer Cell Versus Multiple Myeloma Effect: a Therapeutic Target for CT-011, a Novel Monclonal Anti-PD-1 Antibody," *Blood* 116(13):2286-2293 (Sep. 30, 2010).
Berthon et al. "In Acute Myeloid Leukemia, B7-H1 (PD-L1) Protection of Blasts From Cytotoxic T Cells is Induced by TLR Ligands and Interferon-Gamma and Can be Reveresed Using MEK Inhibitors," *Cancer Immunology, Immunotherapy* 59(12):1839-1849 (Sep. 4, 2010).
Boerner et al. "Production of Antigen-Specific Human Monoclonal Antibodies From in Vitro-Primed Human Splenocytes," *J. Immunol.* 147(1):86-95 (Jul. 1, 1991).
Boni et al. "Selective BRAF$^{V600E}$ Inhibition Enhances T-Cell Recognition of Melanoma Without Affecting Lymphocyte Function," *Cancer Res.* 70(13):5213-5219 (Jul. 1, 2010, e-pub. Jun. 15, 2010).
Bretscher et al. "A Theory of Self-Nonself Discrimination," *Science* 169:1042-1049 (Sep. 11, 1970).

Brestscher, "A Two-Step, Two-Signal Model for the Primary Activation of Precursor Helper T Cells," *Proc. Natl. Acad. Sci. USA* 96:185-190 (Jan. 1999).
Brüggemann et al. "Desinger Mice: The Production of Human Antibody Repertoires in Transgenic Animals," *Year in Immunol.* 7:33-40 (1993).
Capel et al. "Heterogeneity of Human IgG Fc Receptors," *Immunomethods* 4:25-34 (1994).
Chothia et al. "Canonical Structures for the Hypervariable Regions of Immunoglobulins," *J. Mol. Biol.* 196:901-917 (1987).
Clackson et al. "Making Antibody Fragments Using Phage Display Libraries," *Nature* 352:624-628 (Aug. 15, 1991).
Cole et al. "The EBV-Hypbridoma Techinque and Its Application to Human Lung Cancer," *Monoclonal Antibodies and Cancer Therapy*, Alan R. Liss, p. 77-96. (1985).
Cwirla et al. "Peptides on Phage: A vast Library of Peptides for Identifying Ligands," *Proc. Natl. Acad. Sci. USA* 87:6378-6382 (Aug. 1990).
Daëron. "Fc Receptor Biology," *Annu. Rev. Immunol.* 15:203-234 (1997).
De Haas et al. "Fcγ Receptors of Phagocytes," *J. Lab. Clin. Med.* 126(4):330-341 (1995).
Eggermont et al. "New drugs in Melanoma: It's a Whole New World," *European Journal of Cancer* 47(14):2510-2157 (Jul. 2011, e-pub. Jul. 27, 2011).
Fellouse et al. "Synthetic Antibodies From a Four-Amino-Acid Code: A Dominant Role for Tyrosine in Antigen Recongnition," *Proc. Natl. Acad. Sci. USA* 101(34):12467-12472 (Aug. 24, 2004).
Fishwild et al. "High-Avidity Human IgGκ Monoclonal Antibodies From a Novel Strain of Minilocus Transgenic Mice," *Nature Biotechnol.* 14:845-851 (Jul. 1996).
Genentech, Inc. "Transforming the Future of Cancer Treatment. Oncology Research and Development," located at <www.roche.com/roche_oncology_r_d_.pdf,> 16 pages.
Geysen et al. "Use of Peptide Synthesis to Probe Viral Antigens for Epitopes to a Resolution of a Single Amino Acid," *Proc. Natl. Acad. Sci. U.S.A.* 81:3998-4002 (Jul. 1984).
Geysen et al. "Small Peptides Induce Antibodies With a Sequence and Structural Requirement for Binding Antigen Comparable to Antibodies Raised Against the Native Protein," *Proc. Natl. Acad. Sci. U.S.A.* 82:178-182 (Jan. 1985).
Geysen et al. "The Delineation of Peptides Able to Mimic Assemble Epitopes," *Synthetic Peptides as Anigens. Chiba Foundation Symposium 119*, Wiley & Sons, Chichester, UK, pp. 130-149 (1986).
Geysen et al. "Stategies for Epitope Analysis Using Peptide Synthesis," *J. Immunol. Methods.* 102:259-274 (1987).
Ghetie et al., "FcRn: The MHC Class I-Related Receptor That is More Than an IgG Transporter," *Immunol. Today* 18(12):592-598 (Dec. 1997).
Ghetie et al. "Increasing the Serum Persistence of an IgG Fragment by Random Mutagenesis," *Nature Biotechnology* 15(7):637-640 (Jul. 1997).
Guyer et al. Immunoglobulin Binding by Mouse Intestinal Epithelial Cell Receptors, *J. Immunol.* 117(2):587-593 (Aug. 1976).
Hamers-Casterman et al. "Naturally Occuring Antibodies Devoid of Light Chains," *Nature* 363:446-448 (Jun. 3, 1993).
Hammerling et al. "12.1 Production of Hybridomas in the Rodent System, 12.2 Screeing Procedures *Radioimmunoassay (RIA)*, 12.3 Maintenance, Characterization of Hybridomas and Isolation of Mono-Clonal Antibodies (*Cloning Procedures*). 12.4 Radiolabelling of Monoclonal Antibodies," vol. 3, in *Mononclonal Antibodies and T-Cell hybridomas. Perspectives and Technical Advances*, Elsevier, N.Y. pp. 563-587 (1981).
Harris. "Therapeutic Monoclonals," *Biochem. Soc. Transactions* 23:1035-1038 (1995).
Hawkins et al. "Selection of Phage Antibodies by Binding Affinity Mimicking Affinity Maturation," *J. Mol. Biol.* 226:889-896 (1992).
Hinton et al. "Engineered Human IgG Antibodies With Longer Serum Half-Lives in Primates," *J. Biol. Chem.* 279(8):6213-6216 (Feb. 20, 2004).
Holliger et al. "Diabodies": Small Bivalent and Bispecific Antibody Fragments, *Proc. Natl. Acad. Sci. USA* 90:6444-6448 (Jul. 1993).

(56) References Cited

OTHER PUBLICATIONS

Hongo et al. "Development and Characterization of Murine Monoclonal Antibodies to the Latency-Associated Peptide of Transforming Growth Factor β₁," *Hybridoma* 14(3):253-260 (1995).
Hoogenboom et al. "By-Passing Immunisation: Human Antibodies From Synthetic Repertoires of Germline V$_H$ Gene Segments Rearranged in Vitro," *J. Mol. Biol.* 227:381-388 (1992).
Hurle et al. "Protein Engineering Techniques for Antibody Humanization," *Curr. Op. Biotech.* 5:428-433 (1994).
Hwu. "Targeted Therapy for Metastatic Melanoma: From Bench to Bedside," *HemOncToday* (Jun. 25, 2010). Located at <http:www.healio.com/hematology-oncology/melanoma-skin-cancer/news/print/hematolo . . . >, last visited May 14, 2014, 4 pages.
Jackson et al. "In Vitro Antibody Maturation. Improvement of a High Affinity, Neutralizing Antibody Against IL-1 β," *J. Immunol.* 154(7):3310-3319 (1995).
Jakobovits et al. "Germ-Line Transmission and Expression of a Human-Derived Yeast Artificial Chromosome," *Nature* 362:255-258 (Mar. 18, 1993).
Jakobovits et al. "Analysis of Homozygous Mutant Chimeric Mice: Deletion of the Immunoglobulin Heavy-Chain Joining Region Blocks B-Cell Development and Antibody Production," *Proc. Natl. Acad. Sci USA* 90:2551-2555 (Mar. 1993).
Jenkins et al. "Antigen Presentation by Chemically Modified Splenocytes Induces Antigen-Specific T Cell Unreponsiveness in Vitro and in Vivo," *J. Exp. Med.* 165:302-319 (Feb. 1, 1987).
Jin et al. "Role of PD-1 in Regulating T-cell Immunity," *Current Topics in Microbiology and Immunology* 350:17-37 (2011).
Johnson et al. "The Kabat Database and a Bioinformatics Example," Chapter 2 in *Methods in Moleclular Biology*, Lo ed, Human Press, Totowa, NJ, vol. 284, pp. 11-25 (2003).
Jones et al. "Replacing the Complementarity-Determining Regions in a Human Antibody With Those From a Mouse," *Nature* 321:522-525 (May 29, 1986).
Kang et al. "Linkage of Recognition and Replication Functions by Assembling Combinatorial Antibody Fab Libraries Along Phage Surfaces," *Proc. Natl. Acad. Sci. USA* 88:4363-4366 (May 1991).
Keir et al. "PD-1 and Its Ligands in Tolerance and Immunity," *Annu. Rev. Immunol.* 26:677-704 (2008, e-pub. Jan. 2, 2008).
Kim et al. "Localization of the Site of the Murine IgG1 Molecule That is Involved in Binding to the Murine Intestinal Fc Receptor," *J. Immunol.* 24:2429-2434 (1994).
Köhler et al. "Continuous Cultures of Fused Cells Secreting Antibody of Predefined Specificity," *Nature* 256:495-497 (Aug. 7, 1975).
Lafferty et al. "A New Analysis of Allogeneic Interactions," *Aust. J. Exp. Biol. Med. Sci.* 53(pt. 1):27-42 (1975).
Lee et al. "High-Affinity Human Antibodies From Phage-Displayed Synthetic Fab Libraries With a Single Framework Scaffold," *J. Mol. Biol.* 340(5):1073-1093 (2004).
Lee et al. "Bivalent Antibody Phage Display Mimics Natural Immunoglobulin," *J. Immunol. Methods* 284(1-2):119-132 (2004).
Lenschow et al. "CD28/B7 System of T Cell Costimulation," *Ann. Rev. Immunol.* 14:233-258 (1996).
Li et al. "Human Antibodies for Immunotherapy Development Generated via a Human B Cell Hybridoma Technology," *Proc. Natl. Acad. Sci USA* 103(10):3557-3562 (Mar. 7, 2006).
Lonberg et al. "Antigen-Specific Human Antibodies From Mice Comprising Four Distinct Genetic Modifications," *Nature* 368:856-859 (Apr. 28, 1994).
Lonberg et al. "Human Antibodies From Transgenic Mice," *Inter. Rev. Immunol.* 13:65-93 (1995).
Lowman et al. "Selecting High-Affinity Binding Proteins by Monovalent Phage Display," *Biochemistry* 30(45):10832-10838 (1991).
Marks et al. "By-Passing Immunization. Human Antibodies From V-Gene Libraries Displayed on Phage," *J. Mol. Biol.* 222:581-597 (1991).
Marks et al. "By-Passing Immunization: Building High Affinity Human Antibodies by Chain Shuffling," *Bio/Technology* 10:779-783 (Jul. 1992).

Morrison. "Success in Specification," *Nature* 368:812-813 (Apr. 28, 1994).
Morrison et al. "Chimeric Human Antibody Molecules: Mouse Antigen-Binding Domains With Human Constant Region Domains," *Proc. Natl. Acad. Sci. USA* 81:6851-6855 (Nov. 1984).
Neuberger. "Generating High-Avidity Human Mabs in Mice," *Nature Biotechnol.* 14:826 (Jul. 1996).
Nicolaou et al. "Calicheamicin θ₁ⁱ: A Rationally Designed Molecule with Extremely Potent and Selective DNA Cleaving Properties and Apoptosis Inducing Activity," *Angew. Chem Intl. Ed. Engl.* 33(2):183-186 (1994).
Nomi, T. et al. "Clinical Significance and Therapeutic Potential of the Programmed Death-1 Ligand/Programmed Death-1 Pathway in Human Pancreatic Cancer," *Clinical Cancer Research, The American Association for Cancer Research* 13(7):2151-2157 (Apr. 1, 2007).
Okazaki et al. "Granulocyte Colony-Stimulating Facor Promotes Tumor Angiogenesis via Increasing Circulating Endothelial Progenitor Cells and Gr1+GD11b+ Cells in Cancer Animal Models," *Intern. Immun.* 18(1):1-9 (2005, e-pub. Dec. 13, 2005).
Pluckthun. "Antibodies From *Escherichia coli*," Chapter 11 in *The Pharmacology of Monoclonal Antibodies*, vol. 113, Rosenburg and Moore eds., Springer-Verlag, New York, pp. 269-315 (1994).
Presta. "Antibody Engineering," *Curr. Op. Sturct. Biol.* 2:593-596 (1992).
Ravetch et al. "FC Receptors," *Annu. Rev. Immunol.* 9:457-492 (1991).
Riechmann et al. "Reshaping Human Antibodies for Therapy," *Nature* 332:323-327 (Mar. 24, 1988).
Schier et al. "Identification of Functional and Structural Amino-Acid Residues by Parsimonious Mutagenesis," *Gene* 169:147-155 (1996).
Schoofs et al. "Epitopes of an Influenza Viral Peptide Recognized by Antibody at Single Amino Acid Resolution," *J. Immunol.* 140(2):611-616 (Jan. 15, 1988).
Sharpe et al. "The B7-CD28 Superfamily," *Nat. Rev.* 2:116-126 (Feb. 2002).
Sheriff et al. "Redefining the Minimal Antigen-Binding Fragment," *Nature Struct. Biol.* 3(9):733-736 (Sep. 1996).
Shields et al. "High Resolution Mapping of the Binding Site on Human IgG1 for FcγRI, FcγRII, FcγRIII, and FcRn and Design of IgG1 Variants With Improved Binding to the FcγR," *J. Biol. Chem.* 276(9):6591-6604 (Mar. 2, 2001).
Sidhu et al. "Phage-Displayed Antibody Libraries of Synthetic Heavy Chain Complementarity Determining Regions," *J. Mol. Biol.* 338(2):299-310 (2004).
Smith. Surface Presentation of Protein Epitopes Using Bacteriophage Expression Systems, *Current Opin. Biotechnol.* 2:668-673 (1991).
Stite, et al. "Immunoglobulin Proteins," Chapter 6 in *Basic and Clincial Immunology*, 8th Edition, Appleton & Lange, Norwalk, CT, pp. 66-79 (1994).
Thompson et al. "Tumor B7-H1 is Associated With Poor Prognosis in Renal Cell Carcinoma Patients With Long-Term Follow-Up," *Cancer Res* 66(7):3381-3385 (Apr. 1, 2006).
Van Dijk et al. "Human Antibodies as Next Generation Therapeutics," *Current Opinion in Chemical Biolology* 5:368-374 (2001).
Vaswani et al. "Humanizied Antibodies as Potential Therapeutic Drugs," *Ann. Allergy, Asthma & Immunol.* 81:105-119 (Aug. 1998).
Xu et al. "Diversity in the CdR3 Region of V$_H$ is Sufficient for Most Antibody Specificities," *Immunity* 13:37-45 (Jul. 2000).
Yamakawa et al. "The Dipole Moments of Some Heptafulvene Derivatives," *J. Am. Chem. Soc.* 82:5665-5667 (Nov. 5, 1960).
Yelton et al. "Affinity Maturation of the BR96 Anti-Carcinoma Antibody by Codon-Based Mutagenesis," *J. Immunol.* 155:1994-2004 (1995).
Zapata et al. "Engineering Linear F9ab')₂ Fragments for Efficient Production in *Escherichia coli* and Enhanced Antiproliferative Activity," *Protein Eng.* 8(10):1057-1062 (1995).
International Search Report mailed on Nov. 6, 2012, for PCT Application No. PCT/US2012/049233, filed on Aug. 1, 2012, 7 pages.

(56) References Cited

OTHER PUBLICATIONS

Written Opinion mailed on Nov. 6, 2012, for PCT Application No. PCT/US2012/049233, filed on Aug. 1, 2012, 9 pages.
Guan et al., "BRAF Gene Mutations in Colorectal Cancer," *Journal of Clinical and Experimental Pathology* 26(3):356-359, (Jun. 2010). (English Translation of the Abstract Only.).
Liu et al. "Plasma Cells From Multiple Myeloma Patients Express B7-H1 (PD-L1) and Increase Expression After Stimulation with IFN-γ and TLR Ligands via a MyD88-TRAF6, and MEK-Dependent Pathway," *Blood* 110(1):296-304, (Jul. 2007).
U.S. Appl. No. 14/825,779, filed Aug. 13, 2015, entitled "Methods of Using Anti-PD-L1 Antibodies and Their Use to Enhance T-Cell Function to Treat Tumor Immunity," by inventor "Irving et al."
U.S. Appl. No. 15/335,278, filed Oct. 26, 2016, entitled "Methods of Using Anti-PD-L1 Antibodies and Their Use to Enhance T-Cell Function to Treat Tumor Immunity," by inventor "Irving et al."

\* cited by examiner

Control: TTP5X = 6.5 days, 0% TGI, 0% PR
anti-PD-L1: TTP5X = 12 days, 60% TGI, 0% PR
G02443714: TTP5X = 14 days, 75% TGI, 0% PR
anti-PD-L1 + G02443714: TTP5x = 18 days, 85% TGI, 20% PR

SEQUENCE LISTING

```
<160> NUMBER OF SEQ ID NOS: 27

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asp or Gly

<400> SEQUENCE: 1

Gly Phe Thr Phe Ser Xaa Ser Trp Ile His
 1               5                  10

<210> SEQ ID NO 2
<211> LENGTH: 18
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Leu
<220> FEATURE:
<221> NAME/KEY: VARIANT
<222> LOCATION: 10
<223> OTHER INFORMATION: Xaa = Thr or Ser

<400> SEQUENCE: 2

Ala Trp Ile Xaa Pro Tyr Gly Gly Ser Xaa Tyr Tyr Ala Asp Ser Val
 1               5                  10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Arg His Trp Pro Gly Gly Phe Asp Tyr
 1               5

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser
            20                  25

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Trp Val Arg Gln Ala Pro Gly Lys Gly Leu Glu Trp Val
 1               5                  10

<210> SEQ ID NO 6
<211> LENGTH: 32
<212> TYPE: PRT
<213> ORGANISM: Artificial Sequence
<220> FEATURE:
<223> OTHER INFORMATION: Synthetic Construct

<400> SEQUENCE: 6

Arg Phe Thr Ile Ser Ala Asp Thr Ser Lys Asn Thr Ala Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 7
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 7

Trp Gly Gln Gly Thr Leu Val Thr Val Ser Ala
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Asp or Val
<220> FEATURE:
<221> NAME/KEY: VARIANT
<222> LOCATION: 6
<223> OTHER INFORMATION: Xaa = Val or Ile
<220> FEATURE:
<221> NAME/KEY: VARIANT
<222> LOCATION: 7
<223> OTHER INFORMATION: Xaa = Ser or Asn
<220> FEATURE:
<221> NAME/KEY: VARIANT
<222> LOCATION: 9
<223> OTHER INFORMATION: Xaa = Ala or Phe
<220> FEATURE:
<221> NAME/KEY: VARIANT
<222> LOCATION: 10
<223> OTHER INFORMATION: Xaa = Val or Leu

<400> SEQUENCE: 8

Arg Ala Ser Gln Xaa Xaa Xaa Thr Xaa Xaa Ala
 1               5                  10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Phe or Thr
<220> FEATURE:
<221> NAME/KEY: VARIANT
<222> LOCATION: 6
<223> OTHER INFORMATION: Xaa = Tyr or Ala

<400> SEQUENCE: 9

Ser Ala Ser Xaa Leu Xaa Ser
 1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Tyr, Gly, Phe or Ser
<220> FEATURE:
<221> NAME/KEY: VARIANT
<222> LOCATION: 4
<223> OTHER INFORMATION: Xaa = Leu, Tyr, Phe or Trp
```

```
<220> FEATURE:
<221> NAME/KEY: VARIANT
<222> LOCATION: 5
<223> OTHER INFORMATION: Xaa = Tyr, Asn, Ala, Thr, Gly, Phe or Ile
<220> FEATURE:
<221> NAME/KEY: VARIANT
<222> LOCATION: 6
<223> OTHER INFORMATION: Xaa = His, Val, Pro, Thr or Ile
<220> FEATURE:
<221> NAME/KEY: VARIANT
<222> LOCATION: 8
<223> OTHER INFORMATION: Xaa = Ala, Trp, Arg, Pro or Thr

<400> SEQUENCE: 10

Gln Gln Xaa Xaa Xaa Xaa Pro Xaa Thr
 1               5

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ser Ser Leu Ser Ala Ser Val Gly
 1               5                  10                  15

Asp Arg Val Thr Ile Thr Cys
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Trp Tyr Gln Gln Lys Pro Gly Lys Ala Pro Lys Leu Leu Ile Tyr
 1               5                  10                  15

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct

<400> SEQUENCE: 13

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Phe Gly Gln Gly Thr Lys Val Glu Ile Lys Arg
 1               5                  10

<210> SEQ ID NO 15
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 15

Gly Phe Thr Phe Ser Asp Ser Trp Ile His
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Synthetic Construct

<400> SEQUENCE: 16

Ala Trp Ile Ser Pro Tyr Gly Gly Ser Thr Tyr Tyr Ala Asp Ser Val
1               5                   10                  15

Lys Gly

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

Arg Ala Ser Gln Asp Val Ser Thr Ala Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Ser Ala Ser Phe Leu Tyr Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Gln Gln Tyr Leu Tyr His Pro Ala Thr
1               5

<210> SEQ ID NO 20
<211> LENGTH: 118
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30
```

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                    100                 105                 110

Leu Val Thr Val Ser Ala
            115

<210> SEQ ID NO 21
<211> LENGTH: 108
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 22
<211> LENGTH: 440
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser

```
            100                 105                 110
Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 23
<211> LENGTH: 214
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                20                  25                  30
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 118
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 25
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 25

Trp Gly Gln Gly Thr Leu Val Thr Val Ser Ser
1               5                   10

<210> SEQ ID NO 26
<211> LENGTH: 448
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 27
<211> LENGTH: 214
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

METHODS OF TREATING CANCER USING PD-1 AXIS BINDING ANTAGONISTS AND MEK INHIBITORS

CROSS REFERENCE TO RELATED APPLICATIONS

This application is a U.S. national phase patent application of PCT/US2012/049233, filed Aug. 1, 2012, which claims the priority benefit of U.S. provisional application Ser. No. 61/574,406, filed Aug. 1, 2011, the contents of which applications are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392010100SEQLIST.txt, date recorded: Jan. 29, 2014, size: 21 KB).

BACKGROUND OF THE INVENTION

The provision of two distinct signals to T-cells is a widely accepted model for lymphocyte activation of resting T lymphocytes by antigen-presenting cells (APCs). Lafferty et al, Aust. J. Exp. Biol. Med. ScL 53: 27-42 (1975). This model further provides for the discrimination of self from non-self and immune tolerance. Bretscher et al, Science 169: 1042-1049 (1970); Bretscher, P. A., P.N.A.S. USA 96: 185-190 (1999); Jenkins et al, J. Exp. Med. 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. Lenschow et al., Ann. Rev. Immunol. 14:233 (1996). In the absence of co-stimulation, T-cells can become refractory to antigen stimulation, do not mount an effective immune response, and further may result in exhaustion or tolerance to foreign antigens.

In the two-signal model T-cells receive both positive and negative secondary co-stimulatory signals. The regulation of such positive and negative signals is critical to maximize the host's protective immune responses, while maintaining immune tolerance and preventing autoimmunity. Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells. The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting of PD-1 and other molecules which signal through interactions with PD-1, such as programmed death ligand 1 (PD-L1) and programmed death ligand 2 (PD-L2) are an area of intense interest.

PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction may enhance CD8+ T cell-mediated killing of tumors.

The inhibition of PD-1 axis signaling through its direct ligands (e.g., PD-L1, PD-L2) has been proposed as a means to enhance T cell immunity for the treatment of cancer (e.g., tumor immunity). Moreover, similar enhancements to T cell immunity have been observed by inhibiting the binding of PD-L1 to the binding partner B7-1. Furthermore, combining inhibition of PD-1 signaling with other signaling pathways (e.g. MAPK pathway, "MEK") that are deregulated in tumor cells may further enhance treatment efficacy. However, an optimal therapeutic treatment would combine blockade of PD-1 receptor/ligand interaction with an agent that directly inhibited tumor growth, optionally further including unique immune enhancing properties not provided by PD-1 blockade alone. There remains a need for such an optimal therapy for treating, stabilizing, preventing, and/or delaying development of various cancers.

All references, publications, and patent applications disclosed herein are hereby incorporated by reference in their entirety.

BRIEF SUMMARY OF THE INVENTION

The present invention describes a combination treatment comprising a MEK inhibitor (which has direct tumor targeted effects and immune enhancing properties) and a PD-1 axis binding antagonist.

Provided herein are methods for treating cancer or slowing progression of cancer in an individual comprising administering to the individual an effective amount of a PD-1 axis binding antagonist and a MEK inhibitor.

Also provided herein is use of a PD-1 axis binding antagonist in the manufacture of a medicament for treating or delaying progression of cancer in an individual in combination with a MEK inhibitor. Also provided herein is use of a MEK inhibitor in the manufacture of a medicament for treating or delaying progression of cancer in an individual in combination with a PD-1 axis binding antagonist. Also provided herein is use of a PD-1 axis binding antagonist and a MEK inhibitor in the manufacture of medicaments for treating or delaying progression of cancer in an individual. Also provided herein is a manufacturing process of medicaments for treating or delaying progression of cancer in an individual, characterized by the use of a PD-1 axis binding antagonist and a MEK inhibitor. Also provided herein is a PD-1 axis binding antagonist for use in combination with a MEK inhibitor for treating or delaying progression of cancer in the individual. Also provided herein is a MEK inhibitor for use in combination with a PD-1 axis binding antagonist for treating or delaying progression of cancer in the individual.

The cancer treated may contain a BRAF V600E mutation, a BRAF wildtype, a KRAS wildtype, or an activating KRAS mutation. The cancer may be a melanoma, a colorectal cancer, a non-small cell lung cancer, an ovarian cancer, a breast cancer, a prostate cancer, a pancreatic cancer, hematological malignancy or a renal cell carcinoma. The cancer may be at early stage or at late stage. In some embodiments, the individual treated is a human.

In some embodiments, the treatment results in sustained response in the individual after cessation of the treatment. In some embodiments, the treatment produces a complete response, a partial response, or stable disease in the individual.

Also provided herein are methods of enhancing immune function in an individual having cancer comprising administering an effective amount of a PD-1 axis binding antagonist and a MEK inhibitor. In some embodiments, the individual is a human.

Also provided herein is use of a PD-1 axis binding antagonist in the manufacture of a medicament for enhancing immune function in an individual having cancer in combination with a MEK inhibitor. Also provided herein is use of a MEK inhibitor in the manufacture of a medicament for enhancing immune function in an individual having cancer in combination with a PD-1 axis binding antagonist. Also provided herein is use of a PD-1 axis binding antagonist and a MEK inhibitor in the manufacture of medicaments for enhancing immune function in the individual having cancer. Also provided herein is a manufacturing process of medicaments for enhancing immune function in an individual, characterized by the use of a PD-1 axis binding antagonist and a MEK inhibitor. Also provided herein is a PD-1 axis binding antagonist for use in combination with a MEK inhibitor for enhancing immune function in the individual having cancer. Also provided herein is a MEK inhibitor for use in combination with a PD-1 axis binding antagonist for enhancing immune function in the individual having cancer. In some embodiments, the individual is a human.

In some embodiments, the PD-1 axis binding antagonist is a PD-1 binding antagonist, a PD-L1 binding antagonist or a PD-L2 binding antagonist. In some embodiments, the PD-1 binding antagonist inhibits binding of PD-1 to PD-L1 and/or binding of PD-1 to PD-L2. In some embodiments, the PD-1 binding antagonist is an antibody (e.g., antibody MDX-1106, CT-011 and Merck 3745 described herein), an antigen binding fragments thereof, an immunoadhesin, a fusion protein, or an oligopeptide. In some embodiments, the PD-1 binding antagonist is an immunoadhesin comprising a PD-L2 extracellular domain fused to a Fc domain (e.g., AMP-224 described herein). In some embodiments, the PD-L1 binding antagonist inhibits binding of PD-L1 to PD-1 and/or binding of PD-L1 to B7-1. In some embodiments, the PD-L1 binding antagonist is an antibody (e.g., antibody YW243.55.S70, MPDL3280A and MDX-1105 described herein), an antigen binding fragments thereof, an immunoadhesin, a fusion protein, or an oligopeptide. In some embodiments, the PD-L2 binding antagonist inhibits binding of PD-L2 to PD-1. In some embodiments, the PD-L2 binding antagonist is an antibody, an antigen binding fragments thereof, an immunoadhesin, a fusion protein, or an oligopeptide.

In some embodiments, the MEK inhibitor is a compound of the formula (I), (II), (III), (IV), (V), or (VI) as described here below, or a pharmaceutically acceptable salt or solvate thereof.

In some embodiments, the MEK inhibitor is a competitive inhibitor of MEK. In some embodiments, the MEK inhibitor is more selective against activating KRAS mutation. In some embodiments, the MEK inhibitor is an allosteric inhibitor of MEK. In some embodiments, the MEK inhibitor is more selective against an activating BRAF mutation. In some embodiments, the MEK inhibitor is selected from the group consisting of G02442104, G-38963, G02443714, G00039805, and GDC-0973, or a pharmaceutically acceptable salt or solvate thereof.

In some embodiments, the MEK inhibitor is administered continuously or intermittently. In some embodiments, the MEK inhibitor is administered before administration of the PD-1 axis binding antagonist, simultaneously with administration of the PD-1 axis binding antagonist, or after administration of the PD-1 axis binding antagonist. In some embodiments, the MEK inhibitor and the PD-1 axis binding antagonist are administered with different dosing frequency.

In another aspect, provided is a kit comprising a PD-1 axis binding antagonist and/or a MEK inhibitor for treating or delaying progression of a cancer in an individual or enhancing immune function in an individual having cancer. The kit may comprise a PD-1 axis binding antagonist and a package insert comprising instructions for using the PD-1 axis binding antagonist in combination with a MEK inhibitor to treat or delay progression of cancer in an individual, or enhancing immune function in an individual having cancer. The kit may comprise a MEK inhibitor and a package insert comprising instructions for using the MEK inhibitor in combination with a PD-1 axis binding antagonist to treat or delay progression of cancer in an individual, or to enhance immune function in an individual having cancer. The kit may comprise a PD-1 axis binding antagonist and a MEK inhibitor, and a package insert comprising instructions for using the PD-1 axis binding antagonist and the MEK inhibitor to treat or delay progression of cancer in an individual, or to enhance immune function in an individual having cancer.

DETAILED DESCRIPTION OF THE INVENTION

I. General Techniques

Figure 1:
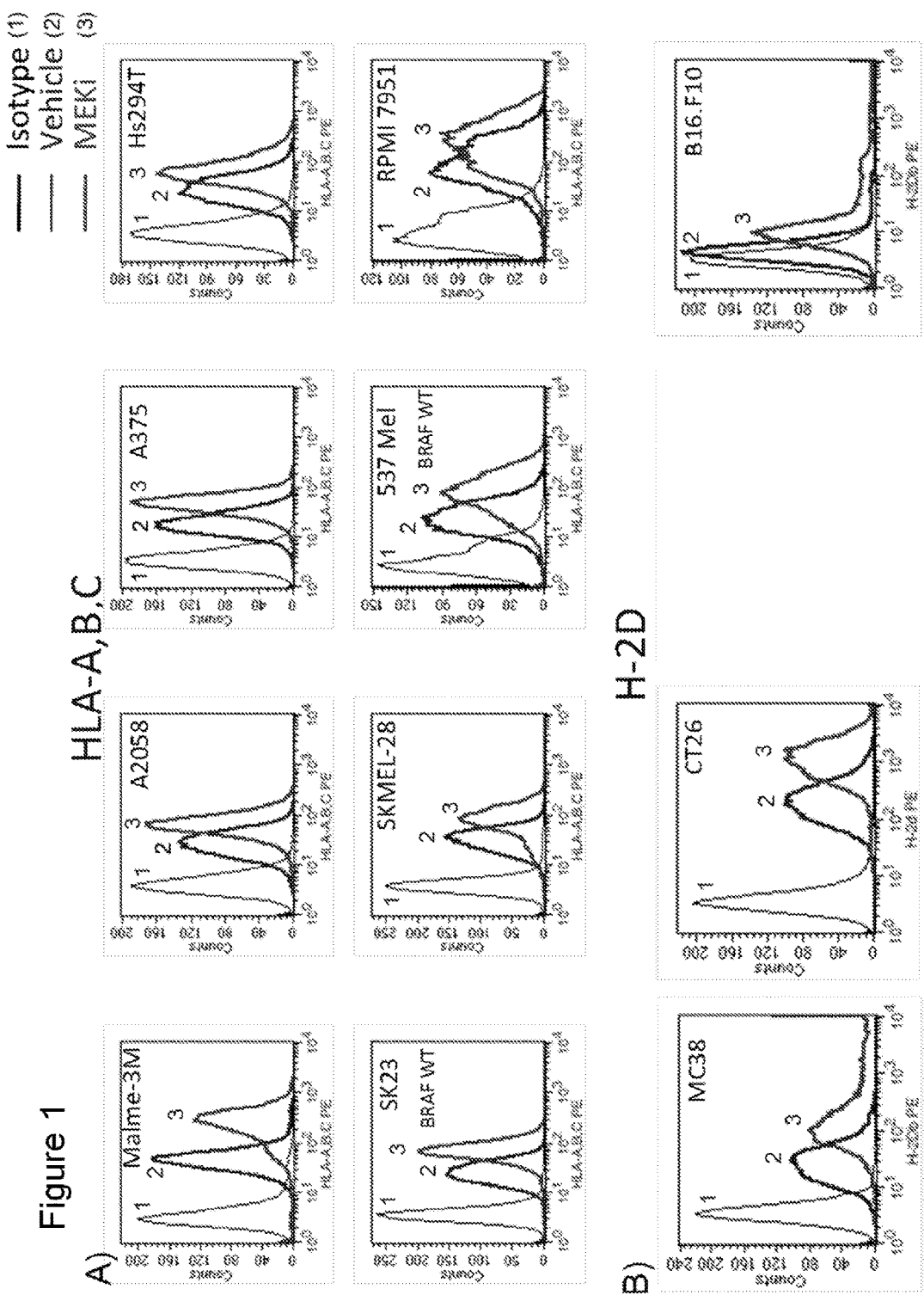
FIG. 1 shows enhanced MHC I surface expression on melanoma and colorectal tumor cell lines upon treatment with MEK inhibitor. (A) Histogram showing increased MHC I expression on the surface of human tumor cell lines treated with MEK inhibitor. (B) Histogram showing increased MHC I expression on the surface of mouse tumor cell lines treated with MEK inhibitor.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: A Practical Approach (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); PCR: *The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C.

Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and Cancer: *Principles and Practice of Oncology* (V. T. DeVita et al., eds., J. B. Lippincott Company, 1993).

II. Definitions

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiVeness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenecity" refers to the ability of a particular substance to provoke an immune response. Tumors are immunogenic and enhancing tumor immunogenicity aids in the clearance of the tumor cells by the immune response. Examples of enhancing tumor immunogenicity include treatment with anti-PDL antibodies and a MEK inhibitor.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for 1.1 and E isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., Nature, 256:495-97 (1975); Hongo et al., *Hybridoma*, 14 (3): 253-260 (1995), Harlow et al., *Antibodies: A Laboratory Manual*, (Cold Spring Harbor Laboratory Press, $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in i Methods in Molecular Biology 248: 1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available compleX crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVQLVES-GGGLVQPGGSLRLSCAAS (HC-FR1) (SEQ ID NO:4), WVRQAPGKGLEWV (HC-FR2), (SEQ ID NO:5), RFTI-SADTSKNTAYLQMNSLRAEDTAVYYCAR (HC-FR3, SEQ ID NO:6), WGQGTLVTVSA (HC-FR4), (SEQ ID NO:7).

A "VL kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSLSAS-VGDRVTITC (LC-FR1) (SEQ ID NO:11), WYQQKPG-KAPKLLIY (LC-FR2) (SEQ ID NO:12), GVPSRFSGSGS-GTDFTLTISSLQPEDFATYYC (LC-FR3) (SEQ ID NO:13), FGQGTKVEIKR (LC-FR4) (SEQ ID NO:14).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH— and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2 (including IgG2A and IgG2B), IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. For example, useful immunoadhesins as second medicaments useful for combination therapy herein include polypeptides that comprise the extracellular or PD-1 binding portions of PD-L1 or PD-L2 or the extracellular or PD-L1 or PD-L2 binding portions of PD-1, fused to a constant domain of an immunoglobulin sequence, such as a PD-L1 ECD Fc, a PD-L2 ECD Fc, and a PD-1 ECD-Fc, respectively.

Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, etc. The two portions may be linked directly by a single peptide bond or through a peptide linker but are in reading frame with each other.

A "PD-1 oligopeptide," "PD-L1 oligopeptide," or "PD-L2 oligopeptide" is an oligopeptide that binds, preferably specifically, to a PD-1, PD-L1 or PD-L2 negative costimulatory polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. USA.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *I Immunol. Meth.*, 102:259-274 (1987); Schoofs et al., *J. Immunol.*, 140:611-616 (1988), Cwirla, S. E. et al. *Proc. Natl. Acad. Sci. USA*, 87:6378 (1990); Lowman, H. B. et al. *Biochemistry*, 30:10832 (1991); Clackson, T. et al. *Nature*, 352: 624 (1991); Marks, J. D. et al., *J. Mol. Biol.*, 222:581 (1991); Kang, A. S. et al. *Proc. Natl. Acad. Sci. USA*, 88:8363 (1991), and Smith, G. P., *Current Opin. Biotechnol.*, 2:668 (1991).

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-PD-L1 antibodies of the invention block the signaling through PD-1 so as to restore a functional response by T-cells (e.g., proliferation, cytokine production, target cell killing) from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin;

nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Nicolaou et al., Angew. Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL8), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

The term "alkyl" as used herein refers to a saturated linear or branched-chain monovalent hydrocarbon radical of one to twelve carbon atoms. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH) propynyl (propargyl, —$CH_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco [3.1.0]hexanyl, 3-azabicyclo[4.1.0]heptanyl, and azabicyclo [2.2.2]hexanyl. Spiro moieties are also included within the scope of this definition. Examples of a heterocyclic group wherein ring atoms are substituted with oxo (═O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The heteroatoms present in heteroaryl or heterocyclcyl include the oxidized forms such as $N^+ \rightarrow O^-$, $S(O)$ and $S(O)_2$.

The term "halo" refers to F, Cl, Br or I.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid; such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid; and ethanolamine. The term "hydrate" refers to the complex where the solvent molecule is water.

It is understood that aspects and variations of the invention described herein include "consisting of" and/or "consisting essentially of" aspects and variations.

III Methods

In one aspect, provided herein is a method for treating or delaying progression of cancer in an individual comprising administering to the individual an effective amount of a PD-1 axis binding antagonist and a MEK inhibitor. In some embodiments, the treatment results in sustained response in the individual after cessation of the treatment.

The methods of this invention may find use in treating conditions where enhanced immunogenicity is desired such as increasing tumor immunogenicity for the treatment of cancer. A variety of cancers may be treated, or their progression may be delayed, including but are not limited to a cancer that may contain a BRAF V600E mutation, a cancer that may contain a BRAF wildtype, a cancer that may contain a KRAS wildtype, or a cancer that may contain an activating KRAS mutation.

In some embodiments, the individual has melanoma. The melanoma may be at early stage or at late stage. In some embodiments, the individual has colorectal cancer. The colorectal cancer may be at early stage or at late stage. In some embodiments, the individual has non-small cell lung cancer. The non-small cell lung cancer may be at early stage or at late stage. In some emodiements, the individual has pancreatic cancer. The pancreatice cancer may be at early stage or late state. In some embodiments, the individual has a hematological malignancy. The hematological malignancy may be early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has renal cell carcinoma. The renal cell carcinoma may be at early stage or at late stage.

In some embodiments, the individual is a mammal, such as domesticated animals (e.g., cows, sheep, cats, dogs, and horses), primates (e.g., humans and non-human primates such as monkeys), rabbits, and rodents (e.g., mice and rats). In some embodiments, the individual treated is a human.

In another aspect, provided herein is a method of enhancing immune function in an individual having cancer comprising administering an effective amount of a PD-1 axis binding antagonist and a MEK inhibitor.

In some embodiments, the CD8 T cells in the individual have enhanced priming, activation, proliferation and/or cytolytic activity relative to prior to the administration of the PD-1 pathway antagonist and the MEK inhibitor. In some embodiments, the CD8 T cell priming is characterized by elevated CD44 expression and/or enhanced cytolytic activity in CD8 T cells. In some embodiments, the CD8 T cell activation is characterized by an elevated frequency of γ-IFN+ CD8 T cells. In some embodiments, the CD8 T cell is an antigen-specific T-cell. In some embodiments, the immune evasion by signaling through PD-L1 surface expression is inhibited.

In some embodiments, the cancer cells in the individual have elevated expression of MHC class I antigen expression relative to prior to the administration of the PD-1 pathway antagonist and the MEK inhibitor.

In some embodiment's, the antigen presenting cells in the individual have enhanced maturation and activation relative prior to the administration of the PD-1 pathway antagonist and the MEK inhibitor. In some embodiments, wherein the antigen presenting cells are dendritic cells. In some embodiments, the maturation of the antigen presenting cells is characterized by increased frequency of CD83+ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the individual are reduced relative prior to the administration of the anti-PD-L1 antibody and the MEK inhibitor.

In some embodiments, the cancer has elevated levels of T-cell infiltration.

In some embodiments, the combination therapy of the invention comprises administration of a PD-1 axis binding antagonist and a MEK inhibitor. The PD-1 axis binding antagonist and the MEK inhibitor may be administered in any suitable manner known in the art. For example, The PD-1 axis binding antagonist and the MEK inhibitor may be administered sequentially (at different times) or concurrently (at the same time).

In some embodiments, the MEK inhibitor is administered continuously. In some embodiments, the MEK inhibitor is administered intermittently. In some embodiments, the MEK inhibitor is administered before administration of the PD-1 axis binding antagonist. In some embodiments, the MEK inhibitor is administered simultaneously with administration of the PD-1 axis binding antagonist. In some embodiments, the MEK inhibitor is administered after administration of the PD-1 axis binding antagonist.

In some embodiments, provided is a method for treating or delaying progression of cancer in an individual comprising administering to the individual an effective amount of a PD-1 axis binding antagonist and a MEK inhibitor, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PI3K/AKT/mTOR pathway, HSP90 inhibitor, tubulin inhibitor, apoptosis inhibitor, and/or chemopreventative agent. The additional therapy may be one or more of the chemotherapeutic agents described hereabove.

The PD-1 axis binding antagonist and the MEK inhibitor may be administered by the same route of administration or by different routes of administration. In some embodiments, the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally. In some embodiments, the MEK inhibitor is administered intravenously, intramuscularly, subcutaneously, topically, orally, transdermally, intraperitoneally, intraorbitally, by implantation, by inhalation, intrathecally, intraventricularly, or intranasally. An effective amount of the PD-1 axis binding antagonist and the MEK inhibitor may be administered for prevention or treatment of disease. The appropriate dosage of the PD-1 axis binding antagonist and/or the MEK inhibitor may be deterimined based on the type of disease to be treated, the type of the PD-1 axis binding antagonist and the MEK inhibitor, the severity and course of the disease, the clinical condition of the individual, the individual's clinical history and response to the treatment, and the discretion of the attending physician.

Any of the PD-1 axis binding antagonists and the MEK inhibitors known in the art or described below may be used in the methods.

PD-1 Axis Binding Antagonists

Provided herein is a method for treating or delaying progression of cancer in an individual comprising administering to the individual an effective amount of a PD-1 axis binding antagonist and a MEK inhibitor. For example, a PD-1 axis binding antagonist includes a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide.

In some embodiment, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106, Merck 3475 and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A and MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1106, also known as MDX-1106-04, ONO-4538 or BMS-936558, is an anti-PD-1 antibody described in WO2006/121168. Merck 3745, also known as MK-3475 or SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

In some embodiments, the anti-PD-1 antibody is MDX-1106. Alternative names for "MDX-1106" include MDX-1106-04, ONO-4538, BMS-936558 or Nivolumab. In some embodiments, the anti-PD-1 antibody is Nivolumab (CAS Registry Number: 946414-94-4). In a still further embodiment, provided is an isolated anti-PD-1 antibody comprising a heavy chain variable region comprising the heavy chain variable region amino acid sequence from SEQ ID NO:22 and/or a light chain variable region comprising the light chain variable region amino acid sequence from SEQ ID NO:23. In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody.

The anti-PD-L1 antibodies useful in this invention, including compositions containing such antibodies, such as those described in WO 2010/077634 A1, may be used in combination with a MEK inhibitor to treat cancer. In some embodiments, the anti-PD-L1 antibody comprises a heavy chain variable region comprising the amino acid sequence of SEQ ID NO:20 and a light chain variable region comprising the amino acid sequence of SEQ ID NO:21.

In one embodiment, the anti-PD-L1 antibody contains a heavy chain variable region polypeptide comprising an HVR-H1, HVR-H2 and HVR-H3 sequence, wherein:

(a) the HVR-H1 sequence is GFTFSX$_1$SWIH (SEQ ID NO:1);
(b) the HVR-H2 sequence is AWIX$_2$PYGGSX$_3$YYADSVKG (SEQ ID NO:2);
(c) the HVR-H3 sequence is RHWPGGFDY (SEQ ID NO:3);

further wherein: X$_1$ is D or G; X$_2$ is S or L; X$_3$ is T or S.

In one specific aspect, X$_1$ is D; X$_2$ is S and X$_3$ is T. In another aspect, the polypeptide further comprises variable region heavy chain framework sequences juxtaposed between the HVRs according to the formula: (HC-FR1)-

```
                                                    (SEQ ID NO: 22)
QVQLVESGGGVVQPGRSLRLDCKASGITFSNSGMHWVRQAPGKGLEWVAVIWY

DGSKRYYADSVKGRFTISRDNSKNTLFLQMNSLRAEDTAVYYCATNDDYWGQGTLVT

VSSASTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEELGG

PSVFLFPPKPKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFFLYSRLTVDK

SRWQEGNVFSCSVMHEALHNHYTQKSLSLSLGK,
or
```

(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup

```
                                                    (SEQ ID NO: 23)
EIVLTQSPATLSLSPGERATLSCRASQSVSSYLAWYQQKPGQAPRLLIYDASNRAT

GIPARFSGSGSGTDFTLTISSLEPEDFAVYYCQQSSNWPRTFGQGTKVEIKRTVAAPSVFI

FPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC.
```

Examples of anti-PD-L1 antibodies useful for the methods of this invention, and methods for making thereof are described in PCT patent application WO 2010/077634 A1, which is incorporated herein by reference.

In some embodiments, the PD-1 axis binding antagonist is an anti-PD-L1 antibody. In some embodiments, the anti- III consensus framework. In a still further aspect, at least one of the framework sequences is the following:

HC-FR1 is EVQLVESGGGLVQPGGSLRLSCAAS (SEQ ID NO:4)

HC-FR2 is WVRQAPGKGLEWV (SEQ ID NO:5)

HC-FR3 is RFTISADTSKNTAYLQMNSLRAED-TAVYYCAR (SEQ ID NO:6)

HC-FR4 is WGQGTLVTVSA (SEQ ID NO:7).

In a still further aspect, the heavy chain polypeptide is further combined with a variable region light chain comprising an HVR-L1, HVR-L2 and HVR-L3, wherein:

(a) the HVR-L1 sequence is RASQX$_4$X$_5$X$_6$TX$_7$X$_8$A (SEQ ID NO:8);

(b) the HVR-L2 sequence is SASX$_9$LX$_{10}$S, (SEQ ID NO:9);

(c) the HVR-L3 sequence is QQX$_{11}$X$_{12}$X$_{13}$X$_{14}$PX$_{15}$T (SEQ ID NO:10);

further wherein: X$_4$ is D or V; X$_5$ is V or I; X$_6$ is S or N; X$_7$ is A or F; X$_8$ is V or L; X$_9$ is F or T; X$_{10}$ is Y or A; X$_1$ is Y, G, F, or S; X$_{12}$ is L, Y, F or W; X$_{13}$ is Y, N, A, T, G, F or I; X$_{14}$ is H, V, P, T or I; X$_{15}$ is A, W, R, P or T.

In a still further aspect, X$_4$ is D; X$_5$ is V; X$_6$ is S; X$_7$ is A; X$_8$ is V; X$_9$ is F; X$_{10}$ is Y; X$_{11}$ is Y; X$_{12}$ is L; X$_{13}$ is Y; X$_{14}$ is H; X$_{15}$ is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

LC-FR1 is DIQMTQSPSSLSASVGDRVTITC (SEQ ID NO:11)

LC-FR2 is WYQQKPGKAPKLLIY (SEQ ID NO:12)

LC-FR3 is GVPSRFSGSGSGTDFTLTISSLQPEDFATYYC (SEQ ID NO:13)

LC-FR4 is FGQGTKVEIKR (SEQ ID NO:14).

In another embodiment, provided is an isolated anti-PD-L1 antibody or antigen binding fragment comprising a heavy chain and a light chain variable region sequence, wherein:

(a) the heavy chain comprises and HVR-1-H1, HVR-1-H2 and HVR-H3, wherein further:
  (i) the HVR-H1 sequence is GFTFSX$_1$SWIH; (SEQ ID NO:1)
  (ii) the HVR-H2 sequence is AWIX$_2$PYGGSX$_3$YYADSVKG (SEQ ID NO:2)
  (iii) the HVR-H3 sequence is RHWPGGFDY, and (SEQ ID NO:3)

(b) the light chain comprises and HVR-L1, HVR-L2 and HVR-L3, wherein further:
  (i) the HVR-L1 sequence is RASQX$_4$X$_5$X$_6$TX$_7$X$_8$A (SEQ ID NO:8)
  (ii) the HVR-L2 sequence is SASX$_9$LX$_{10}$S; and (SEQ ID NO:9)
  (iii) the HVR-L3 sequence is QQX$_{11}$X$_{12}$X$_{13}$X$_{14}$PX$_{15}$T; (SEQ ID NO:10)

Further wherein: X$_1$ is D or G; X$_2$ is S or L; X$_3$ is T or S; X$_4$ is D or V; X$_5$ is V or 1; X$_6$ is S or N; X$_7$ is A or F; X$_8$ is V or L; X$_9$ is F or T; X$_{10}$ is Y or A; X$_{11}$ is Y, G, F, or S; X$_{12}$ is L, Y, F or W; X$_{13}$ is Y, N, A, T, G, F or 1; X$_{14}$ is H, V, P, T or I; X$_{15}$ is A, W, R, P or T.

In a specific aspect, X$_1$ is D; X$_2$ is S and X$_3$ is T. In another aspect, X$_4$ is D; X$_5$ is V; X$_6$ is S; X$_7$ is A; X$_8$ is V; X$_9$ is F; X$_{10}$ is Y; X$_{11}$, is Y; X$_{12}$ is L; X$_{13}$ is Y; X$_{14}$ is H; X$_{15}$ is A. In yet another aspect, X$_1$ is D; X$_2$ is S and X$_3$ is T, X$_4$ is D; X$_5$ is V; X$_6$ is S; X$_7$ is A; X$_8$ is V; X$_9$ is F; X$_{10}$ is Y; X$_{11}$ is Y; X$_{12}$ is L; X$_{13}$ is Y; X$_{14}$ is H and X$_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                           (SEQ ID NO: 4)
HC-FR1  EVQLVESGGGLVQPGGSLRLSCAAS (SEQ ID NO: 5)
HC-FR2  WVRQAPGKGLEWV (SEQ ID NO: 6)
HC-FR3  RFTISADTSKNTAYLQMNSLRAEDTAVYYCAR (SEQ ID NO: 7)
HC-FR4  WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                           (SEQ ID NO: 11)
LC-FR1  DIQMTQSPSSLSASVGDRVTITC (SEQ ID NO: 12)
LC-FR2  WYQQKPGKAPKLLIY (SEQ ID NO: 13)
LC-FR3  GVPSRFSGSGSGTDFTLTISSLQPEDFATYYC (SEQ ID NO: 14)
LC-FR4  FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:

(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, or (b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(LC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                          (SEQ ID NO: 4)
HC-FR1 EVQLVESGGGLVQPGGSLRLSCAAS (SEQ ID NO: 5)
HC-FR2 WVRQAPGKGLEWV (SEQ ID NO: 6)
HC-FR3 RFTISADTSKNTAYLQMNSLRAEDTAVYYCAR (SEQ ID NO: 7)
HC-FR4 WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                          (SEQ ID NO: 11)
LC-FR1 DIQMTQSPSSLSASVGDRVTITC (SEQ ID NO: 12)
LC-FR2 WYQQKPGKAPKLLIY (SEQ ID NO: 13)
LC-FR3 GVPSRFSGSGSGTDFTLTISSLQPEDFATYYC (SEQ ID NO: 14)
LC-FR4 FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:

(a) the heavy chain sequence has at least 85% sequence identity to the heavy chain sequence: EVQLVESGGGLVQPGGSLRLSCAASGFTFSDSWIHWVRQAPGKGLEWVAWIS PYGGSTYYADSVKGRFTISADTSKNTAYLQMNSLRAEDTAVYYCARRHWPGGFDYWGQGTLVTVSA (SEQ ID NO:20), or (b) the light chain sequences has at least 85% sequence identity to the light chain sequence: DIQMTQSPSSLSASVGDRVTITCRASQDVSTAVAWYQQKPGKAPKLLIY SASF LYSGVPSRFSGSGSGTDFTLTISSLQPEDFATYYCQQYLYHPATFGQGTKVEIKR (SEQ ID NO:21).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                          (SEQ ID NO: 4)
HC-FR1 EVQLVESGGGLVQPGGSLRLSCAAS (SEQ ID NO: 5)
HC-FR2 WVRQAPGKGLEWV (SEQ ID NO: 6)
HC-FR3 RFTISADTSKNTAYLQMNSLRAEDTAVYYCAR (SEQ ID NO: 7)
HC-FR4 WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                          (SEQ ID NO: 11)
LC-FR1 DIQMTQSPSSLSASVGDRVTITC (SEQ ID NO: 12)
LC-FR2 WYQQKPGKAPKLLIY (SEQ ID NO: 13)
LC-FR3 GVPSRFSGSGSGTDFTLTISSLQPEDFATYYC (SEQ ID NO: 14)
LC-FR4 FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PD-L1 antibody comprising a heavy chain and a light chain variable region sequence, wherein:

(a) the heavy chain sequence has at least 85% sequence identity to the heavy chain sequence:EVQLVESGGGLVQPGGSLRLSCAASGFTFSDSWIHWVRQAPGKGLEWVAWIS PYGGSTYYADSVKGRFTISADTSKNTAYLQMNSLRAEDTAVYYCARRHWPGGFDYWG QGTLVTVSS (SEQ ID NO:24), or (b) the light chain sequences has at least 85% sequence identity to the light chain sequence: DIQMTQSPSSLSASVGDRVTITCRASQDVSTAVAWYQQKPGKAPKLLIY SASF LYSGVPSRFSGSGSGTDFTLTISSLQPEDFATYYCQQYLYHPATFGQGTKVEIKR (SEQ Ill NO:21).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                        (SEQ ID NO: 4)
HC-FR1  EVQLVESGGGLVQPGGSLRLSCAAS (SEQ ID NO: 5)
HC-FR2  WVRQAPGKGLEWV (SEQ ID NO: 6)
HC-FR3  RFTISADTSKNTAYLQMNSLRAEDTAVYYCAR
```

```
                                        (SEQ ID NO: 25)
HC-FR4  WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                        (SEQ ID NO: 11)
LC-FR1  DIQMTQSPSSLSASVGDRVTITC (SEQ ID NO: 12)
LC-FR2  WYQQKPGKAPKLLIY (SEQ ID NO: 13)
LC-FR3  GVPSRFSGSGSGTDFTLTISSLQPEDFATYYC (SEQ ID NO: 14)
LC-FR4  FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, the anti-PD-1 antibody is MPDL3280A. In a still further embodiment, provided is an isolated anti-PD-1 antibody comprising a heavy chain variable region comprising the heavy chain variable region amino acid sequence from SEQ ID NO:24 and/or a light chain variable region comprising the light chain variable region amino acid sequence from SEQ ID NO:25. In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                        (SEQ ID NO: 26)
EVQLVESGGGLVQPGGSLRLSCAASGFTFSDSWIHWVRQAPGKGLEWVAWISPYGGST

YYADSVKGRFTISADTSKNTAYLQMNSLRAEDTAVYYCARRHWPGGFDYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPR

EEQYASTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSK

LTVDKSRWQQGNVFSCSVMHEALHNHYTQKSLSLSPGK, or
```

(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 27)
DIQMTQSPSSLSASVGDRVTITCRASQDVSTAVAWYQQKPGKAPKLLIYSASFLYSGVPS

RFSGSGSGTDFTLTISSLQPEDFATYYCQQYLYHPATFGQGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC.

In a still further embodiment, the invention provides for compositions comprising any of the above described anti-PD-L1 antibodies in combination with at least one pharmaceutically-acceptable carrier.

In a still further embodiment, provided is an isolated nucleic acid encoding a light chain or a heavy chain variable region sequence of an anti-PD-L1 antibody, wherein:
(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, and
(b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYH-PAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

(SEQ ID NO: 4)
HC-FR1 EVQLVESGGGLVQPGGSLRLSCAAS (SEQ ID NO: 5)
HC-FR2 WVRQAPGKGLEWV (SEQ ID NO: 6)
HC-FR3 RFTISADTSKNTAYLQMNSLRAEDTAVYYCAR (SEQ ID NO: 7)
HC-FR4 WGQGTLVTVSA.

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

(SEQ ID NO: 11)
LC-FR1 DIQMTQSPSSLSASVGDRVTITC

-continued (SEQ ID NO: 12)
LC-FR2 WYQQKPGKAPKLLIY (SEQ ID NO: 13)
LC-FR3 GVPSRFSGSGSGTDFTLTISSLQPEDFATYYC (SEQ ID NO: 14)
LC-FR4 FGQGTKVEIKR.

In a still further specific aspect, the antibody described herein (such as an anti-PD-1 antibody, an anti-PD-L1 antibody, or an anti-PD-L2 antibody) further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, provided herein are nucleic acids encoding any of the antibodies described herein. In some embodiments, the nucleic acid further comprises a vector suitable for expression of the nucleic acid encoding any of the previously described anti-PD-L1, anti-PD-1, or anti-PD-L2 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The antibody or antigen binding fragment thereof, may be made using methods known in the art, for example, by a process comprising culturing a host cell containing nucleic acid encoding any of the previously described anti-PD-L1, anti-PD-1, or anti-PD-L2 antibodies or antigen-binding fragment in a form suitable for expression, under conditions suitable to produce such antibody or fragment, and recovering the antibody or fragment.

In a still further embodiment, the invention provides for a composition comprising an anti-PD-L1, an anti-PD-1, or an anti-PD-L2 antibody or antigen binding fragment thereof as provided herein and at least one pharmaceutically acceptable carrier. In some embodiments, the anti-PD-L1, anti-PD-1, or anti-PD-L2 antibody or antigen binding fragment thereof administered to the individual is a composition comprising one or more pharmaceutically acceptable carrier. Any of the pharmaceutically acceptable carrier described herein or known in the art may be used.

MEK Inhibitors

The invention provides methods for treating cancer or slowing progression of cancer in an individual comprising administering an effective amount of a PD-1 pathway antagonist and a MEK inhibitor. Any known MEK inhibitors are intended, such as the MEK inhibitor compounds described in PCT patent applications WO 03/077914 A1, WO 2005/121142 A1, WO 2007/044515 A1, WO 2008/024725 A1 and WO 2009/085983 A1, the content of which are incorporated herein by reference. The MEK inhibitor administered may be in a pharmaceutical composition or formulation. In some embodiments, the pharmaceutical composition or formulation comprises one or more MEK inhibitors described herein and a pharmaceutically acceptable carrier or excipient.

In some embodiments, the MEK inhibitor is a competitive inhibitor of MEK. In some embodiments, the MEK inhibitor is more selective against an activating KRAS mutation. In some embodiments, the MEK inhibitor is an allosteric inhibitor of MEK. In some embodiments, the MEK inhibitor is more selective against an activating BRAF mutation (e.g., BRAF V600E mutation). In some embodiments, the MEK inhibitor binds and inhibits the activity of MEK1 and/or MEK2 (such as human MEK1 and/or human MEK2).

In some embodiments, the MEK inhibitor is a compound selected from the group consisting of GDC-0973, G-38963, G02443714 (also known as "AS703206"), G02442104 (also known as "GSK-1120212"), and G00039805 (also known as "AZD-6244"), or a pharmaceutically acceptable salt or solvate thereof.

In some embodiments, the MEK inhibitor is a compound of formula (I),

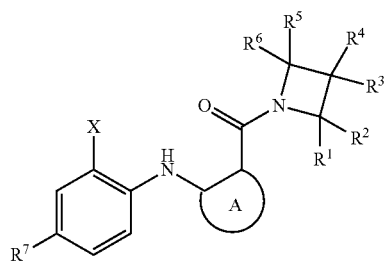

I or a pharmaceutically acceptable salt or solvate thereof, wherein A, X, $R^1$, $R^2$, $R^3$, $R^4$, $R^5$, $R^6$, and $R^7$ are as defined in Group A, Group B, Group C, or Group D:

Group A:

A is arylene optionally substituted with one, two, three or four groups selected from $R^{10}$, $R^{12}$, $R^{14}$, $R^{16}$, and $R^{19}$ where $R^{10}$, $R^{12}$, $R^{14}$ and $R^{16}$ are independently hydrogen, alkyl, alkenyl, alkynyl, halo, haloalkoxy, hydroxy, alkoxy, amino, alkylamino, dialkylamino, haloalkyl, —NHS(O)$_2R^8$, —CN, —C(O)$R^8$, —C(O)O$R^8$, —C(O)N$R^8R^{8'}$ and —N$R^8$C(O)$R^{8'}$ and where $R^{19}$ is hydrogen, alkyl, or alkenyl;

X is alkyl, halo, haloalkyl, or haloalkoxy;

$R^1$, $R^2$, $R^3$, $R^4$, $R^5$ and $R^6$ are independently hydrogen, halo, nitro, —N$R^8R^{8'}$, —O$R^8$, —NHS(O)$_2R^8$, —CN, —S(O)$_m R^8$, —S(O)$_2$N$R^8R^{8'}$, —C(O)$R^8$, —C(O)O$R^8$, —C(O)N$R^8R^{8'}$, —N$R^8$C(O)O$R^{8'}$, —N$R^8$C(O)$R^{8'}$, —N$R^8$C(O)N$R^8R^{8''}$, —N$R^8$C(O)O$R^{8'}$, —N$R^8$C(O)$R^{8'}$, —CH$_2$N($R^{25}$)(N$R^{25a}R^{25b}$), —CH$_2$N$R^{25}$C(=NH)(N$^{25a}R^{25b}$), —CH$_2$N$R^{25}$C(=NH)(N($R^{25a}$)(NO$_2$)), —CH$_2$N$R^{25}$C(=NH)(N($R^{25a}$)(CN)), —CH$_2$N$R^{25}$C(=NH)($R^{25}$), —CH$_2$N$R^{25}$C(N$R^{25a}R^{25b}$)=CH(NO$_2$), alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —O$R^8$, —N$R^8R^{8'}$, —N$R^8$S(O)$_2R^9$, —CN, —S(O)$_m R^9$, —C(O)$R^8$, —C(O)O$R^8$, —C(O)N$R^8R^{8'}$, N$R^8$C(O)N$R^8R^{8''}$, —N$R^8$C(O)O$R^{8'}$ and —N$R^8$C(O)$R^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(=NOH);

m is 0, 1, or 2;

$R^7$ is hydrogen, halo or alkyl;

each $R^8$, $R^{8'}$ and $R^{8''}$ is independently selected from hydrogen, hydroxy, optionally substituted alkoxy, alkyl, alkenyl, alkynyl, aryl, cycloalkyl, heteroaryl, and heterocycloalkyl; where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, alkoxycarbonyl, alkenyloxycarbonyl, optionally substituted cycloalkyl, optionally substituted cycloalkyloxycarbonyl, optionally substituted aryl, optionally substituted aryloxy, optionally substituted aryloxycarbonyl, optionally substituted arylalkyl, optionally substituted arylalkyloxy, optionally substituted arylalkyloxycarbonyl, nitro, cyano, optionally substituted heterocycloalkyl, optionally substituted heteroaryl, —S(O)$R^{31}$ (where n is 0, 1, or 2 and $R^{31}$ is optionally substituted alkyl, optionally substituted aryl, optionally substituted heterocycloalkyl, or optionally substituted heteroaryl), —N$R^{34}$SO$_2R^{34a}$ (where $R^{34}$ is hydrogen or alkyl and $R^{34a}$ is alkyl, alkenyl, cycloalkyl, aryl, heteroaryl, or heterocycloalkyl), —SO$_2$N$R^{35}R^{35a}$ (where $R^{35}$ is hydrogen or alkyl and $R^{35a}$ is alkyl, alkenyl, cycloalkyl, aryl, heteroaryl, or heterocycloalkyl), —N$R^{32}$C(O)$R^{32a}$ (where $R^{32}$ is hydrogen or alkyl and $R^{32a}$ is alkyl, alkenyl, alkoxy, or cycloalkyl), —N$R^{30}R^{30'}$ (where $R^{30}$ and $R^{30'}$ are independently hydrogen, alkyl, or hydroxyalkyl), and —C(O)N$R^{33}R^{33a}$ (where $R^{33}$ is hydrogen or alkyl and $R^{33a}$ is alkyl, alkenyl, alkynyl, or cycloalkyl); and each $R^9$ is independently selected from alkyl, alkenyl, alkynyl, aryl, cycloalkyl, heteroaryl, and heterocycloalkyl; where the alkyl, alkenyl, alkynyl, aryl, cycloalkyl, heteroaryl, and heterocycloalkyl are independently optionally susbstituted with one, two, three, four, or five groups selected from halo, hydroxy, alkyl, haloalkyl, haloalkoxy, amino, alkylamino, and dialkylamino;

Group B:

A is heteroarylene optionally substituted with one, two, three, or four groups selected from $R^{10}$, $R^{12}$, $R^{14}$, $R^{16}$ and $R^{19}$ where $R^{10}$, $R^{12}$, $R^{14}$ and $R^{16}$ are independently hydrogen, alkyl, alkenyl, alkynyl, halo, haloalkoxy, hydroxy, alkoxy, cyano, amino, alkylamino, dialkylamino, haloalkyl, alkylsulfonylamino, alkylcarbonyl, alkenylcarbonyl, alkoxycarbonyl, alkenyloxycarbonyl, aminocarbonyl, alkylaminocarbonyl, dialkylaminocarbonyl, or alkylcarbonylamino; where $R^{19}$ is hydrogen, alkyl, or alkenyl; and where each alkyl and alkenyl, either alone or as part of another group within $R^{10}$, $R^{12}$, $R^{14}$, $R^{16}$, and $R^{19}$, is independently optionally substituted with halo, hydroxy, or alkoxy;

X is alkyl, halo, haloalkyl, or haloalkoxy;

$R^1$, $R^2$, $R^3$, $R^4$, $R^5$ and $R^6$ are independently hydrogen, halo, nitro, $-NR^8R^{8'}$, $-OR^8$, $-NHS(O)_2R^8$, $-CN$, $-S(O)_mR^8$, $-S(O)_2NR^8R^{8'}$, $-C(O)R^8$, $-C(O)OR^8$, $-C(O)NR^8R^{8'}$, $-NR^8C(O)OR^{8'}$, $-NR^8C(O)NR^8R^{8''}$, $-NR^8C(O)OR^{8'}$, $-NR^8C(O)R^{8'}$, $-CH_2N(R^{25})(NR^{25a}R^{25b})$, $-CH_2NR^{25}C(=NH)(NR^{25a}R^{25b})$, $-CH_2NR^{25}C(=NH)N(R^{25a})(NO_2))$, $-CH_2NR^{25}C(NH)(NR^{25a})(CN))$, $-CH_2NR^{25}C(=NH)(R^{25})$, $-CH_2NR^{25}C(NR^{25a}N^{25b})=CH(NO_2)$, alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, $-OR^8$, $-NR^8R^{8'}$, $-NR^8S(O)_2R^9$, $-CN$, $-S(O)_mR^9$, $-C(O)R^8$, $-C(O)OR^8$, $-C(O)NR^8R^{8'}$, $-NR^8C(O)NR^8R^{8''}$, $-NR^8C(O)OR^{8'}$ and $-NR^8C(O)R^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(=NOH);

m is 1 or 2;

$R^7$ is hydrogen, halo or alkyl; and each $R^8$, $R^{8'}$ and $R^{8''}$ is independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, $-S(O)_nR^{31}$ (where n is 0, 1, or 2 and $R^{31}$ is optionally substituted alkyl, optionally substituted aryl, optionally substituted cycloalkyl, optionally substituted heterocycloalkyl, or optionally substituted heteroaryl), $-NR^{36}S(O)_2R^{36a}$ (where $R^{36}$ is hydrogen, alkyl, or alkenyl and $R^{36a}$ is alkyl, alkenyl, optionally substituted aryl, optionally substituted cycloalkyl, optionally substituted heterocycloalkyl, or optionally substituted heteroaryl), $-S(O)_2NR^{37}R^{37a}$ (where $R^{37}$ is hydrogen, alkyl, or alkenyl and $R^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl; optionally substituted arylalkyl, optionally substituted aryloxy, optionally substituted arylalkyloxy, optionally substituted heteroaryl, $-NHC(O)R^{32}$ (where $R^{32}$ is alkyl, alkenyl, alkoxy, or cycloalkyl) and $-NR^{30}R^{30'}$ (where $R^{30}$ and $R^{30'}$ are independently hydrogen, alkyl, or hydroxyalkyl), and $-C(O)NHR^{33}$ (where $R^{33}$ is alkyl, alkenyl, alkynyl, or cycloalkyl);

Group C:

A is

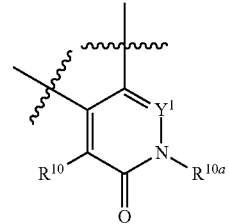

(a)

where $R^{10}$ is hydrogen, alkyl, alkenyl, alkynyl, halo, haloalkoxy, hydroxy, alkoxy, amino, alkylamino, dialkylamino, haloalkyl, $-NHS(O)_2R^8$, $-CN$, $-C(O)R^8$, $-C(O)OR^8$, $-C(O)NR^8R^{8'}$ and $-NR^8C(O)R^{8'}$;

$R^{10a}$ is hydrogen, alkyl, or alkenyl;

$Y^1$ is $=CH-$ or $=N-$;

X is alkyl, halo, haloalkyl, or haloalkoxy;

$R^1$, $R^2$, $R^3$, $R^4$, $R^5$ and $R^6$ are independently hydrogen, halo, nitro, $-NR^8R^{8'}$, $-OR^8$, $-NHS(O)_2R^8$, $-CN$, $-S(O)_mR^8$, $-S(O)_2NR^8R^{8'}$, $-C(O)R^8$, $-C(O)OR^8$, $-C(O)NR^8R^{8'}$, $-NR^8C(O)OR^{8'}$, $-NR^8C(O)NR^8R^{8''}$, $-NR^8C(O)OR^{8'}$, $-NR^8C(O)R^{8'}$, $-CH_2N(R^{25})NR^{25a}R^{25b})$, $-CH_2NR^{25}C(=NH)(NR^{25a}R^{25b})$, $-CH_2NR^{25}C(=NH)(N(R^{25a})(NO_2))$, $-CH_2NR^{25}C(=NH)(N(R^{25a})(CN))$, $-CH_2NR^{25}C(=NH)(R^{25})$, $-CH_2NR^{25}C(NR^{25a}R^{25b})=CH(NO_2)$, alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, $-OR^8$, $-NR^8R^{8'}$, $-NR^8S(O)_2R^9$, $-CN$, $-S(O)_mR^9$, $-C(O)R^8$, $-C(O)OR^8$, $-C(O)NR^8R^{8'}$, $-NR^8C(O)NR^8R^{8''}$, $-NR^8C(O)OR^{8'}$ and $-NR^8C(O)R^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(NOH);

m is 1 or 2;

$R^7$ is hydrogen, halo or alkyl; and each $R^8$, $R^{8'}$ and $R^{8''}$ is independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, $-S(O)_nR^{31}$ (where n is 0, 1, or 2 and $R^{31}$ is optionally substituted alkyl, optionally substituted aryl, optionally substituted cycloalkyl, optionally substituted heterocycloalkyl, or optionally substituted heteroaryl), $-NR^{36}S(O)_2R^{36a}$ (where $R^{36}$ is hydrogen, alkyl, or alkenyl and $R^{36a}$ is alkyl, alkenyl, optionally substituted aryl, optionally substituted cycloalkyl, optionally substituted heterocycloalkyl, or optionally substituted heteroaryl), $-S(O)_2NR^{37}R^{37a}$ (where $R^{37}$ is hydrogen, alkyl, or alkenyl and $R^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and —NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl); or Group D:

A is

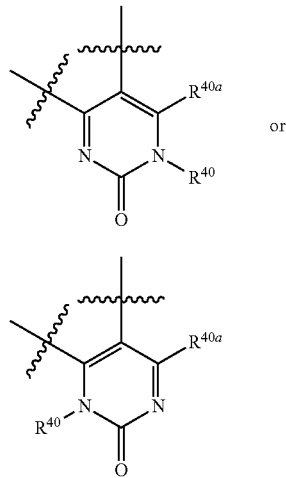

R$^{40}$ and R$^{40a}$ are independently hydrogen or alkyl;

X is alkyl, halo, haloalkyl, or haloalkoxy;

R$^1$, R$^2$, R$^3$, R$^4$, R$^5$ and R$^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^{8'}$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$) (NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$) =CH(NO$_2$), alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^{8'}$R$^{8''}$, —NR$^8$C(O)OR$^{8'}$ and —NR$^8$C(O)R$^{8'}$; or one of R$^1$ and R$^2$ together with the carbon to which they are attached, R$^3$ and R$^4$ together with the carbon to which they are attached, and R$^5$ and R$^6$ together with the carbon to which they are attached form C(O) or C(NOH);

m is 1 or 2;

R$^7$ is hydrogen, halo or alkyl; and

R$^8$, R$^{8'}$ and R$^{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —S(O)$_n$R$^{31}$ (where n is 0, 1, or 2 and R$^{31}$ is optionally substituted alkyl, optionally substituted aryl, optionally substituted cycloalkyl, optionally substituted heterocycloalkyl, or optionally substituted heteroaryl), —NR$^{36}$S(O)$_2$R$^{36a}$ (where R$^{36}$ is hydrogen, alkyl, or alkenyl and R$^{36a}$ is alkyl, alkenyl, optionally substituted aryl, optionally substituted cycloalkyl, optionally substituted heterocycloalkyl, or optionally substituted heteroaryl), —S(O)$_2$NR$^{37}$R$^{37a}$ (where R$^{37}$ is hydrogen, alkyl, or alkenyl and R$^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and —NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl).

In some variations, the MEK inhibitor compound of the formula (I) is a compound of the Group A, having the formula I(a) or I(b):

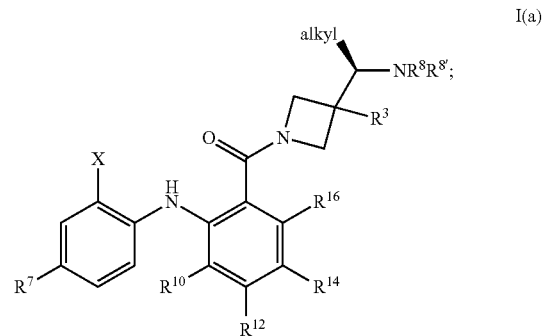

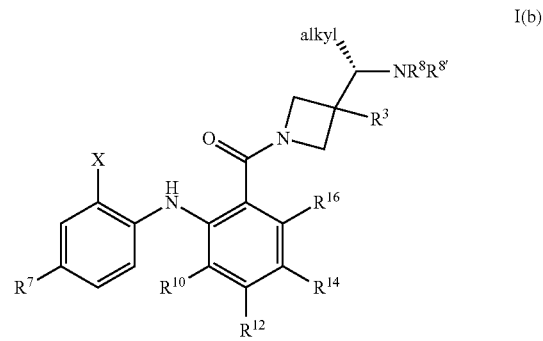

or a pharmaceutically acceptable salt or solvate thereof, wherein the variables are as defined for the formula (I), Group A, or as defined in WO 2007/044515 A1, incorporated herein by reference.

In some variations, the MEK inhibitor compound of the formula (I) is a compound of the Group B, having the formula I(c), I(d), I(e), I(f), I(g), I(h), I(i), I(j), I(k), I(m), I(n), I(O), I(p), I(q), I(r), I(s), I(u), I(v), I(w), I(x), I(cc) or I(dd):

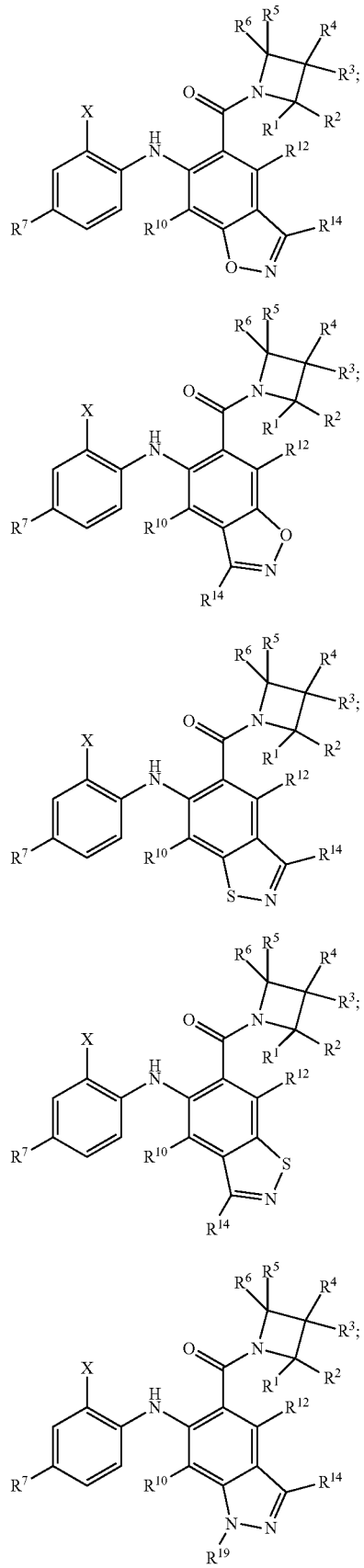
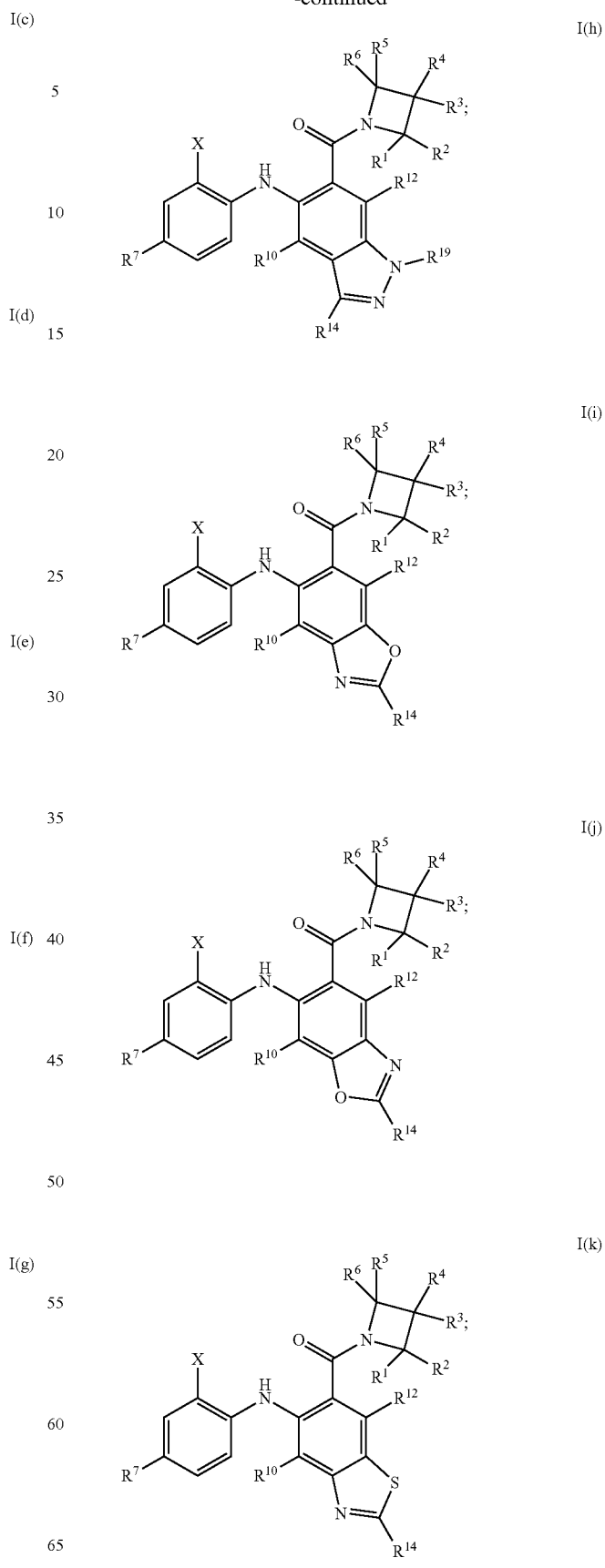

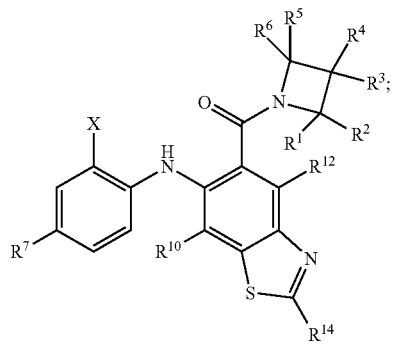
I(m)
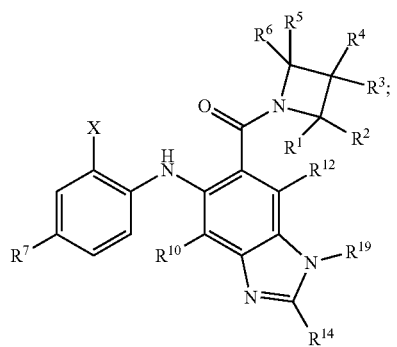
I(n)
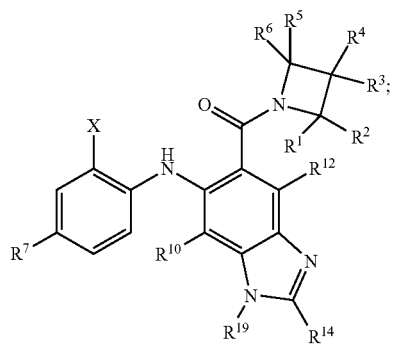
I(o)
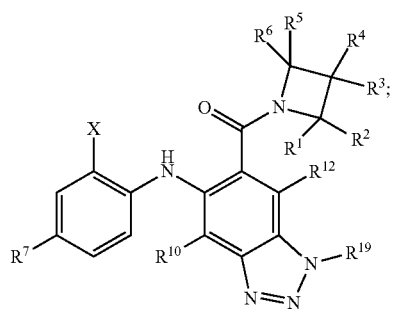
I(p)
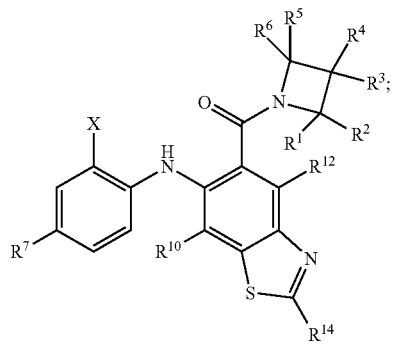
I(q)
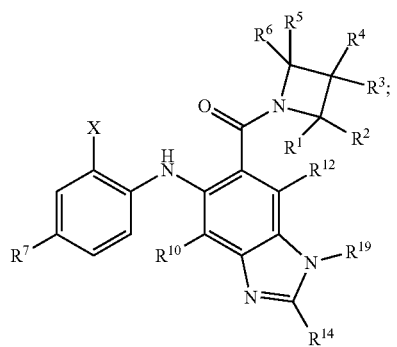
I(r)
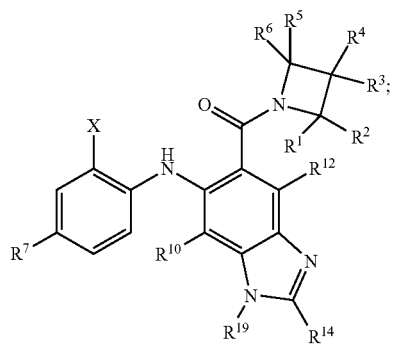
I(s)
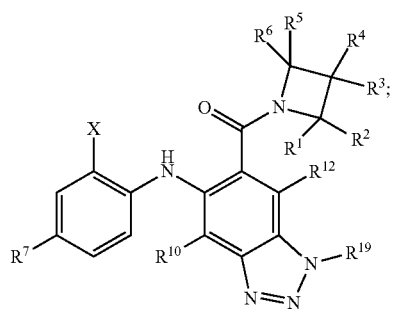
I(u)
I(v)

I(w)
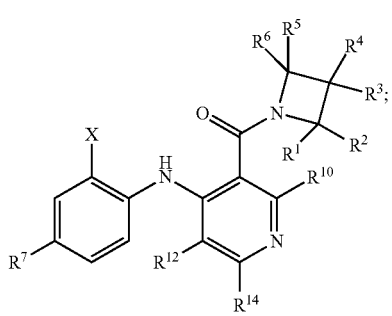

I(x)
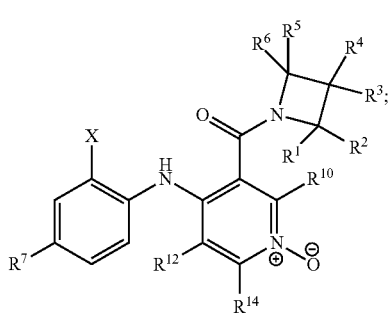

I(cc)
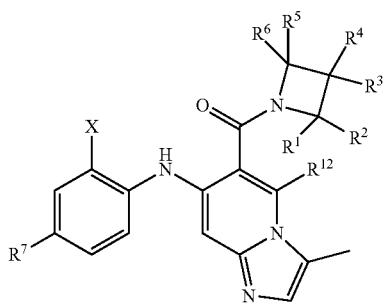

I(dd)
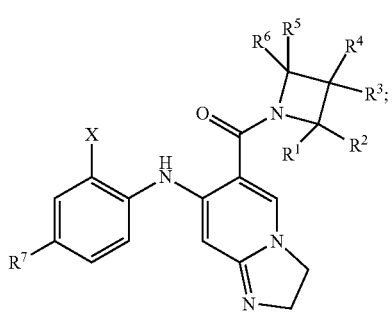

or a pharmaceutically acceptable salt or solvate thereof, wherein the variables are as defined for the formula (I), Group B, or as defined in WO 2007/044515 A1, incorporated herein by reference.

In some variations, the MEK inhibitor compound of the formula (I) is a compound of the Group C, having the formula I(y) or I(z):

I(y)
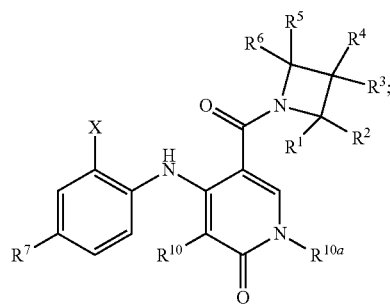

I(z)
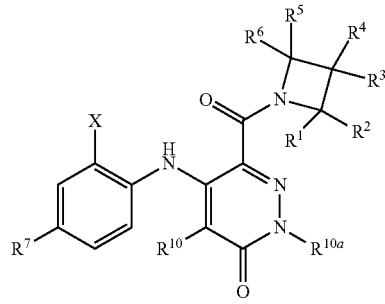

or a pharmaceutically acceptable salt or solvate thereof, wherein the variables are as defined for the formula (I), Group C, or as defined in WO 2007/044515 A1, incorporated herein by reference.

In some variations, the MEK inhibitor compound of the formula (I) is a compound of the Group D, having the formula I(aa) or I(bb):

I(aa)
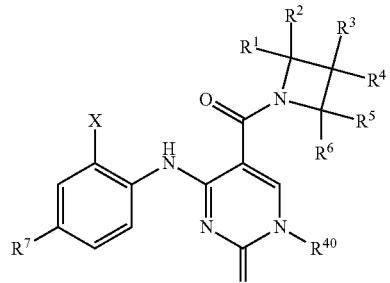

I(bb)
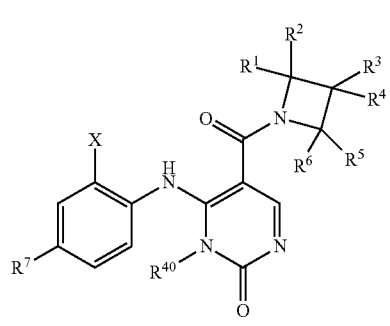

or a pharmaceutically acceptable salt or solvate thereof, wherein the variables are as defined for the formula (I), Group D, or as defined in WO 2007/044515 A1, incorporated herein by reference.

In some embodiments, the MEK inhibitor compound of the formula (I) is a compound selected from the compound Nos. 1-362 as listed in WO 2007/044515 A1, Table 1 on pages 71-144 (herein collectively referred to as the Formula I Species), or a pharmaceutically acceptable salt or solvate thereof.

Also embraced are any variations of formula (I) as described in WO 2007/044515 A1, which is incorporated herein by reference. Compounds of the formula (I) or any variations thereof can be synthesized using methods known in the art, for example, the synthetic methods described in WO 2007/044515 A1, incorporated herein by reference.

Unless defined otherwise herein, the terms used in describing compounds of the formula (I) should be understood to have the same meaning as defined in WO 2007/044515 A1.

In some embodiments, the MEK inhibitor is a compound of formula (II):

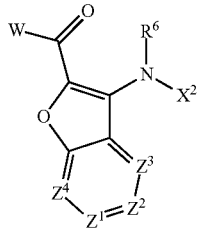

(II)

or a pharmaceutically acceptable salt or solvate thereof, wherein:

$Z^1$ is $CR^1$ or N;
$Z^2$ is $CR^2$ or N;
$Z^3$ is $CR^3$ or N;
$Z^4$ is $CR^4$ or N;
where one or two of $Z^1$, $Z^2$, $Z^3$, and $Z^4$ are N;

$R^1$, $R^2$, $R^3$ and $R^4$ are independently selected from H, halo, CN, $CF_3$, —$OCF_3$, —$NO_2$, —$(CR^{14}R^{15})_nC(=Y)R^{11}$, —$(CR^{14}R^{15})_nC(=Y)OR^{11}$, —$(CR^{14}R^{15})_nC(=Y)NR^{11}R^{12}$, —$(CR^{14}R^{15})_nNR^{11}R^{12}$, —$(CR^{14}R^{15})_nOR^{11}$, —$(CR^{14}R^{15})_nSR^{11}$, —$(CR^{14}R^{15})_nNR^{12}C(=Y)R^{11}$, —$(CR^{14}R^{15})_nNR^{12}C(=Y)OR^{11}$, —$(CR^{14}R^{15})_nNR^{13}C(=Y)NR^{11}R^{12}$, —$(CR^{14}R^{15})_nNR^{12}SO_2R^{11}$, —$(CR^{14}R^{15})_nOC(=Y)R^{11}$, —$(CR^{14}R^{15})_nOC(=Y)OR^{11}$, —$(CR^{14}R^{15})_nOC(=Y)NR^{11}R^{12}$, —$(CR^{14}R^{15})_nOS(O)_2(OR^{11})$, —$(CR^{14}R^{15})_nOP(=Y)(OR^{11})(OR^{12})$, —$(CR^{14}R^{15})_nOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, —$(CR^{14}R^{15})_nS(O)(OR^{11})$, —$(CR^{14}R^{15})_nS(O)_2(OR^{11})$, —$(CR^{14}R^{15})_nSC(=Y)R^{11}$, —$(CR^{14}R^{15})_nSC(=Y)OR^{11}$, —$(CR^{14}R^{15})_nSC(=Y)NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

W is

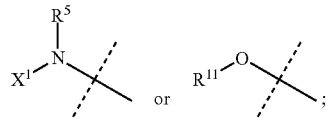

$R^5$ and $R^6$ are independently selected from H or $C_1$-$C_{12}$ alkyl;

$X^1$ is selected from $R^{11}$, —$OR^{11}$, —$NR^{11}R^{12}$, —$S(O)R^{11}$, and —$S(O)_2R^{11}$; when $X^1$ is $R^{11}$ or —$OR^{11}$, $R^{11}$ or —$OR^{11}$ of $X^1$ and —$R^5$ are optionally taken together with the nitrogen atom to which they are attached to form a 4-7 membered saturated or unsaturated ring having 0-2 additional heteroatoms selected from O, S and N, wherein said ring is optionally substituted with one or more groups selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^6$, —$(CR^{19}R^{20})_n$—$SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$;

$X^2$ is selected from carbocyclyl, heterocyclyl, aryl, and heteroaryl;

$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl, or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, —$OCF_3$, —$NO_2$, $C_1$-$C_6$ alkyl, —OH, —SH, —O($C_1$-$C_6$ alkyl), —S($C_1$-$C_6$ alkyl), —$NH_2$, —NH($C_1$-$C_6$ alkyl), —N($C_1$-$C_6$ alkyl)$_2$, —$SO_2$($C_1$-$C_6$ alkyl), —$CO_2H$, —$CO_2$($C_1$-$C_6$ alkyl), —C(O)$NH_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —$NHSO_2$($C_1$-$C_6$ alkyl), —N($C_1$-$C_6$ alkyl)$SO_2$($C_1$-$C_6$ alkyl), —$SO_2NH_2$, —$SO_2$NH($C_1$-$C_6$ alkyl), —$SO_2$N($C_1$-$C_6$ alkyl)$_2$, —OC(O)$NH_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

$R^{14}$ and $R^{15}$ are independently selected from H, $C_1$-$C_2$ alkyl, aryl, carbocyclyl, heterocyclyl, and heteroaryl;

m and n are independently selected from 0, 1, 2, 3, 4, 5, or 6;

Y is independently O, $NR^{11}$, or S;

wherein each said alkyl, alkenyl, alkynyl, carbocyclyl, heterocyclyl, aryl and heteroaryl of $R^1$, $R^2$, $R^3$, $R^4$, $R^5$, $R^6$, $X^1$, $X^2$, $R^{11}$, $R^{12}$, $R^{13}$, $R^{14}$, and $R^{15}$ is independently optionally substituted with one or more groups independently selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_n$—$SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$;

each $R^{16}$, $R^{17}$ and $R^{18}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, oxo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O ($C_1$-$C_6$ alkyl), —NHC(O)NH($C_1$-$C_6$ alkyl), —NHC(O)N ($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

or $R^{16}$ and $R^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

$R^{19}$ and $R^{20}$ are independently selected from H, $C_1$-$C_{12}$ alkyl, —(CH$_2$)$_n$-aryl, —(CH$_2$)$_n$-carbocyclyl, —(CH$_2$)$_n$-heterocyclyl, and —(CH$_2$)$_n$-heteroaryl;

$R^{21}$ is $C_1$-$C_{12}$ alkyl, $C_2$-$C_8$ alkenyl, $C_2$-$C_8$ alkynyl, carbocyclyl, heterocyclyl, aryl, or heteroaryl, wherein each member of $R^{21}$ is optionally substituted with one or more groups selected from halo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

each Y' is independently O, NR$^{22}$, or S; and
$R^{22}$ is H or $C_1$-$C_{12}$ alkyl.

In some variations, the MEK inhibitor compound of the formula (II) is a compound of the formula (II-1-a), (II-1-b), (II-1-c), (II-1-d), (II-1-e), (II-1-f), (II-1-g), (II-1-h), (II-1-i), (II-2-a), (II-2-b), (II-2-c), (II-2-d), (II-2-e), (II-2-f), (II-2-g), (II-2-h), (II-2-i), (II-3-a), (II-3-b), (II-3-c), (II-3-d), (II-3-e), (II-3-f), (II-3-g), (II-3-h), or (II-3-i):

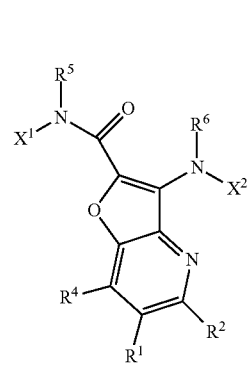

II-1-a

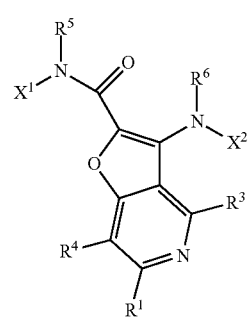

II-1-b

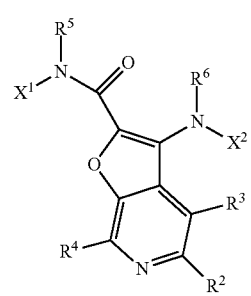

II-1-c

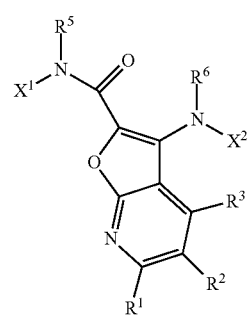

II-1-d

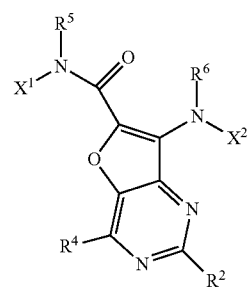

II-1-e

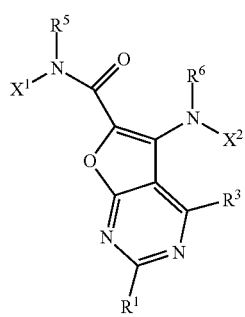 II-1-f
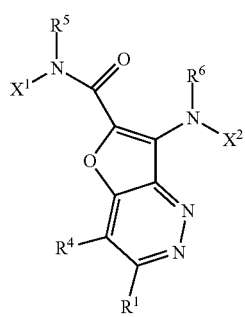 II-1-g
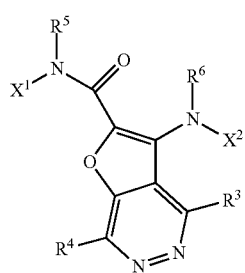 II-1-h
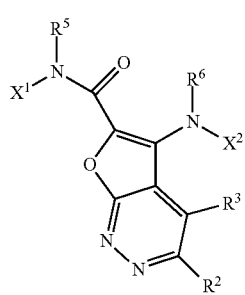 II-1-i
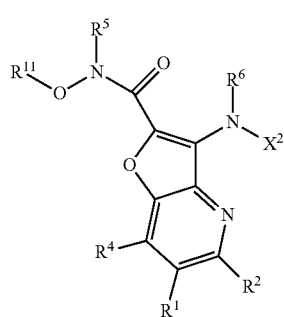 II-2-a
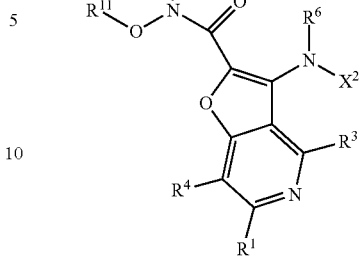 II-2-b
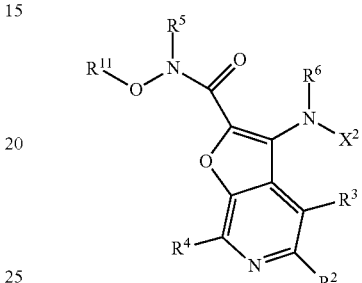 II-2-c
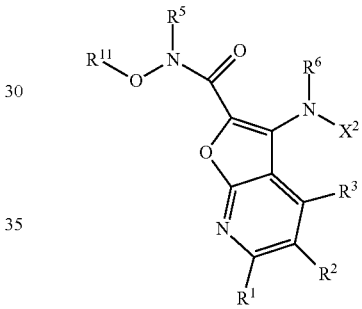 II-2-d
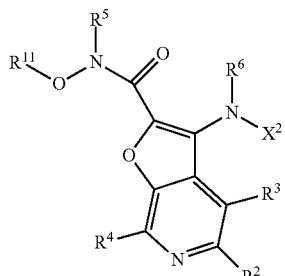 II-2-e
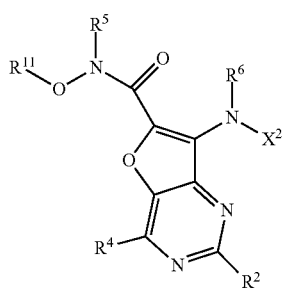 II-2-e
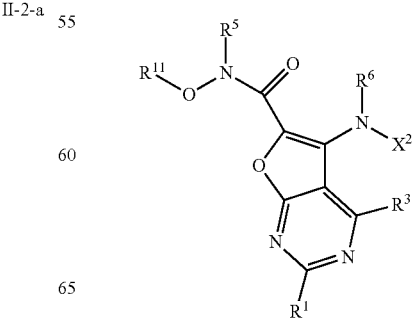 II-2-f

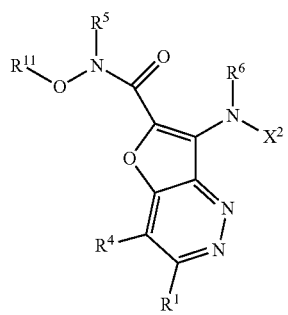
II-2-g
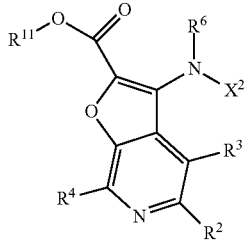
II-3-c
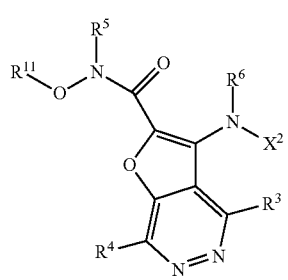
II-2-h
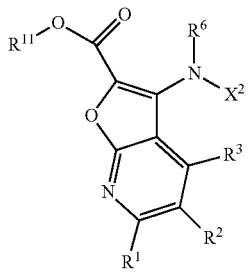
II-3-d
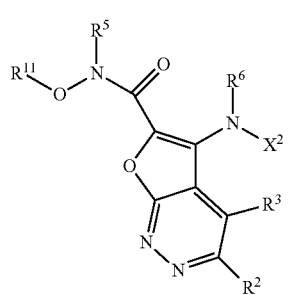
II-2-i
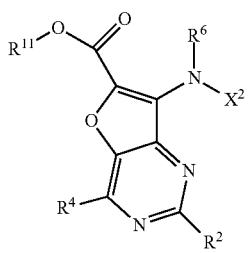
II-3-e
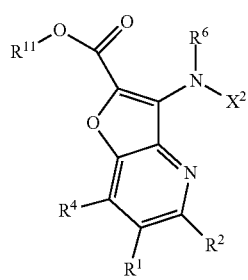
II-3-a
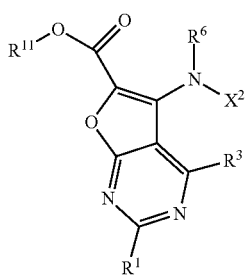
II-3-f
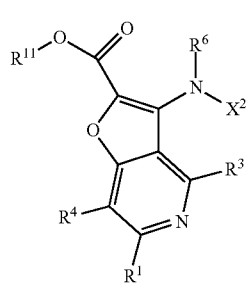
II-3-b
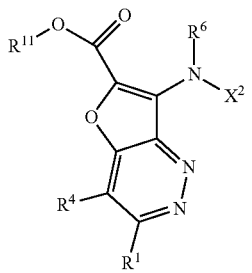
II-3-g
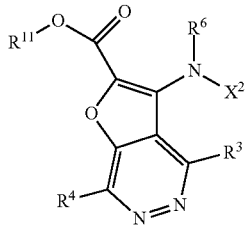
II-3-h -continued

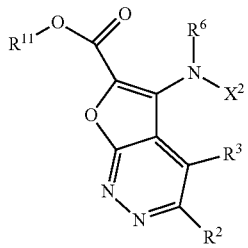

II-3-i or a pharmaceutically acceptable salt or solvate thereof, wherein the variables are as defined for the formula (II) or as defined in WO 2008/024725 A1, incorporated herein by reference.

In some embodiments, the MEK inhibitor compound of the formula (II) is a compound selected from the compounds of Examples 5-18, 20-102, 105-109, 111-118, 120-133, 136-149 and 151-160 in WO 2008/024725 A1 (herein collectively referred to as the Formula II Species), or a pharmaceutically acceptable salt or solvate thereof. These compounds exhibited an $IC_{50}$ of less than 10 μM in the assay described either in Example 8a or 8b (MEK activity assays). Most of these compounds exhibited an $IC_{50}$ of less than 5 μM. See page 62 in WO 2008/024725 A1.

Also embraced are MEK inhibitor compounds (and/or solvates and salts thereof) described in WO 2008/024725 A1, which is incorporated herein by reference, for example, aza-benzofuran compounds of the formula (II) (designated as formula I in WO 2008/024725 A1, e.g., on page 3) and variations thereof as described in WO 2008/024725 A1. Compounds of formula (II) can be synthesized using methods known in the art, for example, the synthetic methods described in WO 2008/024725 A1, incorporated herein by reference.

In some embodiments, the MEK inhibitor is a compound of formula (III):

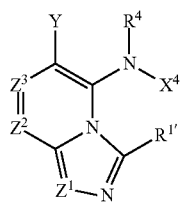

(III)

or a pharmaceutically acceptable salt or solvate thereof, wherein:

$Z^1$ is $CR^1$ or N;

$R^1$ is H, $C_1$-$C_3$ alkyl, halo, $CF_3$, $CHF_2$, CN, $OR^A$ or $NR^AR^A$;

$R^{1'}$ is H, $C_1$-$C_3$ alkyl, halo, $CF_3$, $CHF_2$, CN, $OR^A$, or $NR^AR^A$;

wherein each $R^A$ is independently H or $C_1$-$C_3$ alkyl;

$Z^2$ is $CR^2$ or N;

$Z^3$ is $CR^3$ or N; provided that only one of $Z^1$, $Z^2$ and $Z^3$ can be N at the same time;

$R^2$ and $R^3$ are independently selected from H, halo, CN, $CF_3$, —$OCF_3$, —$NO_2$, —$(CR^{14}R^{15})_nC(=Y')R^{11}$, —$(CR^{14}R^{15})_nC(=Y')OR^{11}$, —$(CR^{14}R^{15})_nC(=Y')NR^{11}R^{12}$, —$(CR^{14}R^{15})_nNR^{11}R^{12}$, —$(CR^{14}R^{15})_nOR^{11}$, —$(CR^{14}R^{15})_nSR^{11}$, —$(CR^{14}R^{15})_nNR^{12}C(=Y')R^{11}$, —$(CR^{14}R^{15})_nNR^{12}C(=Y')OR^{11}$, —$(CR^{14}R^{15})_nNR^{13}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')OR^{11}$, —$(CR^{14}R^{15})_nOC(=Y')NR^{11}R^{12}$, —$(CR^{14}R^{15})_nOS(O)_2(OR^{11})$, —$(CR^{14}R^{15})_nOP(=Y')(OR^{11})(OR^{12})$, —$(CR^{14}R^{15})_nOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, —$(CR^{14}R^{15})_nS(O)(OR^{11})$, —$(CR^{14}R^{15})_nS(O)_2(OR^{11})$, —$(CR^{14}R^{15})_nSC(=Y')R^{11}$, —$(CR^{14}R^{15})_nSC(=Y')OR^{11}$, —$(CR^{14}R^{15})_nSC(=Y')NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

$R^4$ is H, $C_1$-$C_6$ alkyl or $C_3$-$C_4$ carbocyclyl;

Y is W—C(O)— or W';

W is

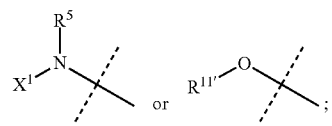

$R^5$ is H or $C_1$-$C_{12}$ alkyl;

$X^1$ is selected from $R^{11'}$ and —$OR^{11'}$; when $X^1$ is $R^{11'}$, $X^1$ is optionally taken together with $R^5$ and the nitrogen atom to which they are bound to form a 4-7 membered saturated or unsaturated ring having 0-2 additional heteroatoms selected from O, S and N, wherein said ring is optionally substituted with one or more groups selected from halo, CN, $CF_3$, —$OCF_3$, —$NO_2$, oxo, —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^6$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$;

each $R^{11'}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl;

$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl, or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, —$OCF_3$, —$NO_2$, $C_1$-$C_6$ alkyl, —OH, —SH, —$O(C_1$-$C_6$ alkyl), —$S(C_1$-$C_6$ alkyl), —$NH_2$, —$NH(C_1$-$C_6$ alkyl), —$N(C_1$-$C_6$ alkyl)$_2$, —$SO_2(C_1$-$C_6$ alkyl), —$CO_2H$, —$CO_2(C_1$-$C_6$ alkyl), —$C(O)NH_2$, —$C(O)NH(C_1$-$C_6$ alkyl), —$C(O)N(C_1$-$C_6$ alkyl)$_2$, —$N(C_1$-$C_6$ alkyl)$C(O)(C_1$-$C_6$ alkyl), —$NHC(O)(C_1$-$C_6$ alkyl), —$NHSO_2(C_1$-$C_6$ alkyl), —$N(C_1$-$C_6$ alkyl)$SO_2(C_1$-$C_6$ alkyl), —$SO_2NH_2$, —$SO_2NH(C_1$-$C_6$ alkyl), —$SO_2N(C_1$-$C_6$ alkyl)$_2$, —$OC(O)NH_2$, —$OC(O)NH(C_1$-$C_6$ alkyl), —$OC(O)N(C_1$-$C_6$ alkyl)$_2$, —$OC(O)O(C_1$-$C_6$ alkyl), —$NHC(O)NH(C_1$-$C_6$ alkyl), —$NHC(O)N(C_1$-$C_6$ alkyl)$_2$, —$N(C_1$-$C_6$ alkyl)$C(O)NH(C_1$-$C_6$ alkyl), —$N(C_1$-$C_6$ alkyl)$C(O)N(C_1$-$C_6$ alkyl)$_2$, —$NHC(O)NH(C_1$-$C_6$ alkyl), —$NHC(O)N(C_1$-$C_6$ alkyl)$_2$, —$NHC(O)O(C_1$-$C_6$ alkyl), and —$N(C_1$-$C_6$ alkyl)$C(O)O(C_1$-$C_6$ alkyl);

$R^{14}$ and $R^{15}$ are independently selected from H, $C_1$-$C_{12}$ alkyl, aryl, carbocyclyl, heterocyclyl, and heteroaryl;

W is

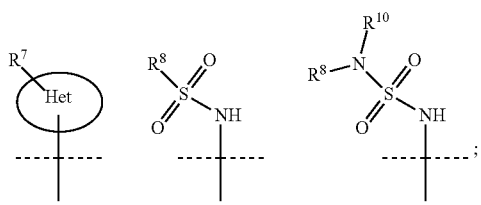

wherein

is

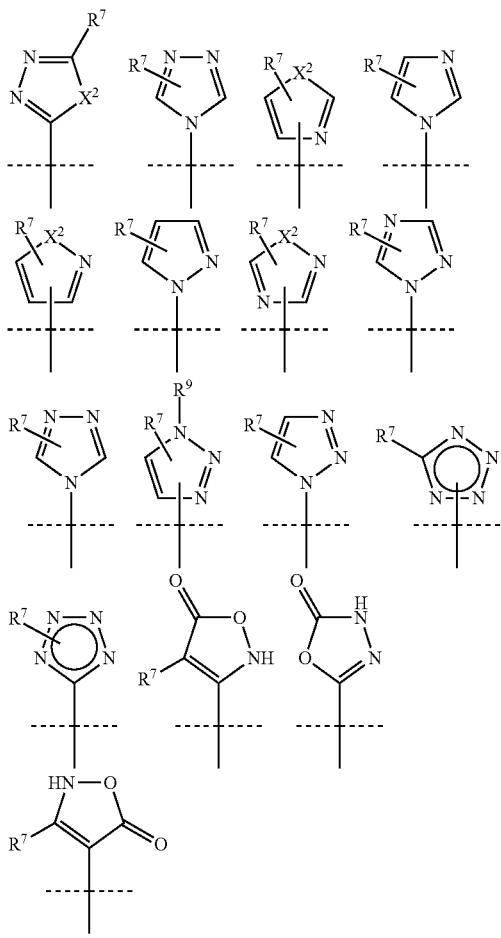

each $X^2$ is independently O, S, or $NR^9$;

each $R^7$ is independently selected from H, halo, CN, $CF_3$, —$OCF_3$, —$NO_2$, —$(CR^{14}R^{15})_nC(=Y')R^{11}$, —$(CR^{14}R^{15})_nC(=Y')OR^{11}$, —$(CR^{14}R^{15})_nC(=Y')NR^{11}R^{12}$, —$(CR^{14}R^{15})_nNR^{11}R^{12}$, —$(CR^{14}R^{15})_nOR^{11}$, —$(CR^{14}R^{15})_nSR^{11}$, —$(CR^{14}R^{15})_nNR^{12}C(=Y')R^{11}$, —$(CR^{14}R^{15})_nNR^{12}C(=Y')OR^{11}$, —$(CR^{14}R^{15})_nNR^{13}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')OR^{11}$, —$(CR^{14}R^{15})_nOC(=Y')NR^{11}R^{12}$, —$(CR^{14}R^{15})_nOS(O)_2(OR^{11})$, —$(CR^{14}R^{15})_nOP(=Y')(OR^{11})(OR^{12})$, —$(CR^{14}R^{15})_nOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, —$(CR^{14}R^{15})_nS(O)(OR^{11})$, —$(CR^{14}R^{15})_nS(O)_2(OR^{11})$, —$(CR^{14}R^{15})_nSC(=Y')R^{11}$, —$(CR^{14}R^{15})_nSC(=Y')OR^{11}$, —$(CR^{14}R^{15})_nSC(=Y')NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

each $R^8$ is independently selected from $C_1$-$C_{12}$ alkyl, aryl, carbocyclyl, heterocyclyl, and heteroaryl;

$R^9$ is selected from H, —$(CR^{14}R^{15})_nC(=Y')R^{11}$, —$(CR^{14}R^{15})_nC(=Y')OR^{11}$, —$(CR^{14}R^{15})_nC(=Y')NR^{11}R^{12}$, —$(CR^{14}R^{15})_qNR^{11}R^{12}$, —$(CR^{14}R^{15})_qOR^{11}$, —$(CR^{14}R^{15})_qSR^{11}$, —$(CR^{14}R^{15})_qNR^{12}C(=Y')R^{11}$, —$(CR^{14}R^{15})_qNR^{12}C(=Y')OR^{11}$, —$(CR^{14}R^{15})_qNR^{13}C(=Y')NR^{11}R^{12}$, —$(CR^{14}R^{15})_qNR^{12}SO_2R^{11}$, —$(CR^{14}R^{15})_qOC(=Y')R^{11}$, —$(CR^{14}R^{15})_qOC(=Y')OR^{11}$, —$(CR^{14}R^{15})_qOC(=Y')NR^{11}R^{12}$, —$(CR^{14}R^{15})_qOS(O)_2(OR^{11})$, —$(CR^{14}R^{15})_qOP(=Y')(OR^{11})(OR^{12})$, —$(CR^{14}R^{15})_qOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, $C_1$-$C_{12}$ alkyl, $C_1$-$C_8$ alkenyl, $C_2$-$C_8$ alkynyl, carbocyclyl, heterocyclyl, aryl, and heteroaryl;

$R^{10}$ is H, $C_1$-$C_6$ alkyl or $C_3$-$C_4$ carbocyclyl;

$X^4$ is

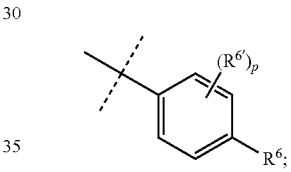

$R^6$ is H, halo, $C_1$-$C_6$ alkyl, $C_2$-$C_8$ alkenyl, $C_2$-$C_8$ alkynyl, carbocyclyl, heteroaryl, heterocyclyl, —$OCF_3$, —$NO_2$, —Si($C_1$-$C_6$ alkyl), —$(CR^{19}R^{20})_nNR^{16}R^{17}$, —$(CR^{19}R^{20})_nOR^{16}$, or —$(CR^{19}R^{20})_n$—$SR^{16}$;

$R^{6'}$ is H, halo, $C_1$-$C_6$ alkyl, carbocyclyl, $CF_3$, —$OCF_3$, —$NO_2$, —Si($C_1$-$C_6$ alkyl), —$(CR^{19}R^{20})_nNR^{16}R^{17}$, —$(CR^{19}R^{20})_nOR^{16}$, —$(CR^{19}R^{20})_n$—$SR^{16}$, $C_2$-$C_8$ alkenyl, $C_2$-$C_8$ alkynyl, heterocyclyl, aryl, or heteroaryl;

p is 0, 1, 2 or 3;

n is 0, 1, 2 or 3;

q is 2 or 3 wherein each said alkyl, alkenyl, alkynyl, carbocyclyl, heterocyclyl, aryl and heteroaryl of $R^1$, $R^2$, $R^3$, $R^4$, $R^5$, $R^6$, $R^{6'}$, $R^7$, $R^8$, $R^9$, $R^{10}$, $R^{11}$, $R^{11'}$, $R^{12}$, $R^{13}$, $R^{14}$, $R^{15}$ and $R^A$ is independently optionally substituted with one or more groups independently selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$;

each $R^{16}$, $R^{17}$ and $R^{18}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

or $R^{16}$ and $R^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

$R^{19}$ and $R^{20}$ are independently selected from H, $C_1$-$C_{12}$ alkyl, —(CH$_2$)$_n$-aryl, —(CH$_2$)$_n$-carbocyclyl, —(CH$_2$)$_n$-heterocyclyl, and —(CH$_2$)$_n$-heteroaryl;

$R^{21}$ is $C_1$-$C_{12}$ alkyl, $C_2$-$C_8$ alkenyl, $C_2$-$C_8$ alkynyl, carbocyclyl, heterocyclyl, aryl, or heteroaryl, wherein each member of $R^{21}$ is optionally substituted with one or more groups selected from halo, oxo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

each $Y'$ is independently O, NR$^{22}$, or S; and
$R^{22}$ is H or $C_1$-$C_{12}$ alkyl.

In some variations, the MEK inhibitor compound of the formula (III) has the formula (III-a) or (II-b):

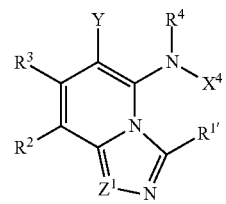

III-a

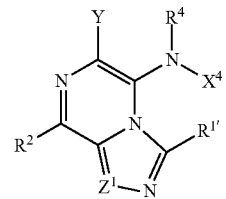

III-b or a pharmaceutically acceptable salt or solvate thereof, wherein the variables are as defined for the formula (III) or as defined in WO 2009/085983 A1, incorporated herein by reference.

In some embodiments, the MEK inhibitor compound of the formula (III) is a compound selected from the compounds listed in Table 1, or a pharmaceutically acceptable salt or solvate thereof.

TABLE 1

| Compound No. | Chemical Name | Structure |
| --- | --- | --- |
| (III)-5 | 5-(2-Fluoro-4-iodophenylamino)-imidazo[1,5-a]pyridine-6-carboxylic acid (2-hydroxyethoxy)-amide | 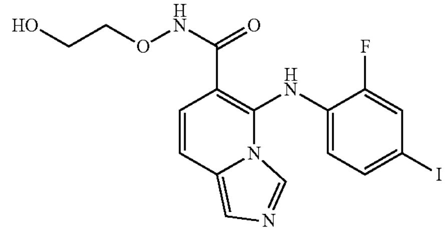 [SMILES: O=C(NOCCO)c1ccc2cncn2c1Nc1ccc(I)cc1F] |

TABLE 1-continued

| Compound No. | Chemical Name | Structure |
|---|---|---|
| (III)-6 | 5-(2-Fluoro-4-iodo-phenylamino)-imidazo[1,5-a]pyridine-6-carboxylic acid ((R)-2,3-dihydroxy-propoxy)-amide | 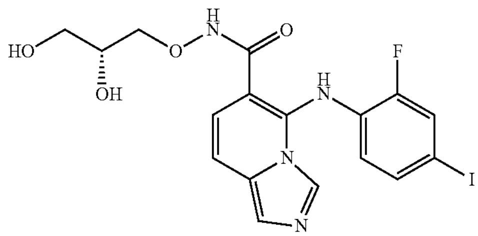 [SMILES: O=C(NOC[C@H](O)CO)c1ccc2cncn2c1Nc1ccc(I)cc1F] |
| (III)-7 | 5-(2-Fluoro-4-iodo-phenylamino)-imidazo[1,5-a]pyridine-6-carboxylic acid ((S)-2-hydroxy-propoxy)-amide | 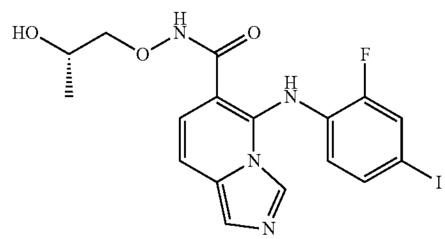 [SMILES: C[C@H](O)CONC(=O)c1ccc2cncn2c1Nc1ccc(I)cc1F] |
| (III)-8 | 5-(4-Bromo-2-fluorophenylamino)-imidazo[1,5-a]pyridine-6-carboxylic acid (2-hydroxyethoxy)-amide | 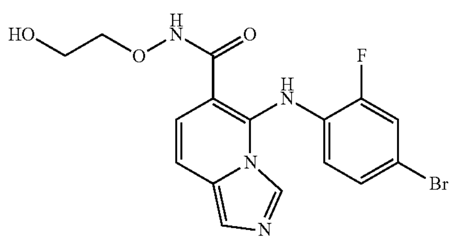 [SMILES: O=C(NOCCO)c1ccc2cncn2c1Nc1ccc(Br)cc1F] |
| (III)-9 | 5-(4-Bromo-2-fluoro-phenylamino)-imidazo[1,5-a]pyridine-6-carboxylic acid ((S)-2-hydroxy-propoxy)-amide | 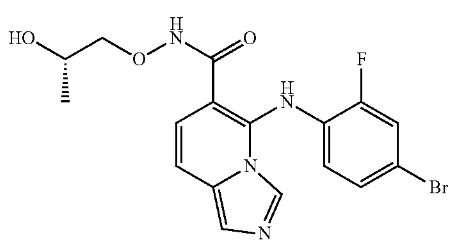 [SMILES: C[C@H](O)CONC(=O)c1ccc2cncn2c1Nc1ccc(Br)cc1F] |
| (III)-10 | 5-(4-Bromo-2-fluoro-phenylamino)-8-fluoro-imidazo[1,5-a]pyridine-6-carboxylic acid ((S)-2-hydroxy-propoxy)-amide | 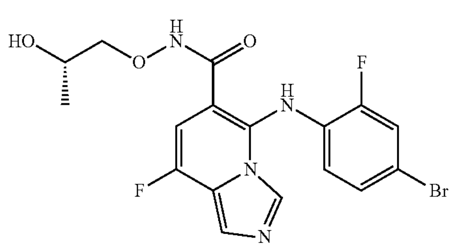 [SMILES: C[C@H](O)CONC(=O)c1cc(F)c2cncn2c1Nc1ccc(Br)cc1F] |
| (III)-11 | 8-Fluoro-5-(2-fluoro-4-iodo-phenylamino)-imidazo[1,5-a]pyridine-6-carboxylic acid (2-hydroxy-ethoxy)-amide | 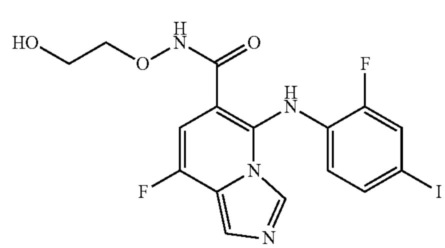 [SMILES: O=C(NOCCO)c1cc(F)c2cncn2c1Nc1ccc(I)cc1F] |

TABLE 1-continued

| Compound No. | Chemical Name | Structure |
| --- | --- | --- |
| (III)-12 | 8-Fluoro-5-(2-fluoro-4-iodo-phenylamino)-imidazo[1,5-a]pyridine-6-carboxylic acid ((R)-2,3-dihydroxy-propoxy)-amide | 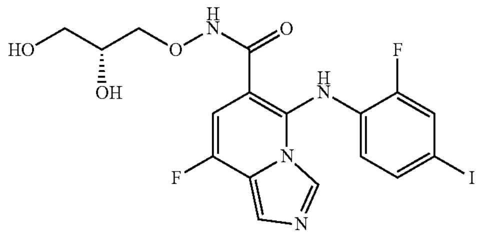 [SMILES: O=C(NOC[C@H](O)CO)c1cc(F)c2cncn2c1Nc1ccc(I)cc1F] |
| (III)-13 | 8-Fluoro-5-(2-fluoro-4-iodo-phenylamino)-imidazo[1,5-a]pyridine-6-carboxylic acid ((S)-2-hydroxy-propoxy)-amide | 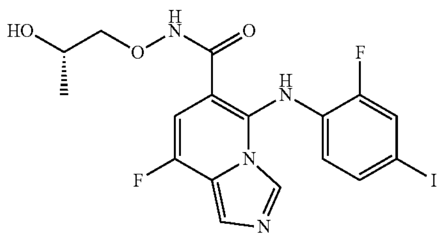 [SMILES: C[C@H](O)CONC(=O)c1cc(F)c2cncn2c1Nc1ccc(I)cc1F] |
| (III)-14 | 5-(2-Fluoro-methanesulfanyl-phenylamino)-imidazo[1,5-a]pyridine-6-carboxylic acid (2-hydroxy-ethoxy)-amide | 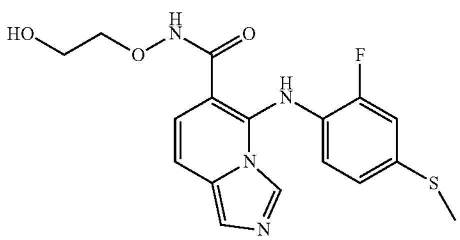 [SMILES: CSc1ccc(Nc2c(C(=O)NOCCO)ccc3cncn23)c(F)c1] |
| (III)-15 | 5-(2-Fluoro-4-iodo-phenylamino)-imidazo[1,5-a]pyrazine-6-carboxylic acid (2-hydroxy-ethoxy)-amide | 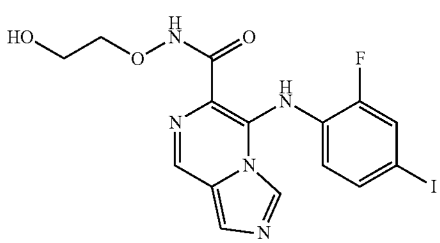 [SMILES: O=C(NOCCO)c1ncc2cncn2c1Nc1ccc(I)cc1F] |
| (III)-16 | 5-(2-Fluoro-4-iodo-phenylamino)-imidazo[1,5-a]pyrazine-6-carboxylic acid ((S)-2-hydroxy-propoxy)-amide | 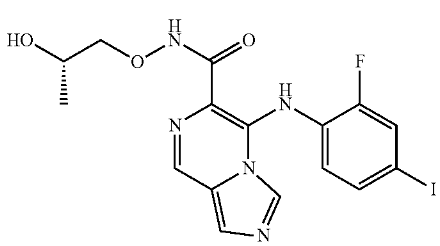 [SMILES: C[C@H](O)CONC(=O)c1ncc2cncn2c1Nc1ccc(I)cc1F] |
| (III)-17 | 5-(4-Cyclopropyl-2-fluoro-phenylamino)-imidazo[1,5-a]pyridine-6-carboxylic acid (2-hydroxy-ethoxy)-amide | 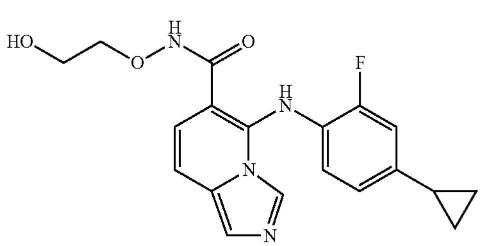 [SMILES: O=C(NOCCO)c1ccc2cncn2c1Nc1ccc(C2CC2)cc1F] |

TABLE 1-continued

| Compound No. | Chemical Name | Structure |
|---|---|---|
| (III)-18 | (R)-N-(2,3-Dihydroxypropoxy)-5-(2-fluoro-4-iodophenylamino)imidazo[1,5-a]pyrazine-6-carboxamide | 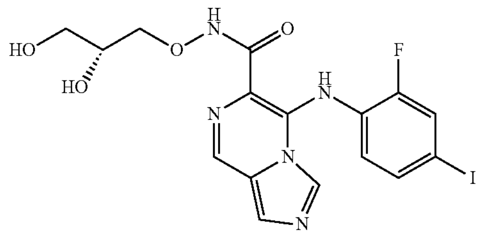 [SMILES: O=C(NOC[C@H](O)CO)c1ncc2cncn2c1Nc1ccc(I)cc1F] |
| (III)-19 | N-Ethoxy-5-(2-fluoro-4-iodophenylamino)imidazo[1,5-a]pyrazine-6-carboxamide | 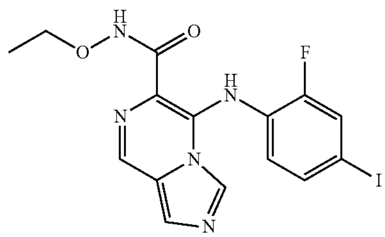 [SMILES: CCONC(=O)c1ncc2cncn2c1Nc1ccc(I)cc1F] |
| (III)-20 | N-(Cyclopropylmethoxy)-5-(2-fluoro-4-iodophenylamino)imidazo[1,5-a]pyrazine-6-carboxamide | 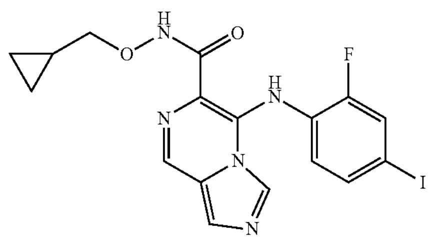 [SMILES: O=C(NOCC1CC1)c1ncc2cncn2c1Nc1ccc(I)cc1F] |
| (III)-21 | 5-(2-Fluoro-4-iodophenylamino)-N-methylimidazo[1,5-a]pyrazine-6-carboxamide | 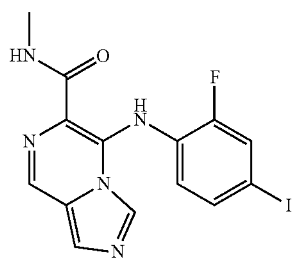 [SMILES: CNC(=O)c1ncc2cncn2c1Nc1ccc(I)cc1F] |
| (III)-22 | 5-(4-Bromo-2-fluorophenylamino)-N-(2-hydroxy-ethoxy)imidazo[1,5-a]pyrazine-6-carboxamide | 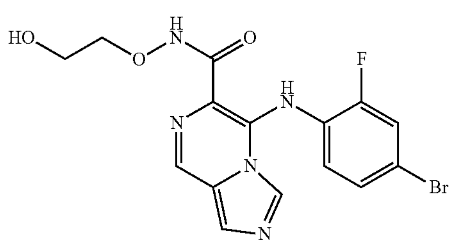 [SMILES: O=C(NOCCO)c1ncc2cncn2c1Nc1ccc(Br)cc1F] |
| (III)-23 | (S)-5-(4-Bromo-2-fluorophenylamino)-N-(2-hydroxy-propoxy)imidazo[1,5-a]pyrazine-6-carboxamide | 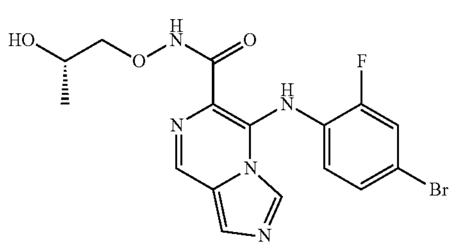 |

TABLE 1-continued

| Compound No. | Chemical Name | Structure |
|---|---|---|
| (III)-24 | (R)-5-(4-Bromo-2-fluorophenylamino)-N-(2,3-dihydroxy-propoxy)imidazo[1,5-a]pyrazine-6-carboxamide | 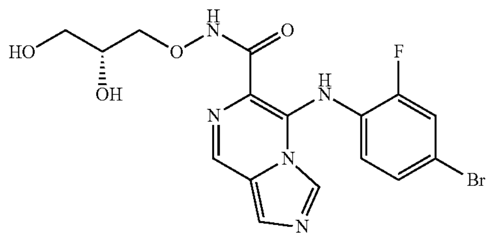 [SMILES: O=C(NOC[C@H](O)CO)c1ncc2cncn2c1Nc1ccc(Br)cc1F] |
| (III)-25 | 5-(4-Bromo-2-fluorophenylamino)-N-(cyclopropyl-methoxy)imidazo[1,5-a]pyrazine-6-carboxamide | 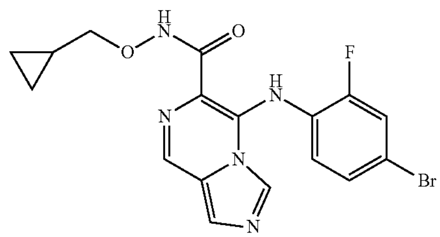 [SMILES: O=C(NOCC1CC1)c1ncc2cncn2c1Nc1ccc(Br)cc1F] |

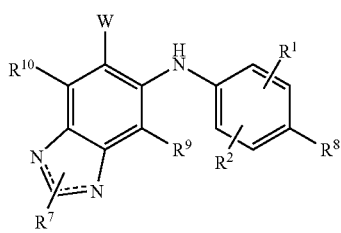

Compounds in Table 1 correspond to Examples 5-25 in WO 2009/085983 A1. Compounds (III)-5-(III)-20 and (III)-22-(III)-24 exhibited an $IC_{50}$ of less than 0.5 µM in the assay described in Example 8b (MEK activity assay). Some of these compounds exhibited an $IC_{50}$ of less than 0.1 µM. Compounds (III)-21 and (III)-25 exhibited an $IC_{30}$ of less than 10 µM. See page 49 in WO 2009/085983 A1.

Also embraced are MEK inhibitor compounds (and/or solvates and salts thereof) described in WO 2009/085983 A1, which is incorporated herein by reference, for example, imidazopyridine compounds of the formula (III) (designated as formula I in WO 2009/085983 A1, e.g., on page 3) and variations thereof as described in WO 2009/085983 A1. Compounds of formula (III) can be synthesized using methods known in the art, for example, the synthetic methods described in WO 2009/085983 A1, incorporated herein by reference.

In some embodiments, the MEK inhibitor is a compound of formula (IV),

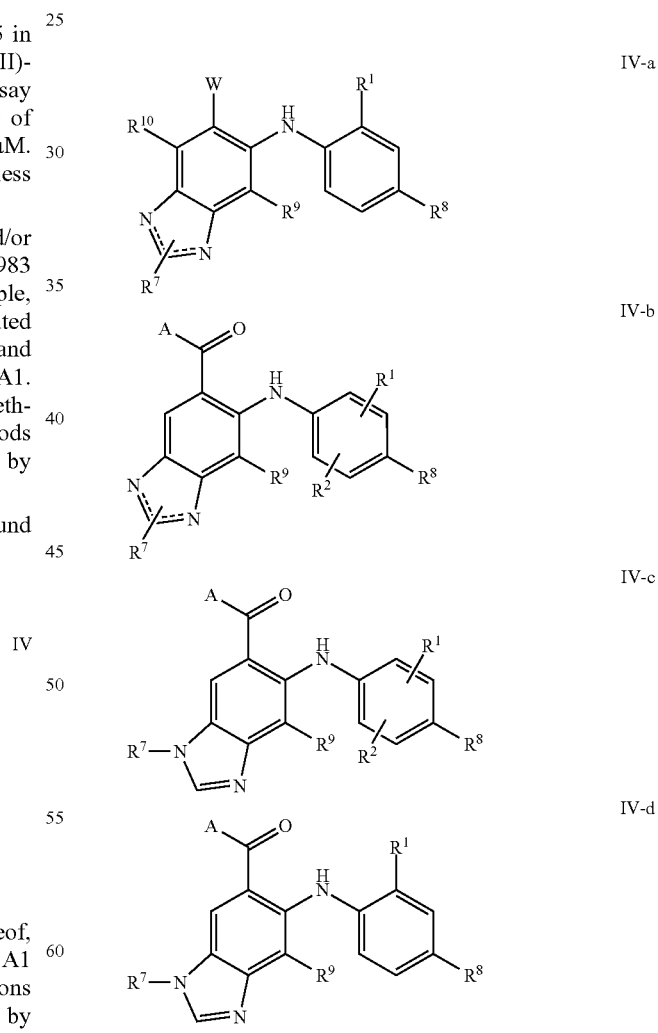

or a pharmaceutically acceptable salt or solvate thereof, wherein the variables are as defined in WO 03/077914 A1 for the formula I on pages 4-9 or any applicable variations described in WO 03/077914 A1, incorporated herein by reference.

In some variations, the MEK inhibitor compound of the formula (IV) is a compound of the formula (IV-a), (N-b), (N-c), or (IV-d):

or a pharmaceutically acceptable salt or solvate thereof, wherein the variables are as defined in WO 03/077914 A1 for the formulae II, III, IIIa and IIIb, respectively on pages 10-13 or any applicable variations described in WO 03/077914 A1, incorporated herein by reference.

In some embodiments, the MEK inhibitor compound of the formula (IV) is a compound selected from the group consisting of:
7-Fluoro-6-(4-bromo-2-methyl-phenylamino)-3H-benzoimidazole-5-carboxylic acid cyclopropylmethoxy-amide;
6-(4-Bromo-2-chloro-phenylamino)-7-fluoro-3H-benzoimidazole-5-carboxylic acid cyclopropylmethoxy-amide;
6-(4-Bromo-2-chloro-phenylamino)-7-fluoro-3-methyl-3H-benzoimidazole-5-carboxylic acid (2-hydroxy-ethoxy)-amide;
6-(4-Bromo-2-chloro-phenylamino)-7-fluoro-3-methyl-3H-benzoimidazole-5-carboxylic acid (2,3-dihydroxy-propoxy)-amide;
6-(4-Bromo-2-chloro-phenylamino)-7-fluoro-3-(tetrahydro-pyran-2-ylmethyl)-3H-benzoimidazole-5-carboxylic acid (2-hydroxy-ethoxy)-amide;
[6-(5-Amino-[1,3,4]oxadiazol-2-yl)-4-fluoro-H-benzoimidazol-5-yl]-(4-bromo-2-methyl-phenyl)-amine;
1-[6-(4-Bromo-2-chloro-phenylamino)-7-fluoro-3-methyl-3H-benzoimidazol-5-yl]-2-hydroxy-ethanone;
1-[6-(4-Bromo-2-chloro-phenylamino)-7-fluoro-3H-benzoimidazol-5-yl]-2-methoxy ethanone;
6-(4-Bromo-2-chloro-phenylamino)-7-fluoro-3-methyl-3H-benzoimidazole-5-carboxylic acid (2-hydroxy-1,1-dimethyl-ethoxy)-amide;
6-(4-Bromo-2-chloro-phenylamino)-7-fluoro-3-(tetrahydro-furan-2-ylmethyl)-3H-benzoimidazole-5-carboxylic acid (2-hydroxy-ethoxy)-amide;
6-(4-Bromo-2-chloro-phenylamino)-7-fluoro-3H-benzoimidazole-5-carboxylic acid (2-hydroxy-ethoxy)-amide;
6-(-Bromo-2-fluoro-phenylamino)-7-fluoro-3-methyl-3H-benzoimidazole-5-carboxylic acid (2-hydroxy-ethoxy)-amide; and
6-(2,4-Dichloro-phenylamino)-7-fluoro-3-methyl-3H-benzoimidazole-5-carboxylic acid (2-hydroxy-ethoxy)-amide;
or a pharmaceutically acceptable salt or solvate thereof.

Also embraced are any variations of formula (IV) as described in WO 03/077914 A1, which is incorporated herein by reference. Compounds of the formula (IV) or any variations thereof can be synthesized using methods known in the art, for example, the synthetic methods described in WO 03/077914 A1, incorporated herein by reference.

In some embodiments, the MEK inhibitor is a compound of formula (V),

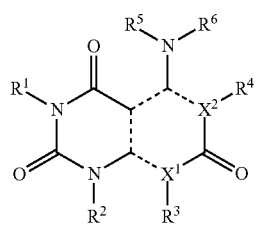

or a pharmaceutically acceptable salt or solvate thereof, wherein the variables are as defined in WO 2005/121142 A1 for the formula [1] on pages 6-10 or any applicable variations described in WO 2005/121142 A1, incorporated herein by reference.

Also embraced are any variations of formula (V) as described in WO 2005/121142 A1, such as the individual MEK inhibitor compounds described in WO 2005/121142 A1, e.g., Examples 1-1 to 1-343 in Table 1, Examples 2-1 and 2-2 in Table 2, Examples 3-1 to 3-9 in Table 3, Examples 4-1 to 4-148 in Table 4. Compounds of the formula (V) or any variations thereof can be synthesized using methods known in the art, for example, the synthetic methods described in WO 2005/121142 A1, incorporated herein by reference.

In some embodiments, the MEK inhibitor is a compound of formula (VI),

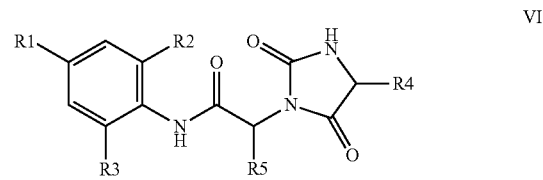

or a pharmaceutically acceptable salt or ester thereof, wherein:

R1 is selected from the group consisting of bromo, iodo, ethynyl, cycloalkyl, alkoxy, azetidinyl, acetyl, heterocycyl, cyano, straight-chained alkyl and branched-chain alkyl;

R2 is selected from the group consisting of hydrogen, chlorine, fluorine, and alkyl;

R3 is selected from the group consisting of hydrogen, chlorine, and fluorine;

R4 is selected from the group consisting of hydrogen, optionally substituted aryl, alkyl, and cycloalkyl;

R5 is selected from the group consisting of hydrogen and

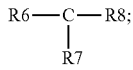

wherein R6 is selected from the group consisting of hydroxyl, alkoxy, cycloalkyl, optionally substituted alkyl, optionally substituted aryl, and optionally substituted heteroaryl;

R7 and R8 are independently selected from the group consisting of hydrogen and optionally substituted alkyl;

or R6 and R7 can together form a cycloalkyl group and R8 is hydrogen.

In some variations, the MEK inhibitor compound is of the formula (VI), or a pharmaceutically acceptable salt or ester thereof, wherein the variables are as defined in WO 2007/096259 A1 for the formula I or any applicable variations described on pages 4-10 in WO 2007/096259 A1, incorporated herein by reference. Further embraced MEK inhibitors are compounds described in Examples 1-182 in WO 2007/096259 A1, incorporated herein by reference.

In some embodiments, the MEK inhibitor compound of the formula (VI) is a compound selected from the group consisting of:
(2S,3S)—N-(4-Bromo-phenyl)-2-[(R)-4-(4-methoxy-phenyl)-2,5-dioxo-imidazolidin-1-yl]-3-phenyl-butyramide;
(2S,3S)—N-(4-Iodo-phenyl)-2-[(R)-4-(4-methoxy-phenyl)-2,5-dioxo-imidazolidin-1-yl]3-phenyl-butyramide;
(2S,3S)—N-(2-Fluoro-4-iodo-phenyl)-2-{(R)-4-[4-(2-hydroxy-ethoxy)-phenyl]-2,5-dioxo-imidazolidin-1-yl}-3-phenyl-butyramide;
(2S,3S)—N-(4-Ethynyl-2-fluoro-phenyl)-2-{(R)-4-[4-(2-hydroxy-ethoxy)-phenyl]-2,5-dioxo-imidazolidin-1-yl}-3-phenyl-butyramide;

(2R,3S)—N-(4-Ethynyl-2-fluoro-phenyl)-2-{(R)-4-[4-(2-hydroxy-ethoxy)-phenyl]-2,5-dioxo-imidazolidini-1-yl}-3-phenyl-butyramide;
(2S,3S)—N-(2-Chloro-4-iodo-phenyl)-2-{(R)-4-[4-(2-hydroxy-ethoxy)-phenyl]-2,5-dioxo-imidazolidin-1-yl}-3-phenyl-butyramide;
(2S,3S)-2-{(R)-4-[4-(2-Hydroxy-ethoxy)-phenyl]-2,5-dioxo-imidazolidin-1-yl)}-N-(4-iodo-2-methyl-phenyl)-3-phenyl-butyramide;
(2S,3S)—N-(2-Chloro-4-iodo-phenyl)-2-{(R)-4-[4-((R)-2,3-dihydroxy-propoxy)-phenyl]-2,5-dioxo-imidazolidin-1-yl}-3-phenyl-butyramide;
(2S,3S)—N-(2-Chloro-4-iodo-phenyl)-2-{(R)-4-[4-((S)-2,3-di hydroxy-propoxy)-phenyl]-2,5-dioxo-imidazolidin-1-yl}-3-phenyl-butyramide;
(2S,3S)-2-{(R)-2,5-Dioxo-4-[4-(2-oxo-2-pyrrolidin-1-yl-ethoxy)-phenyl]-imidazolidin-1-yl}-N-(2-fluoro-4-iodo-phenyl)-3-phenyl-butyramide;
(2S,3S)-2-((R)-2,5-Dioxo-4-thiophen-3-yl-imidazolidin-1-yl)-N-(4-iodo-phenyl)-3-phenyl-butyramide;
(S)-2-[(R)-4-(2,3-Dihydro-benzo[1,4]dioxin-6-yl)-2,5-dioxo-imidazolidin-1-yl]-N-(2-fluoro-4-iodo-phenyl)-3-phenyl-propionamide;
(S)-2-[(R)-4-(4-Acetylamino-phenyl)-2,5-dioxo-imidazolidin-1-yl]-N-(2-fluoro-4-iodo-phenyl)-3-phenyl-propionamide;
(4-{(R)-1-[(1S,2S)-1-(2-Fluoro-4-iodo-phenylcarbamoyl)-2-phenyl-propyl]-2,5-dioxo-imidazolidin-4-yl}-phenoxymethyl)-phosphonic acid dimethyl ester;
(2S,3S)—N-(2-Fluoro-4-iodo-phenyl)-2-((R)-4-isopropyl-2,5-dioxo-imidazolidin-1-yl)-3-phenyl-butyramide;
(S)—N-(2-Fluoro-4-iodo-phenyl)-2-{(R)-4-[4-(2-hydroxy-ethoxy)-phenyl]-2,5-dioxo-imidazolidin-1-yl}=3-methyl-butyramide;
(S)—N-(2-Fluoro-4-iodo-phenyl)-2-[(R)-4-(4-methoxy-phenyl)-2,5-dioxo-imidazolidin-1-yl]-3-o-tolyl-propionamide;
(S)—N-(2-Fluoro-4-iodo-phenyl)-2-[(R)-4-(4-methoxy-phenyl)-2,5-dioxo-imidazolidin-1-yl]-3-m-tolyl-propionamide;
(S)—N-(2-Fluoro-4-iodo-phenyl)-2-[(R)-4-(4-methoxy-phenyl)-2,5-dioxo-imidazolidin-1-yl]-3-p-tolyl-propionamide; and
(S)—N-(4-Cyclopropyl-2-fluoro-phenyl)-3-(4-fluoro-phenyl)-2-{(R)-4-[4-(2-hydroxy-1-hydroxymethyl-ethoxy)-phenyl]-2,5-dioxo-imidazolidin-1-yl}-propionamide;
or a pharmaceutically acceptable salt or ester thereof.

In some embodiments, the MEK inhibitor is a compound of formula (VII),

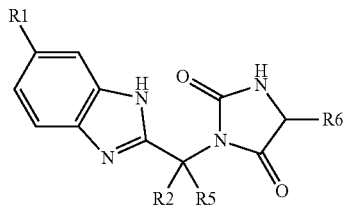

VII or a pharmaceutically acceptable salt or ester thereof, wherein:
R1 is selected from the group consisting of halogen, ethynyl, and cycloalkyl;
R2 is selected from the group consisting of hydrogen and CH(R3)(R4);
R3 is selected from the group consisting of lower alkyl, lower alkoxy, optionally substituted aryl, and optionally substituted heteroaryl;
R4 is selected from the group consisting of hydrogen and lower alkyl;
R5 is hydrogen or, taken together with R2 and the carbon to which R2 and R5 are attached, forms lower cycloalkyl; and
R6 is selected from the group consisting of hydrogen, lower alkyl, lower cycloalkyl, optionally substituted aryl, and optionally substituted heteroaryl.

In some variations, the MEK inhibitor compound is of the formula (VI), or a pharmaceutically acceptable salt or ester thereof, wherein the variables are as defined in WO 2009/021887 A1 for the formula I or any applicable variations described on pages 4-5 in WO 2009/021887 A1, incorporated herein by reference. Further embraced MEK inhibitors are compounds described in Examples 1-21 in 2009/021887 A1, incorporated herein by reference.

In some embodiments, the MEK inhibitor compound of the formula (VI) is a compound selected from the group consisting of:
(R)-5-[4-(2-Hydroxy-ethoxy)-phenyl]-3-[(S)—-(6-iodo-1H-benzoimidazol-2-yl)-2-phenyl-ethyl]-imidazolidine-2,4-dione;
(R)-5-[4-(2-Hydroxy-ethoxy)-phenyl]-3-(5-iodo-1H-benzoimidazol-2-ylmethyl)-imidazolidine-2,4-dione;
(R)-5-[4-(2-Hydroxy-ethoxy)-phenyl]-3-[(S)-1-(5-iodo-1H-benzoimidazol-2-yl)-2-methyl-propyl]-imidazolidine-2,4-dione;
(R)-5-[4-(2-Hydroxy-ethoxy)-phenyl]-3-[(1R,2R)-1-(5-iodo-1H-benzoimidazol-2-yl)-2-methoxy-propyl]-imidazolidine-2,4-dione;
3-[(S)-1-(5-Iodo-1H-benzoimidazol-2-yl)-2-phenyl-ethyl]-imidazolidine-2,4-dione; compound with trifluoro-acetic acid;
(R)-3-[(S)-2-(4-Fluoro-phenyl)-1-(5-iodo-1H-benzoimidazol-2-yl)-ethyl]-5-[4-(2-hydroxy-ethoxy)-phenyl]-imidazolidine-2,4-dione;
(R)-5-[4-(2-Hydroxy-ethoxy)-phenyl]-3-[(S)-1-(5-iodo-1H-benzoimidazol-2-yl)-2-(4-methoxy-phenyl)-ethyl]-imidazolidine-2,4-dione;
(R)-5-[4-(2-Hydroxy-ethoxy)-phenyl]-3-[(S)-1-(5-iodo-1H-benzoimidazol-2-yl)-2-thiophen-2-yl-ethyl]-imidazolidine-2,4-dione;
(R)-3-[(1S,2S)-1-(6-Iodo-1H-benzoimidazol-2-yl)-2-phenyl-propyl]-5-phenyl-imidazolidine-2,4-dione;
(R)-3-[(1S,2S)-1-(6-Iodo-1H-benzoimidazol-2-yl)-2-phenyl-propyl]-5-(4-methoxy-phenyl)-imidazolidine-2,4-dione;
(R)-5-[4-(2-Hydroxy-ethoxy)-phenyl]-3-[(1S,2S)-1-(6-iodo-1H-benzoimidazol-2-yl)-2-phenyl-propyl]-imidazolidine-2,4-dione;
(R)-3-[(1S,2S)-1-(6-Iodo-1H-benzoimidazol-2-yl)-2-phenyl-propyl]-5-[4-(2-methoxy-ethoxy)-phenyl]-imidazolidine-2,4-dione;
2-(4-{(R)-1-[(1S,2S)-1-(6-Iodo-1H-benazoimidazol-2-yl)-2-phenyl-propyl]-2,5-dioxo-imidazolidin-4-yl)}-phenoxy)-N,N-dimethyl-acetamide;
N,N-Bis-(2-hydroxy-ethyl)-2-(4-{(R)-1-[(1S,2S)-1-(6-iodo-1H-benzoimidazol-2-yl)-2-phenyl-propyl]-2,5-dioxo-imidazolidin-4-yl}-phenoxy)-acetamide;
(R)-3-[(1S,2S)-1-(5-Iodo-1H-benzoimidazol-2-yl)-2-phenyl-propyl]-5-isopropyl-imidazolidine-2,4-dione;
(R)-5-Cyclohexyl-3-[(1S,2S)-1-(5-iodo-1H-benzoimidazol-2-yl)-2-phenyl-propyl]-imidazolidine-2,4-dione;

(R)-5-[4-(2-Hydroxy-ethoxy)-phenyl]-3-[1-(5-iodo-1H-benzoimidazol-2-yl)-cyclopropyl]-imidazolidine-2,4-dione;

(R)-3-[(1S,2S)-1-(6-Bromo-1H-benzoimidazol-2-yl)-2-phenyl-propyl]-5-[4-(2-hydroxy-ethoxy)-phenyl]-imidazolidine-2,4-dione;

(R)-3-[(S)-1-(5-Cyclopropyl-1H-benzoimidazol-2-yl)-2-phenyl-ethyl]-5-[4-(2-hydroxy-ethoxy)-phenyl]-imidazolidine-2,4-dione;

(R)-3-[(S)-1-(5-Ethynyl-1H-benzoimidazol-2-yl)-2-phenyl-ethyl]-5-[4-(2-hydroxy-ethoxy)-phenyl]-imidazolidine-2, 4-dione; and (R)-3-[(1S,2S)-1-(5-Ethynyl-1H-benzoimidazol-2-yl)-2-phenyl-propyl]-5-[4-(2-hydroxy-ethoxy)-phenyl]-imidazolidine-2,4-dione;

or a pharmaceutically acceptable salt or solvate thereof.

In some embodiments, the MEK inhibitor is a compound selected from the group consisting of GDC-0973 (Methanone, [3,4-difluoro-2-[(2-fluoro-4-iodophenyl)amino]phenyl][3-hydroxy-3-(2S)-2-piperidinyl-1-azetidinyl]-), G-38963, G02443714, G02442104, and G00039805, or a pharmaceutically acceptable salt or solvate thereof.

GDC-0973

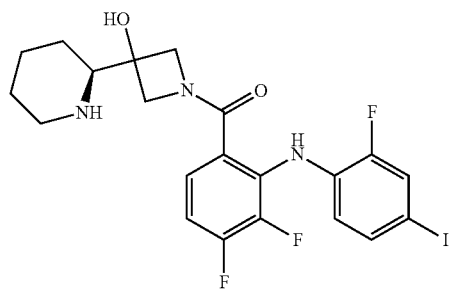

G-38963

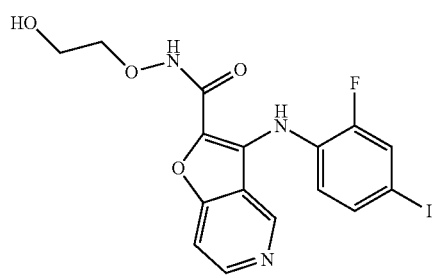

G02443714

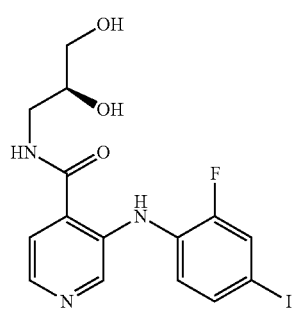

G02442104

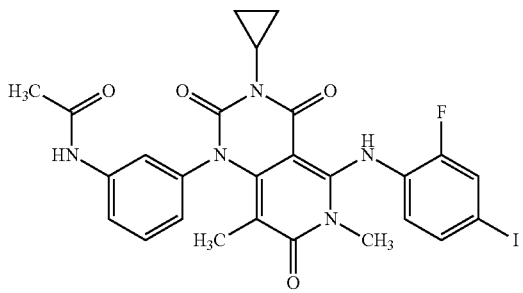

G00039805

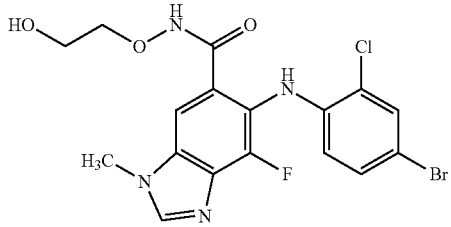

IV Kits

In another aspect, provided is a kit comprising a PD-L axis binding antagonist and/or a MEK inhibitor for treating or delaying progression of a cancer in an individual or for enhancing immune function of an individual having cancer. In some embodiments, the kit comprises a PD-1 axis binding antagonist and a package insert comprising instructions for using the PD-1 axis binding antagonist in combination with a MEK inhibitor to treat or delay progression of cancer in an individual or to enhance immune function of an individual having cancer. In some embodiments, the kit comprises a MEK inhibitor and a package insert comprising instructions for using the MEK inhibitor in combination with a PD-1 axis binding antagonist to treat or delay progression of cancer in an individual or to enhance immune function of an individual having cancer. In some embodiments, the kit comprises a PD-1 axis binding antagonist and a MEK inhibitor, and a package insert comprising instructions for using the PD-1 axis binding antagonist and the MEK inhibitor to treat or delay progression of cancer in an individual or to enhance immune function of an individual having cancer. Any of the PD-1 axis binding antagonists and/or MEK inhibitors described herein may be included in the kits.

In some embodiments, the kit comprises a container containing one or more of the PD-1 axis binding antagonists and MEK inhibitors described herein. Suitable containers include, for example, bottles, vials (e.g., dual chamber vials), syringes (such as single or dual chamber syringes) and test tubes. The container may be formed from a variety of materials such as glass or plastic. In some embodiments, the kit may comprise a label (e.g., on or associated with the container) or a package insert. The label or the package insert may indicate that the compound contained therein may be useful or intended for treating or delaying progression of cancer in an individual or for enhancing immune function of an individual having cancer. The kit may further comprise other materials desirable from a commercial and user standpoint, including other buffers, diluents, filters, needles, and syringes.

EXAMPLES

The invention can be further understood by reference to the following examples, which are provided by way of illustration and are not meant to be limiting.

Example 1

MEK Inhibitor Enhanced MHC I Expression on Tumor Cell Lines

Figure 2:
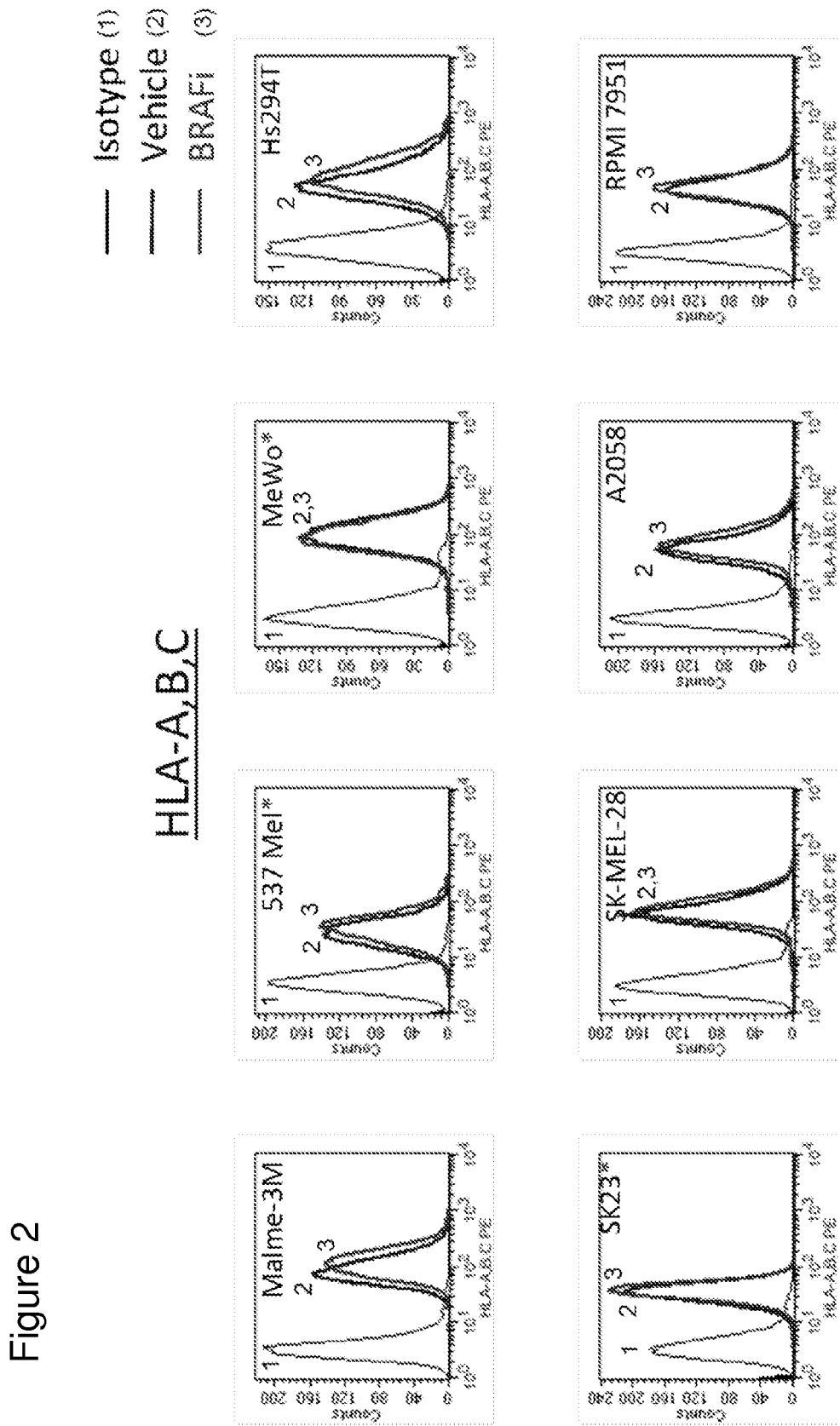
FIG. 2 is a histogram showing that treatment of human melanoma cell lines (5/8 cell lines of which were BRAF mutant; BRAF wild-type cells indicated with asterisk) with BRAF inhibitor did not upregulate MHC I surface expression.

To determine if treatment with MEK inhibitor (MEKi) enhanced immunogenicity of tumor cells, surface expression of MHC-I on tumor cell lines treated with MEK inhibitors GDC-0973 and G-38963 was assayed. Briefly, human melanoma cell lines (Malme-3M, A2058, A375, HS294T, SK23, SKMEL-28, 537 Mel, RPMI-795) and human colorectal cell lines (Colo 320 DM, Colo 205, WiDr, Colo 741, RKO, DLD-1, HM7, HCT-15) were treated with 1 micromolar MEKi GDC-0973 or G-38963, BRAF inhibitor (BRAFi) GDC-0879, or DMSO vehicle for 24 hours. Following treatment, cells were stained for surface MHC Class I expression with an antibody against HLA-A,B,C for subsequent FACS analysis. Data shown is for treatment with MEKi GDC-0973. Labeled isotype-matched antibodies were used to determine the level of non-specific staining. Data analysis and construction of histograms demonstrated that cell surface expression of MHC-I was upregulated in MEKi treated cells as compared to vehicle treated cells (FIG. 1A). In contrast, cell surface expression of MHC-I in BRAFi treated cells was not upregulated as compared to vehicle treated cells (FIG. 2). These results demonstrate that enhanced cell surface expression of MHC-I in both melanoma and colorectal tumor cells is specific to MEK inhibition and not due to general inhibition of the RAS/RAF/MEK signaling pathway.

To determine if treatment with MEK inhibitor (MEKi) enhanced immunogenicity of mouse tumor cells similarly to human tumor cells, surface expression of MHC-I on mouse tumor cell lines treated with MEKi GDC-0973 was assayed. Briefly, mouse melanoma cell lines (MC38 and B16.F10) and a mouse colorectal cell line (CT26) were treated with MEKi GDC-0973, G-38963 or vehicle. Briefly, cells were stimulated for 24 hours with 1 micromolar MEK inhibitor or DMSO vehicle control. Following treatment, cells were surfaced stained with an antibody against MHC-I (H-2D) and expression was assayed by subsequent FACS analysis. Labeled isotype-matched antibodies were used to determine the level of non-specific staining. Data analysis and construction of histograms demonstrated that cell surface expression of MHC-I was upregulated in MEKi treated cells (data shown is for MEKi GDC-0973) as compared to vehicle treated cells (FIG. 1B). These results demonstrate that enhanced cell surface expression of MHC-I occurred across several melanoma and colorectal tumor cell lines regardless of mouse or human origin.

Figure 3:
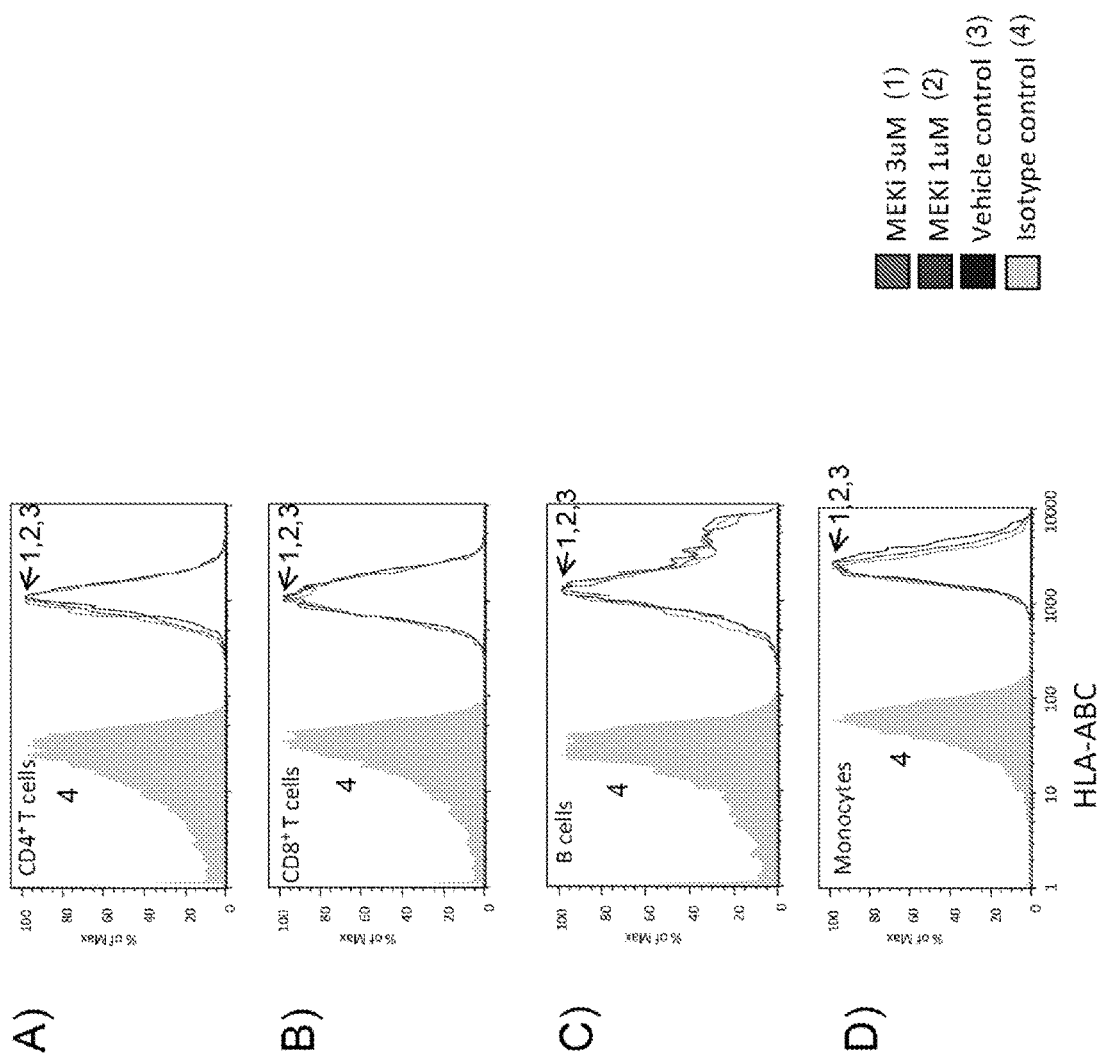
FIG. 3 shows that treatment of human peripheral blood mononuclear cells with MEK inhibitor did not upregulate MHC I surface expression. (A-D) Histogram showing unaltered MHC I surface expression in CD4+ T cells, CD8+ T cells, B cells, or monocytes upon MEK inhibitor treatment.

To determine if enhanced cell surface expression of MHC-I is specific to tumor cells, the effect of MEKi treatment on MHC-I expression on human peripheral blood mononuclear cells (PMBCs) was assayed. Briefly, PMBCS were isolated from whole blood by first diluting it with an equal volume of room temperature PBS and subsequent overlay onto Ficoll-filled Leucosep tubes (Greiner Bio-One). Post-centrifugation, the PBMC interface was then washed twice and resuspended in culture media (RPMI-1640 with 10% fetal bovine serum, 20 µM HEPES, 55 µM 2-mercaptoethanol, 50 µg/ml gentamicin, and 1:100 dilutions of the following supplements from Gibco: Gluta-MAX, sodium pyruvate, penicillin/streptomycin, and non-essential amino acids). Cells were plated in 6 well plates at $4 \times 10^6$ per well with a total of 4 ml per well. MEK inhibitor GDC-0973 was added at either 1 µM or 3 µM. Cells were harvested 24 hours later and distributed to a 96-well V-bottom plate for FACS staining. Cells were stained with the following antibodies (all from BD Biosciences, at 1:10 for 30 minutes on ice): CD3-FITC, HLA-ABC-PE, CD4-APC, CD19-FITC, and CD14-FITC. Propidium iodide was included to exclude dead cells. Samples were run on a BD FACSCaliber flow cytometer and data was analyzed using FlowJo software (Tree Star, Inc.). Data analysis and construction of histograms demonstrated that cell surface expression of MHC-I was not upregulated in CD4+ T cells (FIG. 3A), CD8+ T cells (FIG. 3B), B cells (FIG. 3C), or monocytes (FIG. 3D) treated with 1 µM MEKi GDC-0973 or 3 µM MEKi GDC-0973 as compared to vehicle treated cells. These results demonstrate that enhanced cell surface expression of MHC-I by MEK inhibitor treatment is specific to tumor cells.

Example 2

Figure 4:
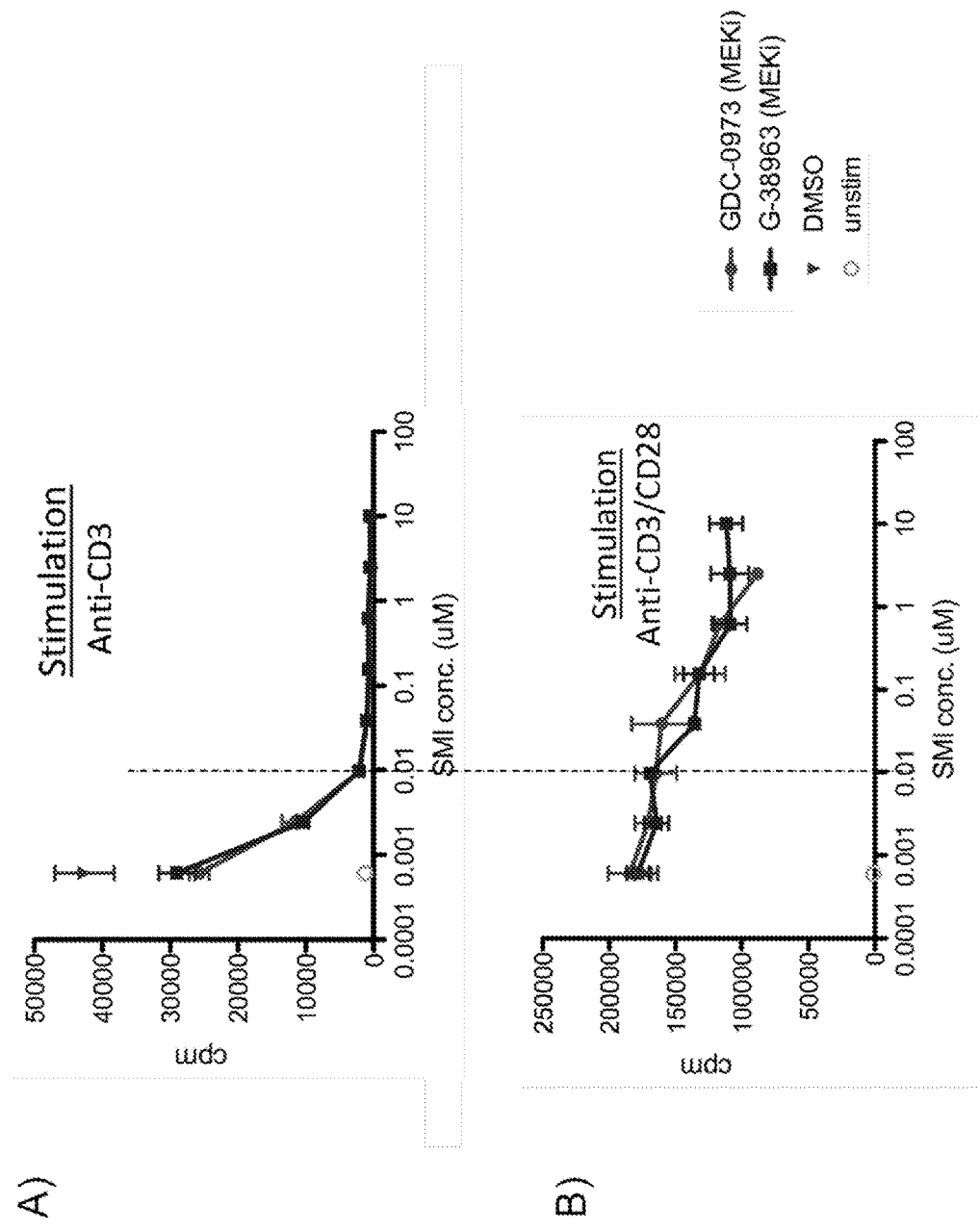
FIG. 4 demonstrates that co-stimulatory signals make T cells responsive despite MEK inhibitor treatment. (A) Graph of $CD8^+$ T cells levels shows that MEK inhibitor treatment reduced T cell proliferation and activation normally induced by stimulation of CD3. (B) Graph of $CD8^+$ T cells show that co-stimulation of CD3 and CD28 was sufficient to overcome the inhibitory effect of MEK inhibitor treatment.

Co-Stimulatory Signals Made T Cells Resistant to TCR Signaling Inactivation by MEK Inhibitor Recent studies have shown that MEK inhibitor treatment impairs T lymphocyte function (Boni et al., *Cancer Res.*, 70(13), 2010). To confirm that MEK inhibitor treatment impaired CD8+ T cells, T cells were treated with MEKi in combination with T cell stimulation signals and assayed for T cell proliferation. Briefly, human CD8+ T cells were purified from whole blood using StemCell Technologies human CD8 RosetteSep as per manufacturer's instructions. Purified cells were plated at 200,000 per well in triplicate in 96-well U-bottom plates with 200,000 per well of either anti-CD3 or anti-CD3/anti-CD28 Dynabeads (Invitrogen). MEK inhibitors GDC-0973 and G-38963 were titrated 10-fold from 10 µM to 0.001 µM such that the final culture concentration was 0.5% DMSO in a total volume of 200 µl per well. Culture medium was RPMI-1640 with 10% fetal bovine serum, 20 µM HEPES, 55 µM 2-mercaptoethanol, 50 µg/ml gentamicin, and 1:100 dilutions of the following supplements from Gibco: Gluta-MAX, sodium pyruvate, penicillin/streptomycin, and non-essential amino acids. At 48 hours, wells were pulsed with 1 µCi/well of 3H-thymidine and cultured an additional 16 hours prior to freezing and harvest. Data analysis demonstrated that treatment of CD8+ T cells with anti-CD3 stimulated T cell activation (closed triangle) as compared to unstimulated T cells (open circle). Treatment of T cells with two different MEK inhibitors reduced the stimulatory effect of anti-CD3 (closed circle, closed square) at all MEKi concentrations tested, with nearly complete inhibition of T cell receptor induced proliferation occurring at 0.01 µM MEKi treatment (FIG. 4A). In contrast, co-stimulation with anti-CD3 and anti-CD28 in MEKi treated T cells (closed circle, closed square) was sufficient to overcome the inhibitory effect of MEKi on T cell activation (FIG. 4B). These unexpected results demonstrate the novel finding that inhibition of TCR signaling by MEKi treatment can be overcome by providing sufficient T cell co-stimulation which is provided to T cells by antigen presenting cells such as B cells, macrophages, and dendritic cells.

Without being bound to theory, a key component of co-stimulation is thought to be the activation of PI3 kinase and is provided by CD28 via association of PI3K p85 subunit with its cytoplsmic YMNM motif. PD-1, through its interaction with SHP2, impedes the activity of PI3K. Therefore, blockade of the PDI axis may disinhibit PI3kinase, resulting in enhanced T cell costimulation and provides a means to overcome the inhibitory effect of MEKi on T cell activation. PD-1/-L1 blockade is to enhance co-stimulation under conditions when expression of co-stimulatory ligands such as B7.1 and B7.2 is often limiting such as in most tumors or the tumor microenvironment. Combining MEKi with blockade of the PDI axis should enhance tumor specific T cell immunity by enhancing Ag recognition by the TCR through upregulation of tumor MHC I (enhancing Signal I) by MEKi and by relieving inhibition of PI3K (enhancing Signal 2) through PD1/PDL1 blockade.

Example 3

Figure 5:
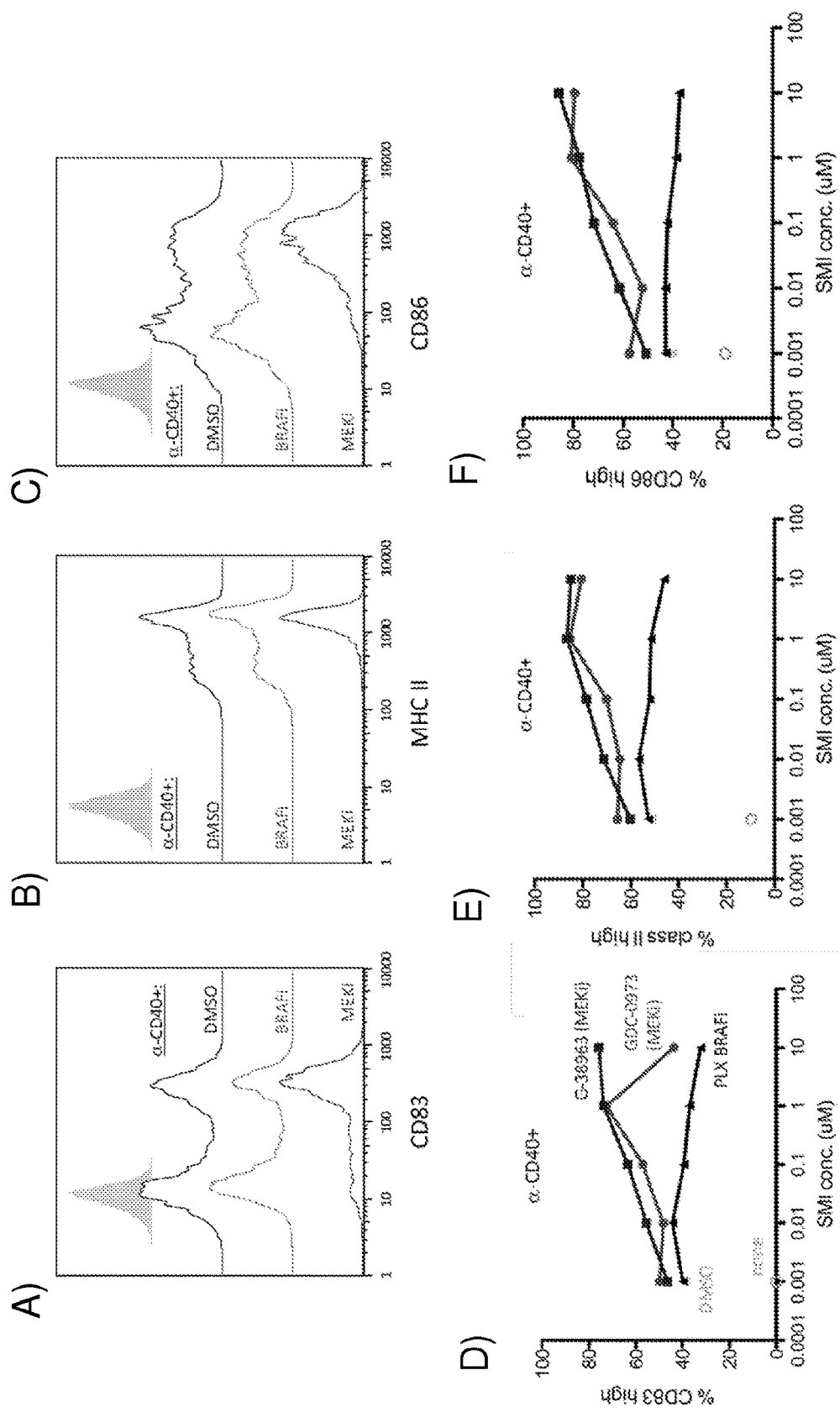
FIG. 5 shows that MEK inhibitor treatment enhanced maturation and activation of dendritic cells stimulated with anti-CD40 antibodies. (A-C) Histogram showing dendritic cells stimulated with anti-CD40 antibodies and treated with MEK or BRAF inhibitor. MEK inhibitor enhanced DC activation as evidenced by upregulation of DC surface activation markers CD83, MHC II and CD86. (D-F) Graphs of activated dendritic cell levels demonstrates that MEK inhibitor enhanced DC activation in a dose dependent manner.

MEK Inhibitor Specifically Enhanced Maturation and Activation of Dendritic Cells To determine if MEK inhibitor treatment specifically enhanced tumor immunogenicity by stimulating dendritic cells (DCs), monocyte-derived dendritic cells were treated with increasing concentration of MEKi GDC-0973, MEKi GDC-38963 or BRAFi GDC-0879 in combination with antibodies to the DC co-stimulatory molecule CD40. Briefly, human monocytes were purified from whole blood using StemCell Technologies human monocyte RosetteSep as per manufacturer's instructions. Monocytes were seeded in T175 flasks at approximately $0.5$-$1.0 \times 10^6$ per ml in 50 ng/ml human GM-CSF and 100 ng/ml human IL-4 for 7 days total, with half-media exchanges every 2 days. Cells were then harvested and plated at 100,000 cells/well in 96-well flat bottom plates with or without Pfizer anti-CD40 at 1 μg/ml. MEK inhibitors and BRAF inhibitor were titrated 10-fold from 10 μM to 0.001 μM such that the final culture concentration was 0.5% DMSO in a total volume of 200 μl per well. Forty-eight hours later, cells were harvested and transferred to a 96-well V-bottom plate. Cells were first Fc-receptor blocked (Miltenyi) and then stained using the following antibodies (from BD Biosciences at 1:10, 30 minutes on ice): HLA-DR,-DP,-DQ-FITC, HLA-ABC-PE, CD83-APC, CD14-FITC, CD80-PE, and CD86-APC. Propidium iodide was included to exclude dead cells. Samples were run on a BD FACSCaliber flow cytometer and data was analyzed using FlowJo software (Tree Star, Inc.). Data analysis and construction of histograms demonstrated that the frequency of cells expressing the maturation marker CD83 (FIG. 5A), MHC-II (FIG. 5B), and co-stimulatory molecule CD86 (FIG. 5C) was increased in cells treated with 1 μM MEKi GDC-0973 as compared to vehicle treated cells. In contrast, cell surface expression of these DC surface activation markers in DCs treated with 1 μM BRAFi was not upregulated and was similar to vehicle treated cells. Furthermore, increasing concentrations of either MEKi G-38963 (closed square) or MEKi GDC-0973 (closed circle) enhanced the frequency of DCs expressing these surface markers of DC maturation and activation in concentration dependent manner (FIG. 5D-SF). In contrast BRAFi (closed triangle) treatment did not enhance the anti-CD40 co-stimulatory effect. These novel results demonstrate that enhanced maturation and activation of DCs is specific to MEK inhibitor treatment and not due to general inhibition of the RAS/RAF/ MEK signaling pathway. Furthermore, MEKi enhanced activation of human monocyte-derived DCs co-stimulated with anti-CD40 in a concentration dependent manner indicating that MEKi may have an immunomodulatory effect on DCs.

Example 4

Figure 6:
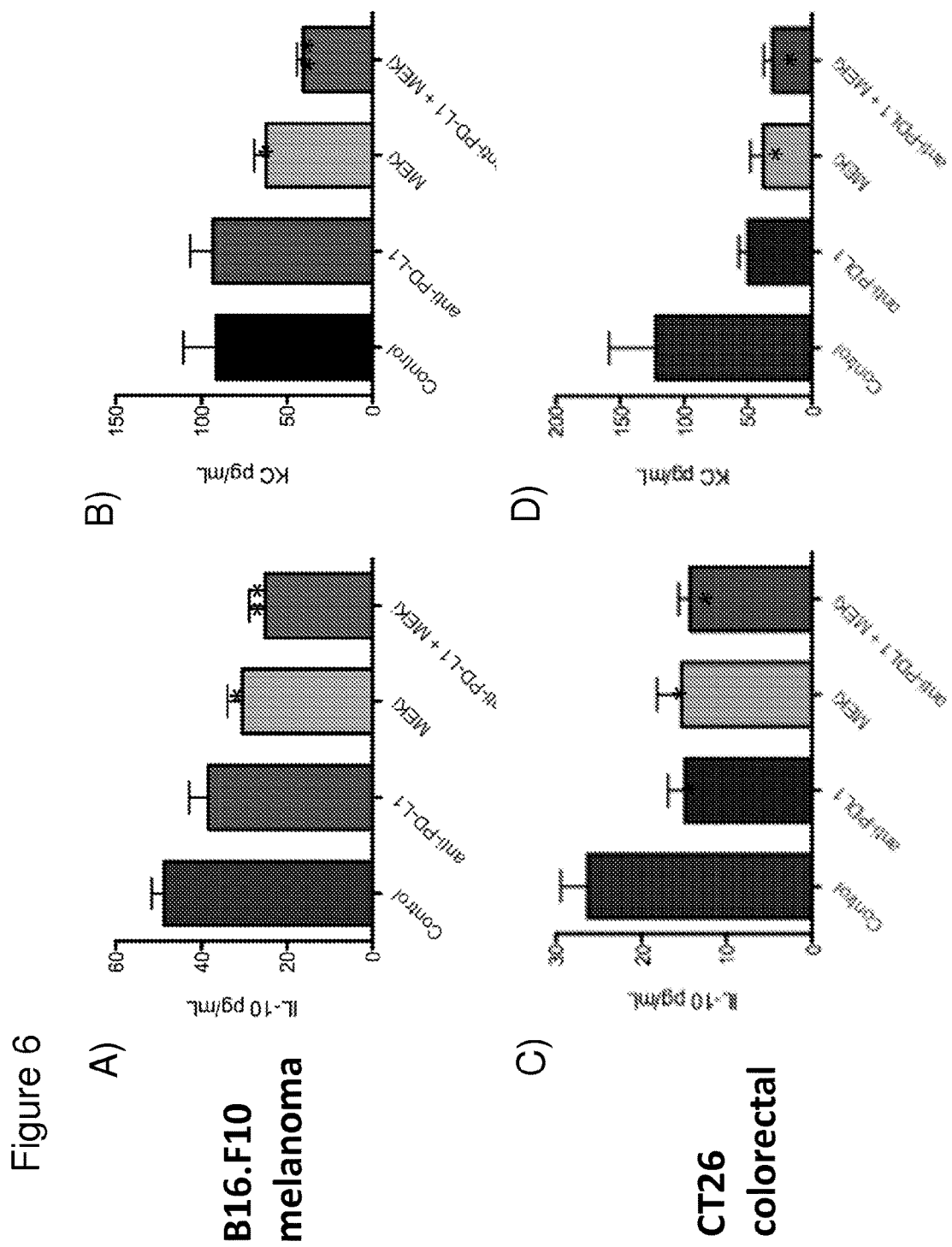
FIG. 6 is a graph showing reduced serum levels of immunosuppressive and pro-tumor cytokines in in vivo models of cancer. (A and C) Immunosuppressive cytokine IL-10 was decreased 7 days following co-treatment with anti-PD-L1 antibodies and MEK inhibitor as compared to treatment with anti-PD-L1 or MEK inhibitor treatment alone. (B and D) The pro-tumor chemokine KC was decreased upon co-treatment with anti-PD-L1 antibodies and MEK inhibitor as compared to treatment with anti-PD-L1 or MEK inhibitor treatment alone.

Co-Treatment with MEK Inhibitor and Anti-PD-L1 Antibodies Reduced Serum Levels of Cytokines that Promote Tumor Growth Due to the novel observation that MEKi treatment enhanced T cell and DC activation in the presence of a co-stimulator, MEKi G-38963 was used in combination with anti-PD-L1 antibodies to determine if MEKi could enhance the anti-tumor effects of anti-PD-L1 antibody treatment and modulate cytokine levels in tumor bearing animals. The anti-PD-L1 antibody employed in these experiments was PRO314483, LOT#59554.96, raised against human PD-L1 and recognizes both human and murine PD-L. Briefly, 7 days after treatment, mice were anaesthetized and bled retro-orbitally for serum. Analysis for serum levels of cytokines was conducted using the BioRad Bio-Plex assay and it was determined that the immunosuppressive cytokine IL-10 was significantly reduced in in vivo models for both melanoma (FIG. 6A) and colorectal (FIG. 6C) tumors. IL-10 levels were decreased with anti-PD-L1 antibody or MEKi treatment alone but were significantly reduced by co-treatment with MEKi and anti-PD-L1 antibodies. Furthermore, serum levels of the murine chemokine KC, homolog of the human chemokine IL-8 that is known to play a role in tumor progression, was also significantly reduced in in vivo models for both melanoma (FIG. 6B) and colorectal (FIG. 6D) tumors with the most significant reduction induced by co-treatment with MEKi and anti-PD-L1 antibodies. These results indicate that combination treatment of anti-PD-L1 antibodies and MEKi inhibits release of cytokines that promote tumor growth.

Example 5

Figure 7:
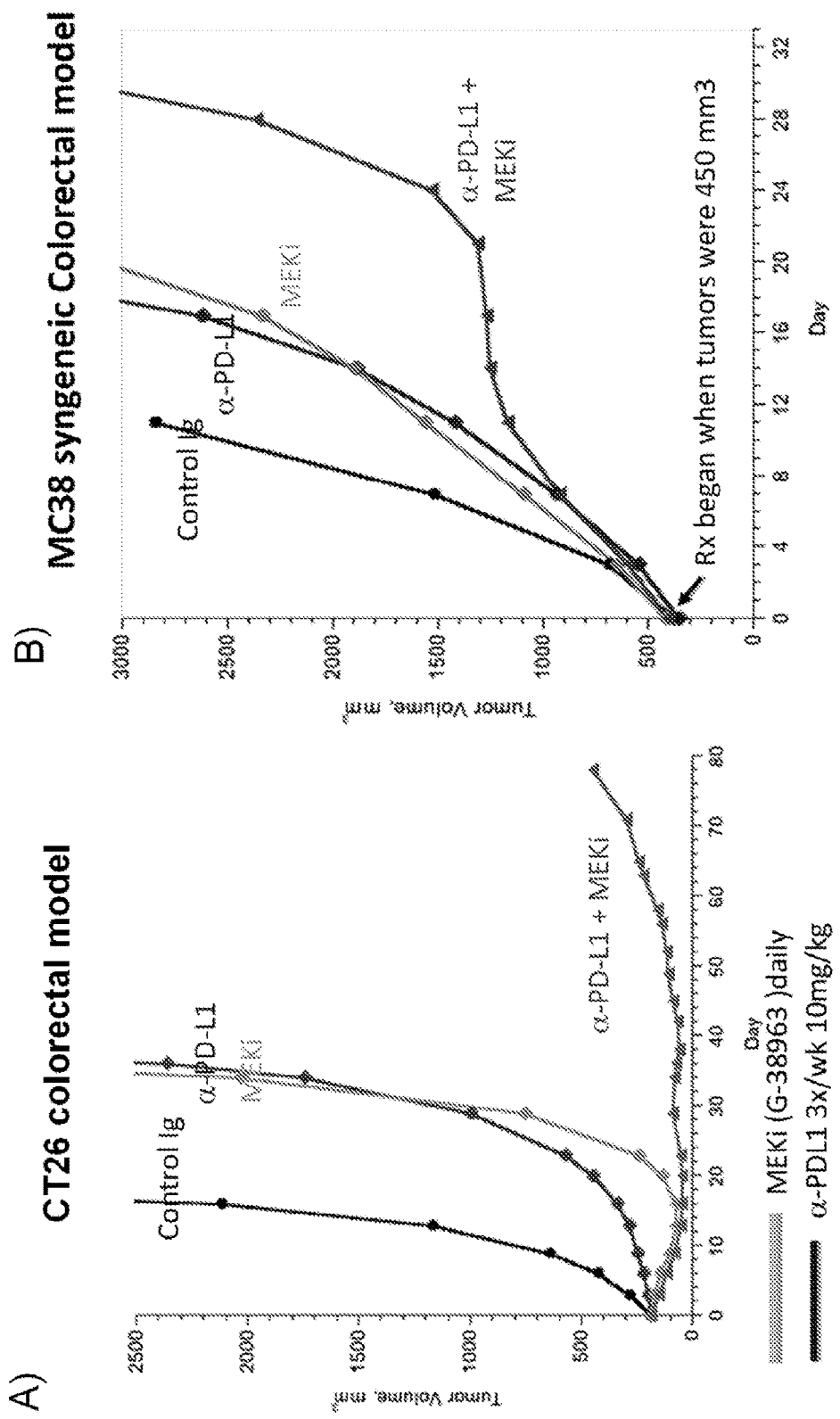
FIG. 7 demonstrates that MEK inhibitor treatment enhanced anti-tumor activity of anti-PD-L1 antibodies in in vivo models of colorectal cancer. (A) Graph depicting changes in tumor volume with anti-PD-L1 antibodies and MEK inhibitor co-treatment demonstrate a significant reduction of early stage tumor growth and sustained anti-tumor effect as compared to anti-PD-L1 antibodies or MEK inhibitor treatment alone. (B) Graph depicting changes in tumor volume with anti-PD-L1 antibodies and MEK inhibitor co-treatment demonstrate a significant inhibition of late stage tumor growth as compared to anti-PD-L1 antibodies or MEK inhibitor treatment alone.

MEK Inhibition Enhanced Anti-Tumor Activity of Anti-PD-L1 Antibodies in Colorectal Tumors In Vivo To determine if MEKi enhanced the anti-tumor effect of anti-PD-L1 antibodies, mouse models for colorectal tumors were treated with the combination treatment. Briefly, mice were inoculated subcutaneously with tumor cells and allowed to grow tumors. When tumor bearing mice achieved a mean tumor volume of 200 mm3 (FIG. 7A) or 450 mm3 (FIG. 7B), mice were randomly assigned to 1 of 4 treatment groups. Group 1: received 10 mg/kg of an isotype control antibody (anti-gp120, PRO67181, PUR#20455) intraperitoneally three times a week for 3 weeks plus MCT control vehicle, orally, daily for 21 days; Group 2: received 10 mg/kg anti-PD-L1 antibody PRO314483, LOT#59554.96 intraperitoneally three times a week for three weeks; Group 3: received 10 mg/kg of an isotype control antibody (anti-gp120, PRO67181, PUR#20455) intraperitoneally 3×/week×3 plus 75 mg/kg MEKi G-38963, orally, daily for 21 days; Group 4: received 10 mg/kg of an anti-PD-L1 antibody PRO314483, LOT#59554.96 intraperitoneally three times a week for three weeks plus 75 mg/kg MEKi G-38963, orally, daily for 21 days. Mice were monitored for tumor growth and body weight changes. Blockade of PD-L1 with anti-PD-L1 antibody PRO314483, LOT#5944.96 either in early (FIG. 7A) or in late (FIG. 7B) intervention was highly effective as a single agent therapy at preventing tumor growth. Treatment with MEKi G-38963 was also highly effective as a single agent therapy at preventing tumor growth either in early or in late intervention and was comparable to anti-PD-L1 antibody treatment. Combination treatment with anti-PD-L1 antibodies and MEKi significantly inhibited tumor growth both in early and late intervention and was significantly more effective than anti-PD-L1 antibodies or MEKi treatment alone. Furthermore, co-treatment at an early stage of tumor growth resulted not only in significant reduction of tumor volume but also demonstrated a sustained response. Early intervention resulted in about a 60% complete response that was maintained for at least 92 days. These results indicate that MEKi enhanced the anti-tumor activity of PD-L1 blockade and therefore worked synergistically with anti-PD-L1 antibodies to inhibit tumor growth.

To further determine if MEKi enhanced the anti-tumor effect of anti-PD-L1 antibodies, mouse models for colorectal tumors were treated with the combination treatment using a different MEK inhibitor, MEKi GDC-0973, in two different studies.

For the first study, female BALB/c mice were inoculated subcutaneously in the unilateral thoracic region with 100,000 CT26 murine colorectal cells in 100 µL of HBSS:matrigel. When mice achieved a mean tumor volume of approximately 200 mm3, they were randomly assigned to one of nine different treatment groups on experimental day 0 and treatment was initiated on experimental day 1. Groups of 10 mice were orally given the following in a volume of 200 µl daily for 21 days: Group 1 received MCT vehicle; Group 2 received 0.5 mg/kg GDC-0973; Group 3 received 1.0 mg/kg GDC-0973; Group 4 received 2.0 mg/kg GDC-0973; Group 5 received 3.0 mg/kg GDC-0973; Group 6 received 4.0 mg/kg GDC-0973; Group 7 received 5.0 mg/kg GDC-0973; Group 8 received 6.0 mg/kg GDC-0973; and Group 9 received 7.5 mg/kg GDC-0973.

For the second study, female BALB/c mice were inoculated subcutaneously in the unilateral thoracic region with 100,000 CT26 murine colorectal cells in 100 µL of HBSS:matrigel. When mice achieved a mean tumor volume of approximately 200 mm3, they were randomly assigned to one of six different treatment groups on experimental day 0 and treatment was initiated on experimental day 1. Groups of 10 mice were given the following: Group 1 received MCT vehicle orally in 200 uL volume daily for 21 days and 10 mg/kg of an isotype control antibody (anti-gp120, PRO67181, PUR#20455) intraperitoneally 3 times per week; Group 2 received 7.5 mg/kg GDC-0973 orally daily for 21 days; Group 3 received 10 mg/kg anti-PD-L1 antibody PRO314483, LOT#5944.96 intraperitoneally 3 times per week; Group 4 received 10 mg/kg anti-PD-L1 antibody*PRO314483, LOT#5944.96 intraperitoneally 3 times per week and 1.0 mg/kg GDC-0973 orally daily for 21 days; Group 5 received 10 mg/kg anti-PD-L1 antibody PRO314483, LOT#5944.96 intraperitoneally 3 times per week and 3.0 mg/kg GDC-0973 orally daily for 21 days; and Group 6 received 10 mg/kg anti-PD-L1 antibody PRO314483, LOT#5944.96 intraperitoneally 3 times per week and 6.0 mg/kg GDC-0973 orally daily for 21 days. The anti-PD-L1 antibody PRO314483, LOT#5944.96 was a reverse chimera, containing the human variable region of MPDL3280A and the murine constant region of IgG2A, with an effector-less Fc D265A/N297A substitution in the constant region.

For both studies, mice were monitored for tumor growth and body weight changes two to three times per week for the duration of the study. For measurement of tumor growth, tumor volume was measured using UltraCal-IV calipers (Model 54-10-11; Fred V. Fowler Company; Newton, Mass.) with length and width measurements perpendicular to one another, and tumor volume was calculated using the equation:

$$\text{Tumor Volume}(mm^3) = (\text{Length} \times \text{Width}^2) \times 0.5$$

For measurement of body weights, mice were weighed using an Adventura Pro AV812 scale (Ohaus Corporation; Pine Brook, N.J.). Percent body weight change was calculated using the equation:

$$\text{Body weight change }(\%) = [(\text{Weight}_{Day\ new} - \text{Weight}_{Day\ 0})/\text{Weight}_{Day\ 0}] \times 100$$

Data was analyzed using R, version 2.9.2 (R Development Core Team 2008; R Foundation for Statistical Computing; Vienna, Austria), and the mixed models were fit within R using the nlme package, version 3.1-96 (Pinheiro J et al., *R package version* 3. 2009, 1-96). Plotting was performed in Prism, version 5.0b for Mac (GraphPad Software, Inc.; La Jolla, Calif.). A mixed modeling approach was used to analyze the repeated measurement of tumor volumes from the same animals over time (Pinheiro J et al., *Statistics and Computing*, Springer. 2010). This approach addressed both repeated measurements and modest dropouts before study end for reasons classifiable statistically as missing at random (MAR). The fixed effect changes in $\log_2$ (volume) by time and dose are modeled as the sum of the main effects and interaction of a natural cubic regression spline basis in time with an auto-determined natural spline basis in dose. Intercepts and growth rates (slopes) were assumed to vary randomly by animal. Tumor growth inhibition as a percentage of the control-treated group (% TGI) was calculated as the percentage of the area under the fitted curve (AUC) for the respective treatment group per day in relation to the control while the control treated mice were still on study, using the equation:

$$\% \ TGI = 100 \times (1 - AUC_{dose}/AUC_{vehicles})$$

Complete Response (CR) was defined as an individual animal whose tumor volume fell below the Limit of Detection (LOD), at any time during the study. Partial Response (PR) was defined as an individual animal whose tumor volume decreased by 50% of its initial tumor volume at any time during the study. Overall Response Rate (ORR) was defined as the sum of the complete and partial responses.

Time To Progression 5X (TTP5X) was defined as the time in days for a group's fitted tumor volume (based upon the mixed modeling analysis described above) to exceed 5 times the starting volume, rounded to the nearest half day and reported as the TTP5X for that group. Linear mixed-effects analysis was also employed to analyze the repeated measurement of body weight changes from the same animals over time.

Figure 8:
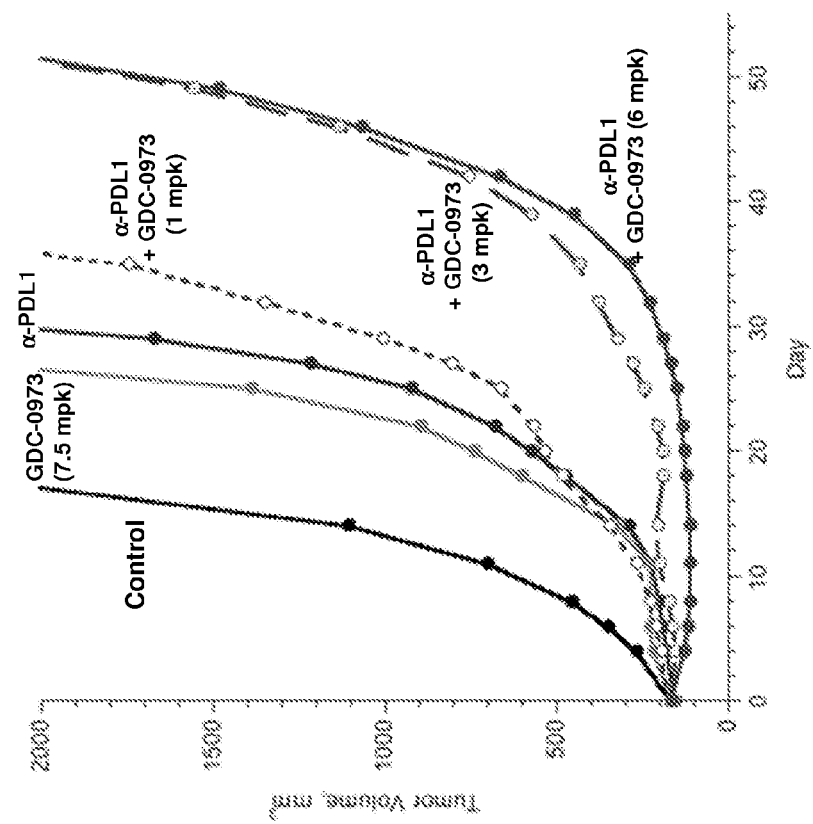
FIG. 8 is a series of graphs demonstrating that MEK inhibitor doses were more effective when used in combination with anti-PD-L1 antibody for treatment in in vivo models of colorectal cancer. (A) Graph depicting reduction in tumor volume with increasing doses of MEK inhibitor GDC-0973 treatment. (B) Graph depicting reduction in tumor volume upon administration of anti-PD-L1 antibody in combination with different doses of MEK inhibitor GDC-0973. Mpk indicates milligrams per kilogram (mg/kg).
Figure 8:
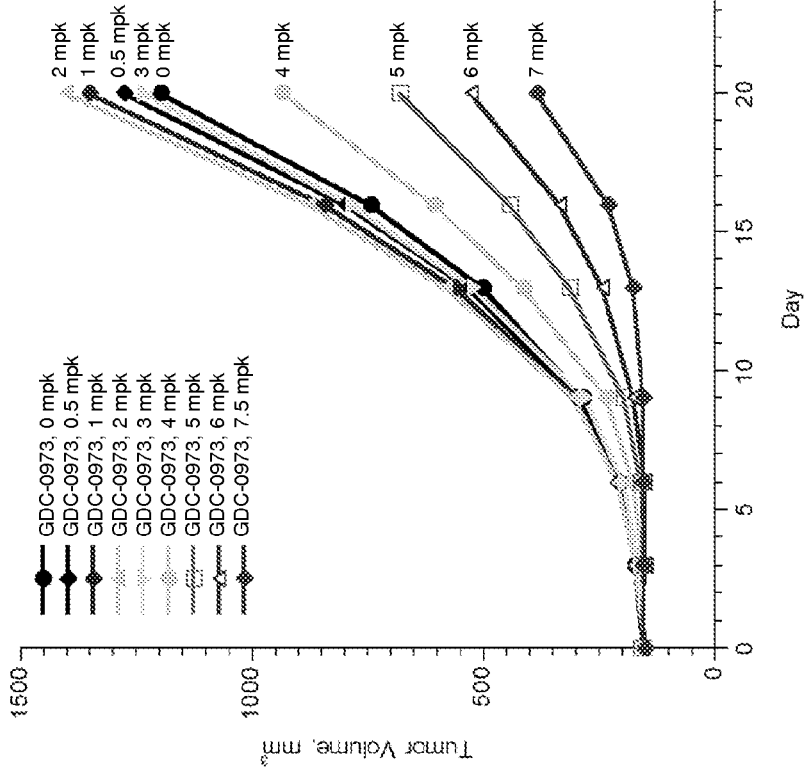

Treatment with increasing concentrations of MEKi GDC-0973 suppressed tumor growth with maximal inhibition demonstrated by the 7.5 mg/kg GDC-0973 treatment group at 20 days post-treatment (FIG. 8A, Table 2).

TABLE 2

Increased TGI due to increasing doses of MEKi GDC-0973

| Treatment | % TGI |
|---|---|
| Vehicle | 0 |
| GDC-0973, 0.5 mg/kg | −8 |
| GDC-0973, 1.0 mg/kg | −16 |

TABLE 2-continued

Increased TGI due to increasing doses of MEKi GDC-0973

| Treatment | % TGI |
| --- | --- |
| GDC-0973, 2.0 mg/kg | −21 |
| GDC-0973, 3.0 mg/kg | −4 |
| GDC-0973, 4.0 mg/kg | 27 |
| GDC-0973, 5.0 mg/kg | 55 |
| GDC-0973, 6.0 mg/kg | 72 |
| GDC-0973, 7.5 mg/kg | 87 |

Combination treatment with the anti-PD-L1 antibody and MEKi GDC-0973 demonstrated enhanced reduction of tumor growth for a longer period of time as compared to treatment with anti-PD-L1 antibodies or MEKi GDC-0973 alone (FIG. 8B, Table 3). Furthermore, lower dosage concentrations of MEKi GDC-0973 (1 mg/kg, 3 mg/kg, and 6 mg/kg) were more effective at suppressing tumor growth when used in combination with the anti-PD-L1 antibody as compared to when a higher dosage concentration of MEKi GDC-0973 was used alone (7.5 mg/kg) (FIGS. 8A and B, Table 3).

TABLE 3

Effectiveness of anti-PD-L1 antibody and MEKi GDC-0973 combination treatment

| Treatment | %TGI | TTP5X (days) | % PR | % CR |
| --- | --- | --- | --- | --- |
| Control | 0 | 12 | 0 | 0 |
| anti-PD-L1 antibody | 78 | 24 | 20 | 0 |
| GDC-0973, 7.5 mg/kg | 71 | 21.5 | 10 | 0 |
| anti-PD-L1 antibody + GDC-0973, 1.0 mg/kg | 78 | 30 | 20 | 10 |
| anti-PD-L1 antibody + GDC-0973, 3.0 mg/kg | 98 | 43 | 30 | 20 |
| anti-PD-L1 antibody + GDC-0973, 6.0 mg/kg | 106 | 44.5 | 40 | 20 |

Further studies were conducted to determine if additional MEK inhibitors (G02443714, G02442104, and G00039805) also enhanced the anti-tumor effect of anti-PD-L1 antibodies when used for combination treatment in a mouse model for colorectal tumors.

For combination treatment with the MEK inhibitor G02443714, female BALB/c mice were inoculated subcutaneously in the unilateral thoracic region with 100,000 CT26 murine colorectal cells in 100 μL of HBSS:matrigel. When mice achieved a mean tumor volume of approximately 200 mm$^3$, they were randomly assigned to one of four different treatment groups on experimental day 0 and treatment was initiated on experimental day 1. Groups of 10 mice were given the following: Group 1 received MCT vehicle orally in 200 uL volume daily for 21 days and 10 mg/kg of an isotype control antibody (anti-gp120, PRO67181, PUR#20455) intraperitoneally 3 times per week; Group 2 received 25 mg/kg G02443714 orally daily for 21 days; Group 3 received 10 mg/kg anti-PD-L1 antibody PRO314483, LOT#5944.96 intraperitoneally 3 times per week; and Group 4 received 10 mg/kg anti-PD-L1 antibody PRO314483, LOT#5944.96 intraperitoneally 3 times per week and 25 mg/kg G02443714 orally daily for 21 days. G02443714 as well as oral vehicle (MCT) were dosed orally by gavage four hours prior to administration of anti-PD-L1 and/or isotype control antibody.

For combination treatment with the MEK inhibitor G02442104, female BALB/c mice were inoculated subcutaneously in the unilateral thoracic region with 100,000 CT26 murine colorectal cells in 100 μL of HBSS:matrigel. When mice achieved a mean tumor volume of approximately 200 mm$^3$, they were randomly assigned to one of four different treatment groups on experimental day 0 and treatment was initiated on experimental day 1. Groups of 10 mice were given the following: Group 1 received MCT vehicle orally in 200 uL volume daily for 21 days and 10 mg/kg of an isotype control antibody (anti-gp120, PRO67181, PUR#20455) intraperitoneally 3 times per week; Group 2 received 25 mg/kg G02442104 orally daily for 21 days; Group 3 received 10 mg/kg anti-PD-L1 antibody PRO314483, LOT#5944.96 intraperitoneally 3 times per week; and Group 4 received 10 mg/kg anti-PD-L1 antibody PRO314483, LOT#5944.96 intrapeiitoneally 3 times per week and 25 mg/kg G02442104 orally daily for 21 days. G02442104 as well as oral vehicle (MCT) were dosed orally by gavage four hours prior to administration of anti-PD-L1 and/or isotype control antibody.

For combination treatment with the MEK inhibitor G00039805, female BALB/c mice were inoculated subcutaneously in the unilateral thoracic region with 100,000 CT26 murine colorectal cells in 100 μL of HBSS:matrigel. When mice achieved a mean tumor volume of approximately 200 mm3, they were randomly assigned to one of four different treatment groups on experimental day 0 and treatment was initiated on experimental day 1. Groups of 10 mice were given the following: Group 1 received MCT vehicle orally in 200 uL volume daily for 21 days and 10 mg/kg of an isotype control antibody (anti-gp120, PRO67181, PUR#20455) intraperitoneally 3 times per week; Group 2 received 100 mg/kg G00039805 orally daily for 21 days; Group 3 received 10 mg/kg anti-PD-L1 antibody PRO314483, LOT#5944.96 intraperitoneally 3 times per week; and Group 4 received 10 mg/kg anti-PD-L1 antibody PRO314483, LOT#5944.96 intraperitoneally 3 times per week and 100 mg/kg G00039805 orally daily for 21 days. G00039805 as well as oral vehicle (MCT) were dosed orally by gavage four hours prior to administration of anti-PD-L1 and/or isotype control antibody.

For all three combination studies with G02443714, G02442104, or G00039805, mice were monitored for tumor growth and body weight changes two to three times per week for the duration of the study. For measurement of tumor growth, tumor volume was measured using UltraCal-IV calipers (Model 54-10-111; Fred V. Fowler Company; Newton, Mass.) with length and width measurements perpendicular to one another, and tumor volume was calculated using the equation:

Tumor Volume (mm$^3$)=(Length×Width$^2$)×0.5

For measurement of body weights, mice were weighed using an Adventura Pro AV812 scale (Ohaus Corporation; Pine Brook, N.J.). Percent body weight change was calculated using the equation:

Body weight change (%)=[(Weight$_{Day\ new}$−Weight$_{Day\ 0}$)/Weight$_{Day\ 0}$]×100

Data was analyzed using R, version 2.9.2 (R Development Core Team 2008; R Foundation for Statistical Computing; Vienna, Austria), and the mixed models were fit within R using the nlme package, version 3.1-96 (Pinheiro J et al., *R package version* 3. 2009, 1-96). Plotting was performed in Prism, version 5.0 b for Mac (GraphPad Software, Inc.; La Jolla, Calif.). A mixed modeling approach was used to analyze the repeated measurement of tumor volumes from the same animals over time (Pinheiro J et al., Statistics and Computing, Springer. 2010). This approach addressed both repeated measurements and modest dropouts before study end for reasons classifiable statistically as missing at random (MAR). The fixed effect changes in $\log_2$ (volume) by time and dose are modeled as the sum of the main effects and interaction of a natural cubic regression spline basis in time with an auto-determined natural spline basis in dose. Intercepts and growth rates (slopes) were assumed to vary randomly by animal. Tumor growth inhibition as a percentage of the control-treated group (% TGI) was calculated as the percentage of the area under the fitted curve (AUC) for the respective treatment group per day in relation to the control while the control treated mice were still on study, using the equation:

% TGI=100×(1−$AUC_{dose}$/$AUC_{vehicles}$)

Complete Response (CR) was defined as an individual animal whose tumor volume fell below the Limit of Detection (LOD), at any time during the study. Partial Response (PR) was defined as an individual animal whose tumor volume decreased by 50% of its initial tumor volume at any time during the study. Overall Response Rate (ORR) was defined as the sum of the complete and partial responses.

Time To Progression 5X (TTP5X) was defined as the time in days for a group's fitted tumor volume (based upon the mixed modeling analysis described above) to exceed 5 times the starting volume, rounded to the nearest half day and reported as the TTP5X for that group. Linear mixed-effects analysis was also employed to analyze the repeated measurement of body weight changes from the same animals over time.

Figure 9:
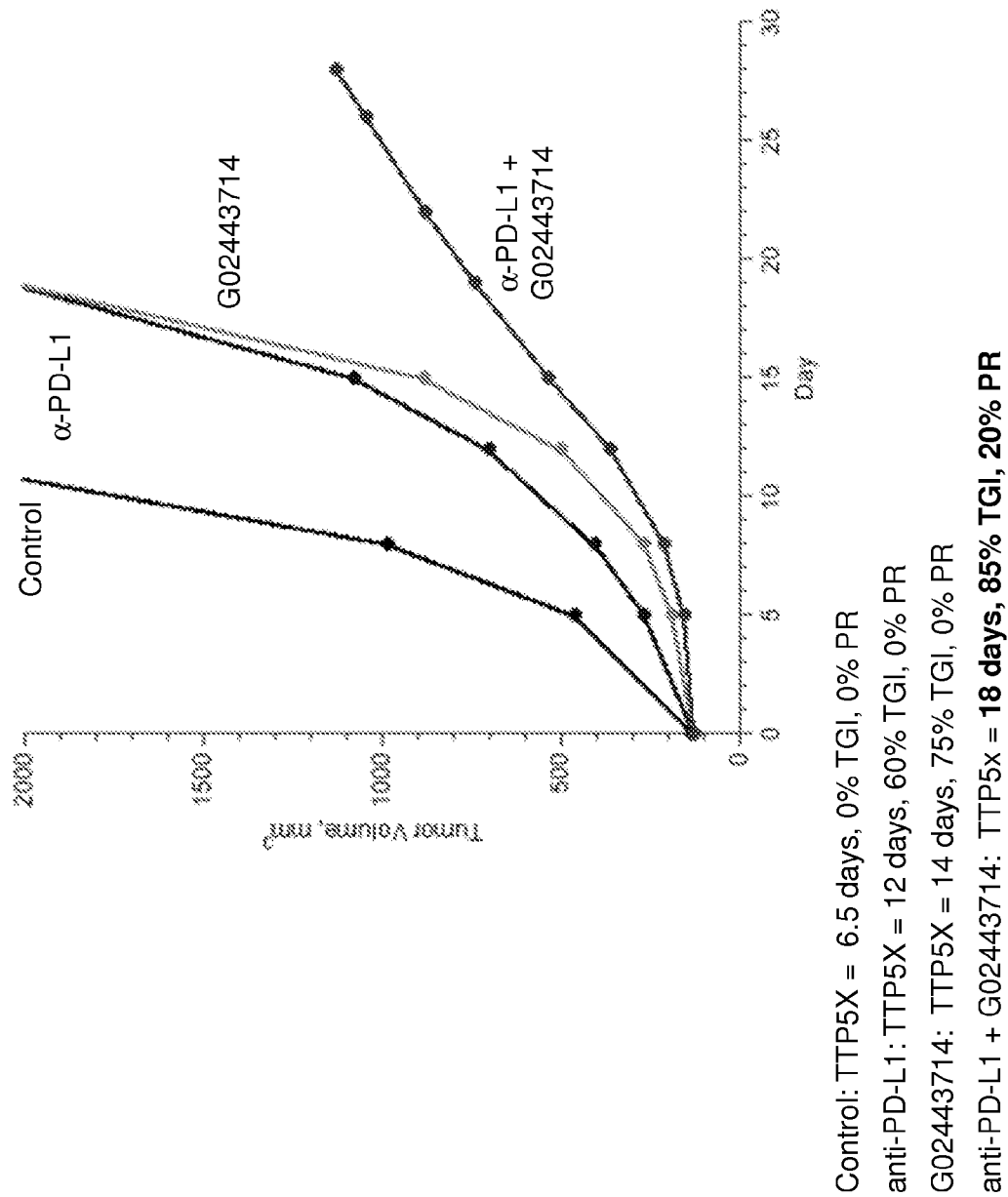
FIG. 9 is a graph demonstrating that treatment with MEK inhibitor G02443714 enhanced the anti-tumor activity of anti-PD-L1 antibodies in in vivo models of colorectal cancer. An enhanced reduction in tumor volume with anti-PD-L1 antibody and MEK inhibitor combination treatment was observed as compared to treatment with anti-PD-L1 antibody or MEK inhibitor G02443714 alone.
Figure 10:
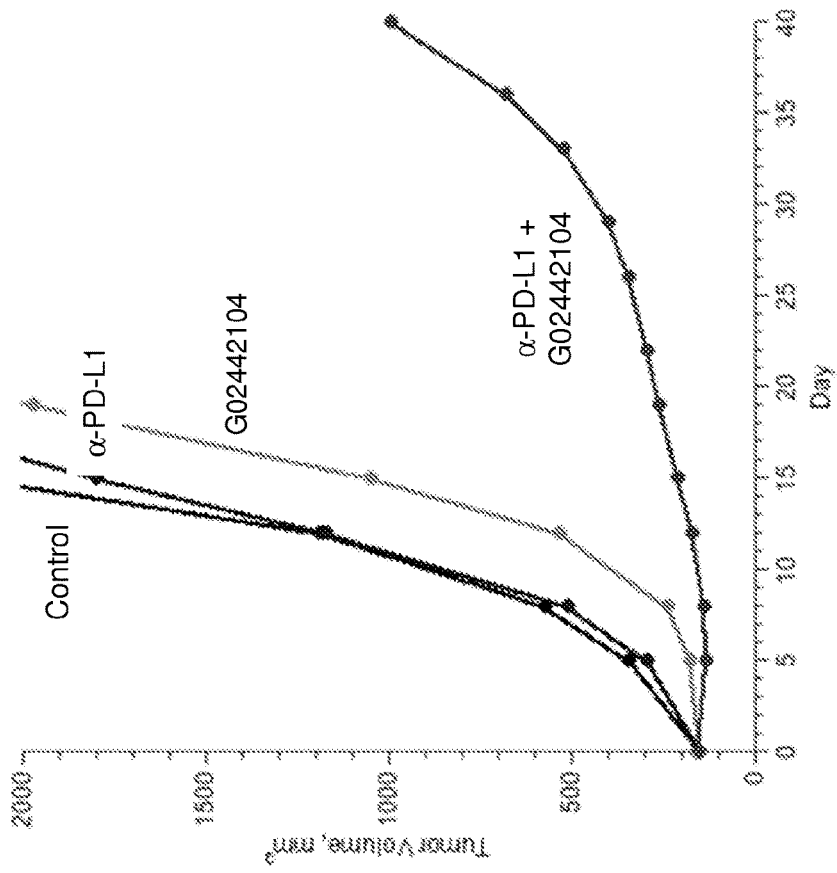
FIG. 10 is a graph demonstrating that treatment with MEK inhibitor G02442104 enhanced the anti-tumor activity of anti-PD-L1 antibodies in in vivo models of colorectal cancer. An enhanced reduction in tumor volume with anti-PD-L1 antibody and MEK inhibitor combination treatment was observed as compared to treatment with anti-PD-L1 antibody or MEK inhibitor G02442104 alone.
Figure 11:
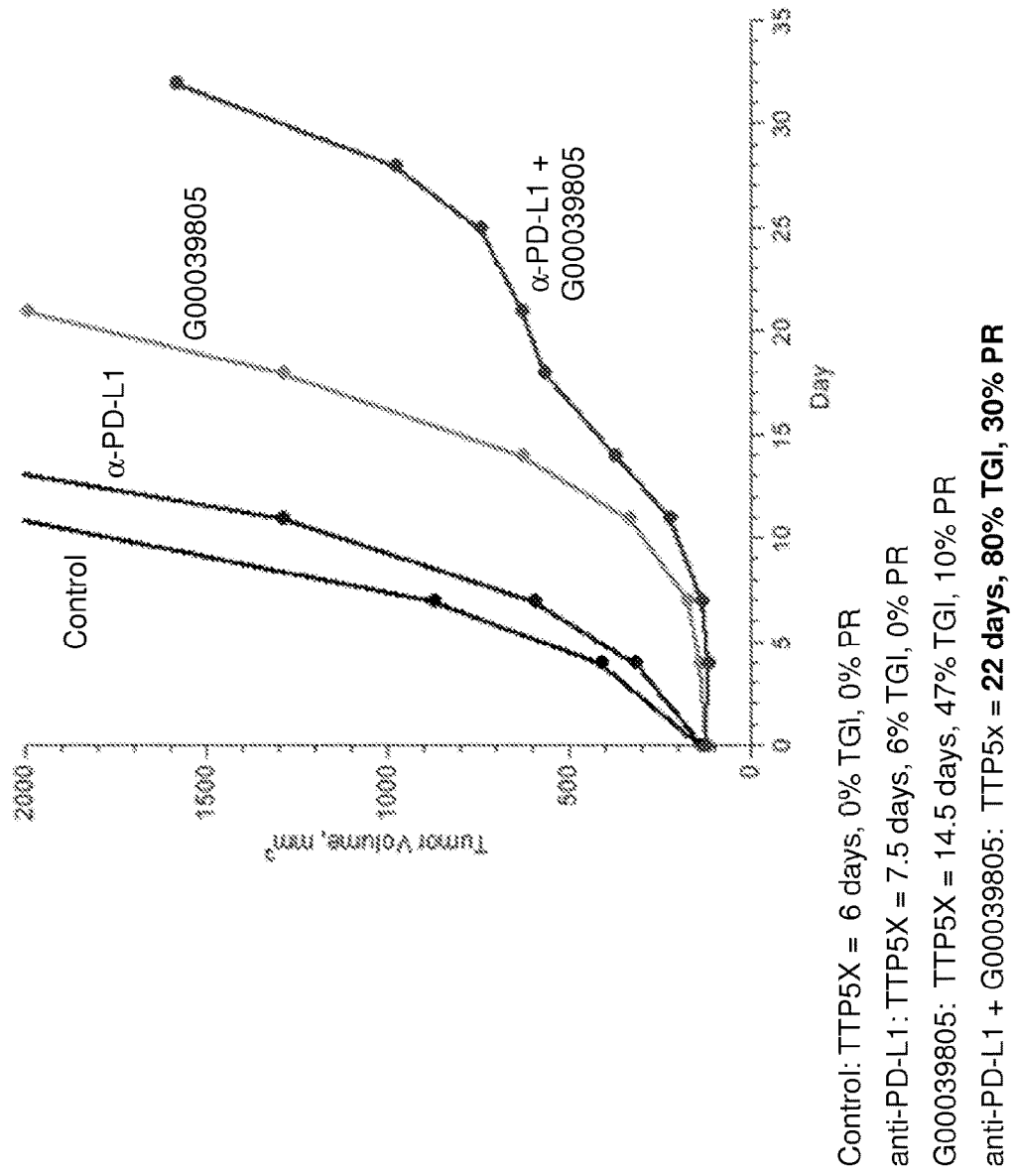
FIG. 11 is a graph demonstrating that treatment with MEK inhibitor G00039805 enhanced the anti-tumor activity of anti-PD-L1 antibodies in in vivo models of colorectal cancer. An enhanced reduction in tumor volume with anti-PD-L1 antibody and MEK inhibitor combination treatment was observed as compared to treatment with anti-PD-L1 antibody or MEK inhibitor G00039805 alone.

Combination treatment with the anti-PD-L1 antibody and G02443714 resulted in enhanced reduction of tumor growth for a longer period of time as compared to treatment with anti-PD-L1 antibodies or G02443714 alone with a 20% partial response observed at 18 days (FIG. 9). Combination treatment with the anti-PD-L1 antibody and G02442104 also resulted in enhanced reduction of tumor growth for a longer period of time as compared to treatment with anti-PD-L antibodies or MEKi G02442104 alone with a 40% partial response and 10% complete response observed at 37.5 days (FIG. 10). In addition, combination treatment with the anti-PD-L1 antibody and G00039805 resulted in enhanced reduction of tumor growth for a longer period of time as compared to treatment with anti-PD-L1 antibodies or MEKi GOQ039805 alone with a 30% partial response observed at 22 days (FIG. 1). Altogether these results demonstrate that a variety of MEK inhibitors can enhance the anti-tumor activity of anti-PD-L1 antibodies to inhibit tumor growth.

Example 6

Figure 12:
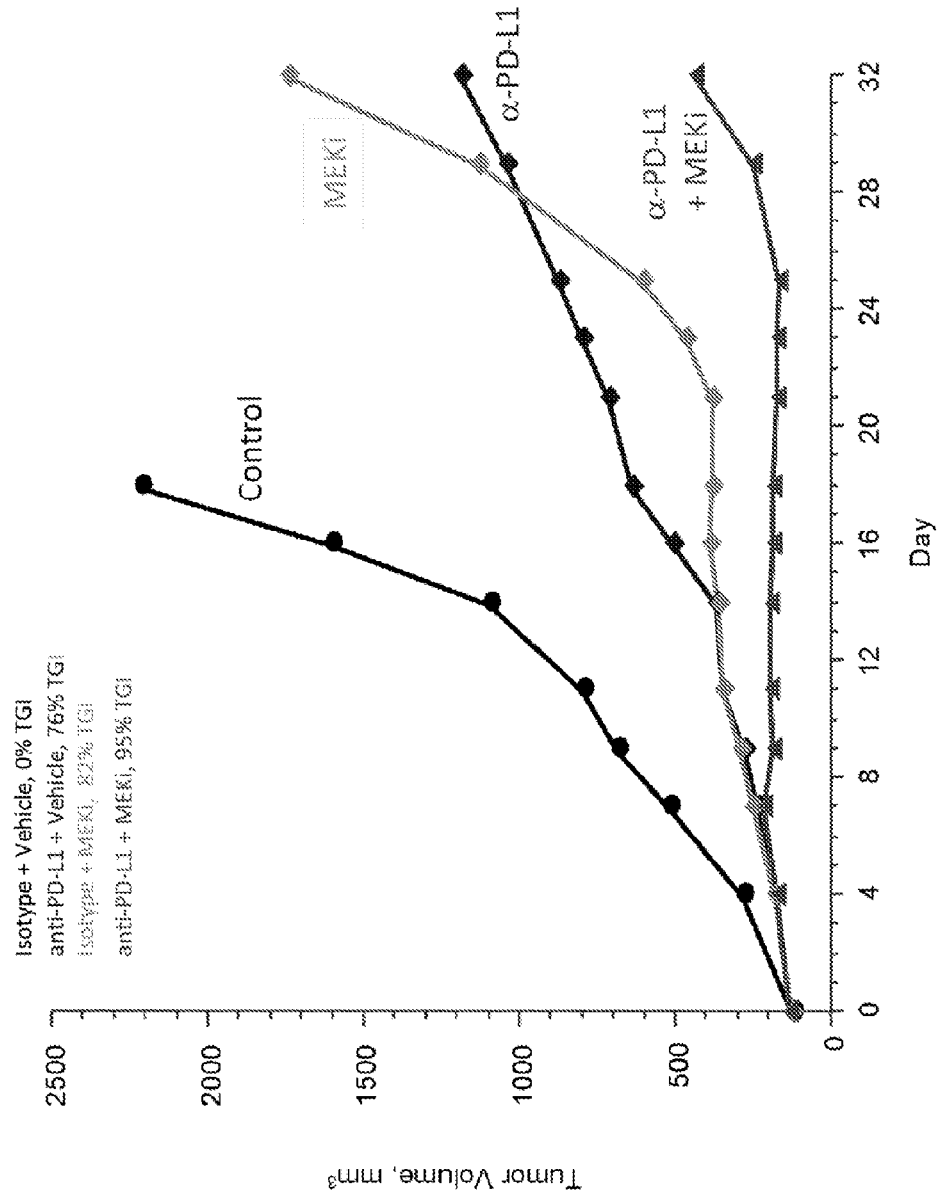
FIG. 12 demonstrates that MEK inhibitor treatment enhanced anti-tumor activity of anti-PD-L1 antibodies in in vivo models of melanoma. (A and B) Graph depicting changes in tumor volume with anti-PD-L1 antibodies and MEK inhibitor co-treatment demonstrates significantly reduced tumor growth as compared to anti-PD-L1 antibodies or MEK inhibitor treatment alone.
Figure 13:
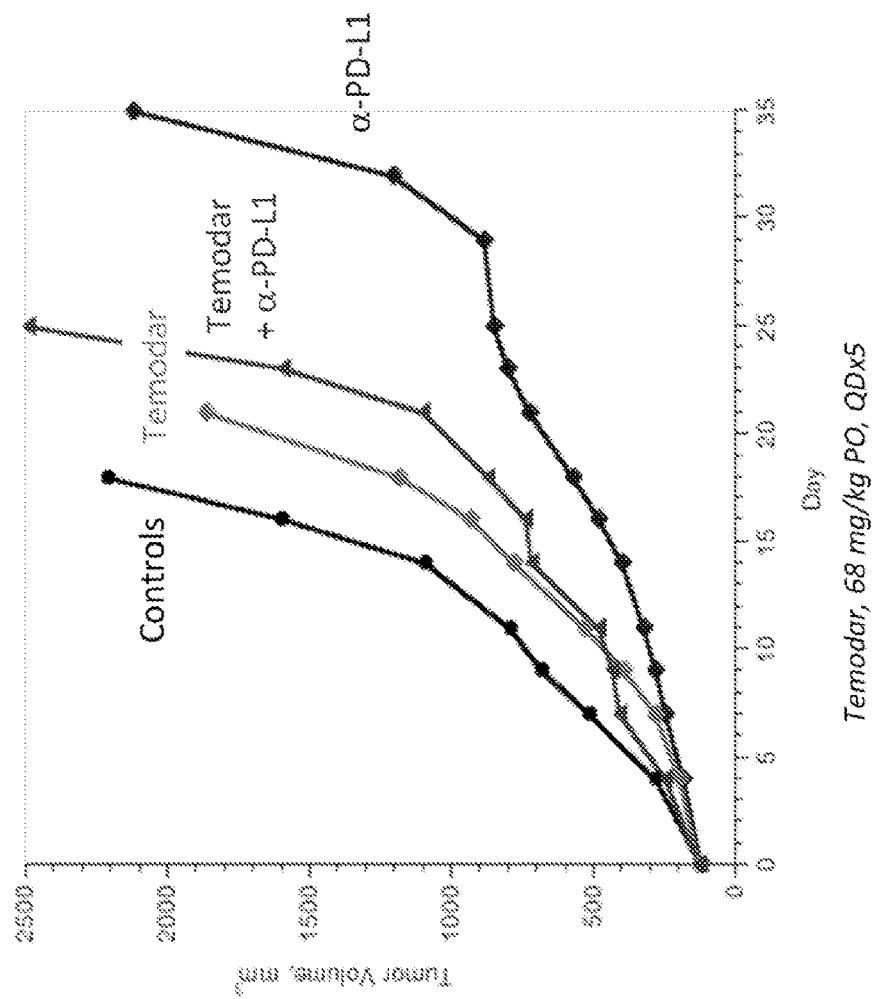
FIG. 13 is a graph demonstrating that co-treatment with anti-PD-L1 antibodies and a chemotherapeutic agent Temodar did not reduce tumor growth in an in vivo model of melanoma. Therefore, the anti-tumor effect of MEK inhibitor and anti-PD-L1 antibodies is specific.
Figure 14:
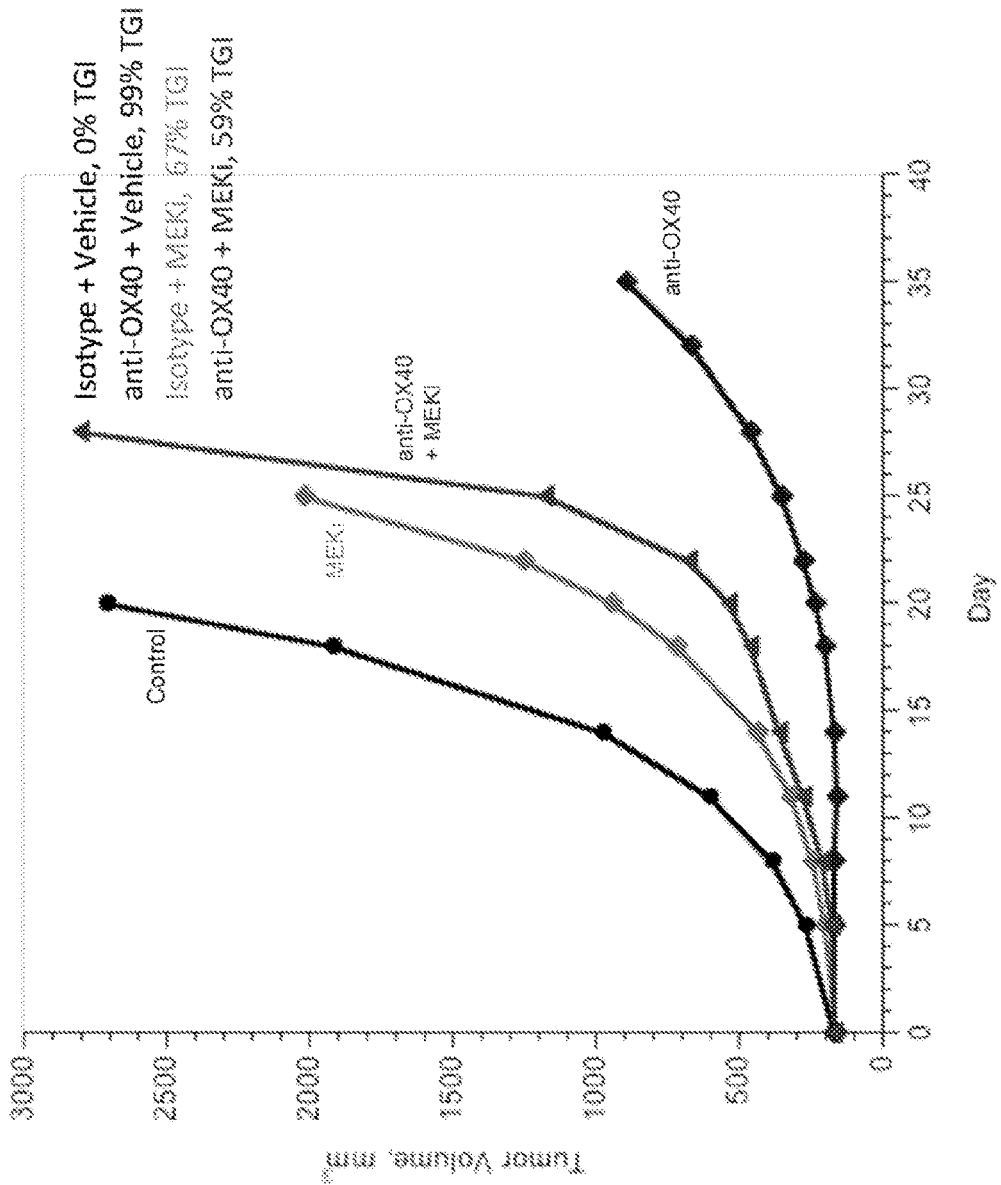
FIG. 14 is a graph demonstrating that co-treatment with anti-OX40 antibodies and a MEK inhibitor did not reduce tumor growth in an in vivo colorectal model. Therefore, the anti-tumor effect of MEK inhibitor and anti-PD-L1 antibodies is specific.

MEK Inhibition Enhanced Anti-Tumor Activity of Anti-PD-L1 Antibodies in Melanoma Tumors In Vivo To determine if MEKi enhanced the anti-tumor effect of anti-PD-L1 antibodies, mouse models for melanoma tumors were treated with the combination treatment. Briefly, mice were inoculated subcutaneously with tumor cells and allowed to grow tumors. When tumor bearing mice achieved a mean tumor volume of 100-200 mm3, mice were randomly assigned to 1 of 4 treatment groups. Group 1: received 10 mg/kg of an isotype control antibody (anti-gp120, PRO67181, PUR#20455) intraperitoneally three times a week for three weeks plus MCT control vehicle, orally, daily for 21 days; Group 2: received 10 mg/kg anti-PD-L1 antibody PRO314483, LOT#59554.96 intraperitoneally three times a week for three weeks; Group 3: received 10 mg/kg of an isotype control antibody (anti-gp120, PRO67181, PUR#20455) intraperitoneally three times a week for three weeks plus 75 mg/kg MEKi G-38963, orally, daily for 21 days; Group 4: received 10 mg/kg of an anti-PD-L1 antibody PRO314483, LOT#59554.96 intraperitoneally three times a week for three weeks plus 75 mg/kg MEKi G-38963, orally, daily for 21 days. Mice were monitored for tumor growth and body weight changes. Blockade of PD-L1 with anti-PD-L1 antibody PRO314483, LOT#59554.96 in Cloudman S91 (FIG. 12) melanoma tumors was effective as a single agent therapy at preventing tumor growth. Treatment with MEKi G-38963 was also highly effective as a single agent therapy at preventing tumor growth (FIG. 12) and was comparable to anti-PD-L1 antibody treatment. Combination treatment with anti-PD-L1 antibodies and MEKi significantly inhibited tumor growth in both melanoma cell lines. In contrast, Temodar, a chemotherapeutic agent, when used in combination with anti-PD-L1 antibodies inhibited the anti-tumor activity of anti-PD-L 1 antibodies (FIG. 13). Similar results were obtained when an antibody that blocks the T cell OX40 co-stimulatory molecule was used in combination with the MEK inhibitor G-38963 (FIG. 14). These results indicate that MEKi specifically enhanced the anti-tumor activity of PD-L1 blockade and therefore worked synergistically with anti-PD-L1 antibodies to inhibit melanoma tumor growth.

Example 7

MEK Inhibitor Increased Activation of Dendritic Cells Independently of PDL1 Antibody Activity Previous studies have indicated that MEK inhibition can augment immune function by downregulation of surface PD-L1 suggesting that the effects of MEKi were mediated via alterations in PD-L1 expression. To determine if enhanced tumor immunogenicity is due to dependency of PD-L1 expression upon MEK activation, activation of dendritic cells was compared when treated with MEKi GDC-0973 alone, anti-PD-L1 antibodies (a chimeric antibody composed of variable regions of MPDL3280A fused to mouse IgG2a constant sequences that contain an Fc mutation to prevent effective binding to Fcgamma receptors) alone or MEKi in combination with anti-PD-L1 antibodies. Briefly, mouse bone marrow cells were isolated and seeded at $2 \times 10^6$ per 10 ml total volume per 10 cm non-tissue culture treated dishes with 40 ng/ml mouse GM-CSF for 7 days. Fresh media was half-exchanged every 2-3 days. Culture medium was RPMI-1640 with 10% fetal bovine serum, 20 μM HEPES, 55 μM 2-mercaptoethanol, 50 μg/ml gentamicin, and 1:100 dilutions of the following supplements from Gibco: Gluta-MAX, sodium pyruvate, penicillin/streptomycin, and non-essential amino acids. On day 7 all cells were harvested and washed, then seeded at 100,000 cells/well in a 96-well flat-bottom plate. MEK inhibitor GDC-0973 was added at a final concentration of 1 μM, anti-PDLI human/mouse reverse chimera or anti-Ragweed mouse IgG2a isotype control (Genentech PUR 22251) were added at 10 μg/ml. Prior to adding to cells for a final concentration of 1 μg/ml each, anti-CD40 clone FGK-45 (Genentech lot 68020-62) was crossed-linked with goat anti-Rat IgG Fc-gamma-receptor (Jackson ImmunoResearch) at room temperature for one hour. After 48 hours of stimulation, cells were harvested and transferred to a 96-well V-bottom plate. Samples were first Fc receptor blocked (purified anti-CD16/

Figure 15:
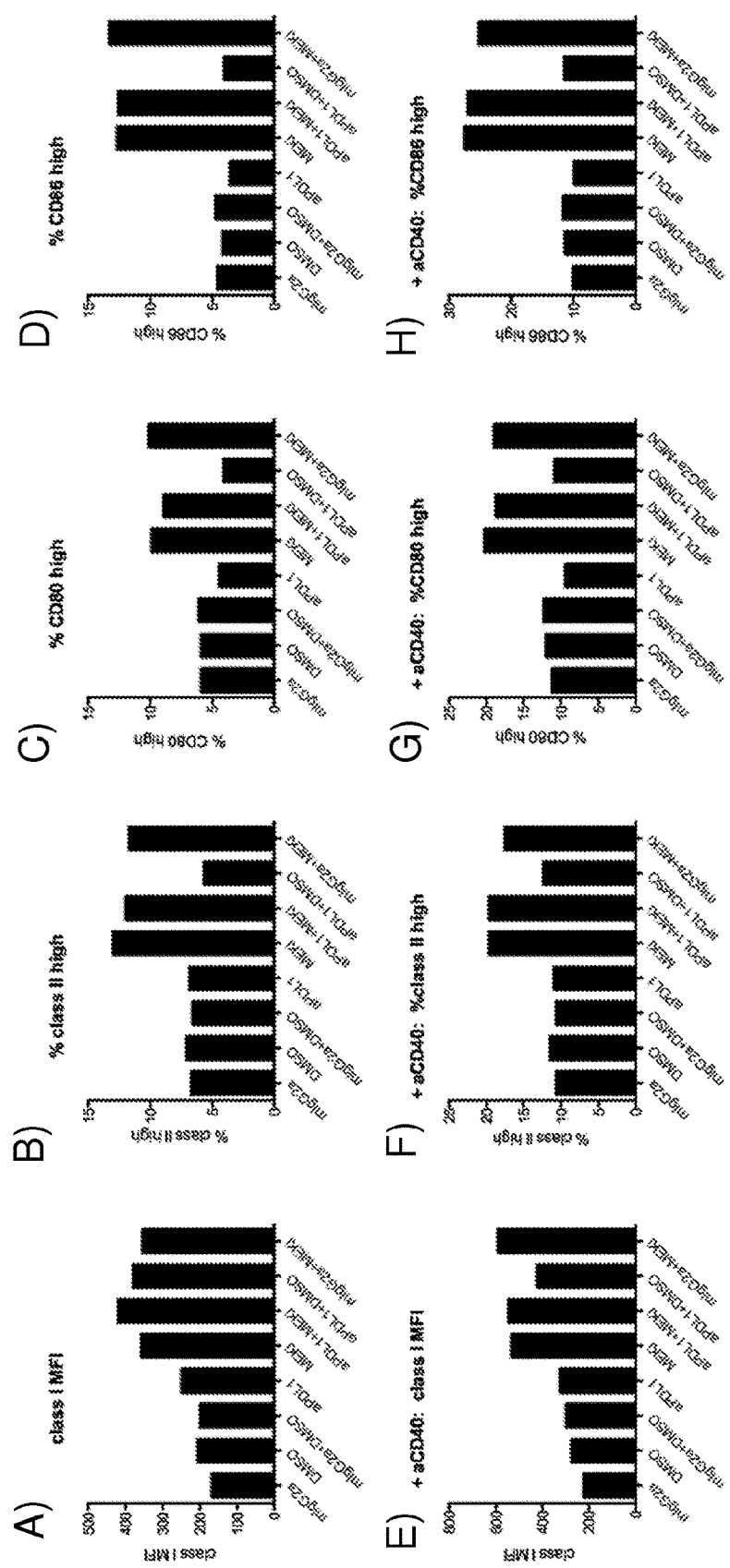
FIG. 15 contains several graphs showing that MEK inhibitor increased activation of dendritic cells independently of anti-PD-L1 antibody treatment. (A) Graph demonstrating that anti-PD-L1 antibody treatment slightly increased MHC I surface expression. MEK inhibitor treatment significantly enhanced MHCI expression, however co-treatment with anti-PD-L1 antibodies did not enhance the effect of MEK inhibitor treatment. (B-D) Graphs demonstrating that anti-PD-L1 antibody treatment did not increase expression of dendritic cell activation markers MHC II, CD80, and CD86. In contrast MEK inhibitor treatment significantly enhanced expression of dendritic cell activation markers. Co-treatment with anti-PD-L1 antibodies did not enhance the effect of MEK inhibitor treatment. (E-H) Graphs demonstrating that stimulation of dendritic cells with anti-CD40 antibodies did not alter the effect of MEK inhibitor and anti-PD-L1 co-treatment on dendritic cell activation.

CD32 from BD Biosciences, 5 µg/ml) and then stained with I-A/I-E-FITC, H-2 Db/H-2 Kb-biotin (followed by streptavidin-PE), CD11c-APC, CD86-FITC, and CD80-PE (all from BD Biosciences). Propidium iodide was included to exclude dead cells. Samples were run on a BD FACSCaliber flow cytometer and data was analyzed using FlowJo software (Tree Star, Inc.). Treatment with functionally blocking anti-PD-L1 antibodies alone modestly increased DC surface expression of MHC-I (FIG. 15A) however it did not induce expression of DC surface activation markers MHC-II (FIG. 15B), CD80 (FIG. 15C), or CD86 (FIG. 15D). In contrast MEKi treatment enhanced MHC-II, CD80, and CD86 as well as MHC-I expression. Interestingly, combination treatment of MEKi and anti-PD-L1 antibodies did not alter DC surface activation markers as compared to MEKi alone. Similar results were obtained with the addition of the co-stimulatory anti-CD40 antibodies (FIG. 15E-H). These novel findings indicate that MEKi induced activation of DCs independently of its effect on PD-L expression. Altogether these results demonstrate that MEKi increased tumor immunogenicity by mechanisms unique from anti-PDL and provide support for combining MEKi and PD-L blockade for optimal enhancement of anti-tumor immunity.

Example 8a

MEK Assay (MEK Activity Assay)

Constitutively activated human mutant MEK1 expressed in insect cells is used as source of enzymatic activity at a final concentration in the kinase assay of 62.5 nM.

The assay is carried out for 30 minutes in the presence of 50 µM ATP using recombinant GST-ERK1 produced in *E. Coli* as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Example 8b

MEK Assay (MEK Activity Assay)

Constitutively activated human mutant MEK1 expressed in insect cells is used as source of enzymatic activity at a final concentration in the kinase assay of 15 nM.

The assay is carried out for 30 minutes in the presence of 50 µM ATP using recombinant GST-ERK1 produced in *E. Coli* as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. These are used at a final concentration of 4 µg/ml and 0.84 µg/ml respectively. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $ICo_5$ values are calculated using the XLfit software package (version 2.0.5).

All patents, patent applications, documents, and articles cited herein are herein incorporated by reference in their entireties.

What is claimed is:

1. A method for treating or delaying progression of colorectal cancer or melanoma in an individual comprising administering to the individual an effective amount of an anti-PD-L1 antibody and a MEK inhibitor, wherein the MEK inhibitor is selected from the group consisting of G02442104, G-38963, G02443714, G00039805 and GDC-0973, or a pharmaceutically acceptable salt or solvate thereof.

2. The method of claim 1, wherein the anti-PD-L1 antibody inhibits the binding of PD-L1 to PD-1.

3. The method of claim 1, wherein the anti-PD-L1 antibody inhibits the binding of PD-L1 to B7-1.

4. The method of claim 1, wherein the anti-PD-L1 antibody inhibits the binding of PD-L1 to both PD-1 and B7-1.

5. The method of claim 1, wherein the anti-PD-L1 antibody is selected from the group consisting of: YW243.55.S70, MPDL3280A, and MDX-1105.

6. The method of claim 1, wherein the anti-PD-L1 antibody comprises a heavy chain comprising HVR-H1 sequence of SEQ ID NO:15, HVR-H2 sequence of SEQ ID NO:16, and HVR-H3 sequence of SEQ ID NO:3; and a light chain comprising HVR-L1 sequence of SEQ ID NO:17, HVR-L2 sequence of SEQ ID NO:18, and HVR-L3 sequence of SEQ ID NO:19.

7. The method of claim 1, wherein the anti-PD-L1 antibody comprises a heavy chain variable region comprising the amino acid sequence of SEQ ID NO:24 and a light chain variable region comprising the amino acid sequence of SEQ ID NO:21.

8. The method of claim 1, wherein the MEK inhibitor is G02443714, G02442104 or G00039805.

9. The method of claim 1, wherein the cancer contains a BRAF V600E mutation.

10. The method of claim 1, wherein the cancer contains a BRAF wildtype.

11. The method of claim 1, wherein the colorectal cancer contains a KRAS wildtype.

12. The method of claim 1, wherein the colorectal cancer contains an activating KRAS mutation.

13. The method of claim 1, wherein the treatment results in a sustained response in the individual after cessation of the treatment.

14. The method of claim 1, wherein the MEK inhibitor is administered continuously.

15. The method of claim 1, wherein the MEK inhibitor is administered intermittently.

16. The method of claim 1, wherein the MEK inhibitor is administered before the anti-PD-L1 antibody.

17. The method of claim 1, wherein the MEK inhibitor is administered simultaneous with the anti-PD-L1 antibody.

18. The method of claim 1, wherein the MEK inhibitor is administered after the anti-PD-L1 antibody.

19. The method of claim 1, wherein the anti-PD-L1 antibody is a monoclonal antibody.

20. The method of claim 1, wherein the anti-PD-L1 antibody is a humanized antibody.

21. The method of claim 1, wherein the anti-PD-L1 antibody is a human antibody.

22. The method of claim 1, wherein the anti-PD-L1 antibody is administered intravenously, intramuscularly, subcutaneously, topically, orally, transdermally, intraperitoneally, intraorbitally, by implantation, by inhalation, intrathecally, intraventricularly, or intranasally.

23. A method for treating or delaying progression of colorectal cancer in an individual comprising administering to the individual an effective amount of GDC-0973, or a pharmaceutically acceptable salt thereof, and an effective amount of an anti-PD-L1 antibody, wherein the anti-PD-L1 antibody comprises a heavy chain comprising an HVR-H1 sequence of SEQ ID NO:15, an HVR-H2 sequence of SEQ ID NO:16, and an HVR-H3 sequence of SEQ ID NO:3; and a light chain comprising an HVR-L1 sequence of SEQ ID NO:17;, an HVR-L2 sequence of SEQ ID NO:18, and an HVR-L3 sequence of SEQ ID NO:19.

24. The method of claim 23, wherein the heavy chain comprises a heavy chain variable region comprising the amino acid sequence of SEQ ID NO:24 and the light chain comprises a light chain variable domain comprising the amino acid sequence of SEQ ID NO:21.

25. The method of claim 23, wherein the anti-PDL1 antibody is MPDL3280A.

26. A method for treating or delaying progression of melanoma in an individual comprising administering to the individual an effective amount of GDC-0973, or a pharmaceutically acceptable salt thereof, and an effective amount of an anti-PD-L1 antibody, wherein the melanoma is BRAF wildtype, and wherein the anti-PD-L1 antibody comprises a heavy chain comprising an HVR-H1 sequence of SEQ ID NO:15, an HVR-H2 sequence of SEQ ID NO:16, and an HVR-H3 sequence of SEQ ID NO:3; and a light chain comprising an HVR-L1 sequence of SEQ ID NO:17, an HVR-L2 sequence of SEQ ID NO:18, and an HVR-L3 sequence of SEQ ID NO:19.

27. The method of claim 26, wherein the heavy chain comprises a heavy chain variable region comprising the amino acid sequence of SEQ ID NO:24 and the light chain comprises a light chain variable domain comprising the amino acid sequence of SEQ ID NO:21.

28. The method of claim 26, wherein the anti-PDL1 antibody is MPDL 3280A.

29. The method of claim 1, wherein the MEK inhibitor is s G02442104, or a pharmaceutically acceptable salt or solvate thereof.

30. The method of claim 1, wherein the MEK inhibitor is G-38963, or a pharmaceutically acceptable salt or solvate thereof.

31. The method of claim 1, wherein the MEK inhibitor is G02443714, or a pharmaceutically acceptable salt or solvate thereof.

32. The method of claim 1, wherein the MEK inhibitor is G00039805, or a pharmaceutically acceptable salt or solvate thereof.

33. The method of claim 1, wherein the MEK inhibitor is GDC-0973, or a pharmaceutically acceptable salt or solvate thereof.

* * * * *